US005719296A

United States Patent [19]
Acton, III et al.

[11] Patent Number: 5,719,296
[45] Date of Patent: Feb. 17, 1998

[54] PSEUDOPEPTIDE LACTAM INHIBITORS OF PEPTIDE BINDING TO MHC CLASS II PROTEINS

[75] Inventors: John J. Acton, III, Cranford; Alan D. Adams, Cranford; Jeffrey D. Hermes, Warren; A. Brian Jones, Scotch Plains; William Hugh Parsons, Belle Mead; Peter J. Sinclair, Highland Park, all of N.J.

[73] Assignee: Merck & Co., Inc., Rahway, N.J.

[21] Appl. No.: 736,835

[22] Filed: Oct. 28, 1996

[51] Int. Cl.$^6$ .................. C07D 207/12; C07D 207/24; C07D 207/36; A61K 31/40
[52] U.S. Cl. ............................. 548/550; 514/426
[58] Field of Search ................. 548/550; 514/426

[56] References Cited

U.S. PATENT DOCUMENTS

| | | | |
|---|---|---|---|
| 4,254,107 | 3/1981 | Veber et al. | 424/177 |
| 4,493,934 | 1/1985 | Veber et al. | 548/550 |
| 5,202,344 | 4/1993 | Becker et al. | 548/550 X |
| 5,420,293 | 5/1995 | Negele et al. | 548/550 |
| 5,514,694 | 5/1996 | Powers et al. | 514/357 |
| 5,541,343 | 7/1996 | Himmelsbach et al. | 514/424 |

FOREIGN PATENT DOCUMENTS

| | | |
|---|---|---|
| WO96/01646 | 1/1996 | WIPO . |
| WO96/20215 | 7/1996 | WIPO . |
| WO96/30035 | 10/1996 | WIPO . |

OTHER PUBLICATIONS

Hanson et al., Biorganic & Medicinal Chemistry Letters, vol. 6, No. 16 (1996), pp. 1931–1936, "Design of MHC Class II (DR4) ligands using conformationally restricted imino acids at p3 and p5".

Sette et al., J. of Immunol., vol. 151 (1993), pp. 3163–3170, "HLA DR4w4–Binding motifs illustrate the biochemical basis of degeneracy and specificity in peptide–DR interactions".

Rudensky et al., Nature, vol. 359 (1992), pp. 429–431, "Truncation variants of peptides isolated from MHC Class II molecules suggest sequence motifs".

Chicz et al., Nature, vol. 358 (1992), pp. 764–768, "Predominant naturally processed peptides bound to HLA DR1 are derived from MHC–related molecules and are heterogeneous in size".

Hammer et al., Cell, 74 (1993), pp. 197–203, "Promiscuous and allele–specific anchors in HLA–DR–binding peptides".

Germain et al., Annu. Rev. Immunol., vol. 11 (1993), pp. 403–450, "The biochemistry and cell biology of antigen processing and presentation".

Jordensen et al., Annu. Rev. Immunol., vol. 10 (1992), pp. 835–873, "Molecular components of T–cell recognition".

Stern et al., Nature, vol. 368 (1994), pp. 215–221, "Crystal structure of the human class II MHC protein HLA–DR1 complexed with an influenza virus peptide".

Hurtenbach et al., J. Exp. Med., vol. 177 (1993), pp. 1499–1504, "Prevention of autoimmune diabetes in non-obese diabetic mice by treatment with a Class II major histocompatibility complex–blocking peptide".

Guery et al., J. Exp. Med., vol. 177 (1993), pp. 1461–1468, "Selective immunosuppression by administration of major histocompatibility complex Class II-binding peptides".

Wauben et al., J. Immunol., vol. 152 (1994), pp. 4211–4220, "Inhibition of experimental autoimmune encephalomyelitis by MHC Class II binding competitor peptides depends on the relative MHC binding affinity of the disease–inducing peptide".

Gautam et al., J. of Immunol. vol. 148 (1992), pp. 3049–3054, "Inhibition of experimental autoimmune encephalomyelitis by a nonimmunogenic non-self peptide that binds to I–Au1".

Skinner et al., Annals of the Rheumatic Diseases, vol. 53 (1994), pp. 171–177, "Lymphocyte responses to DR 1/4 restricted peptides in rheumatoid arthritis".

Hammer et al., Proc. Nat'l Acad. Sci. USA, vol. 91, pp. 4456–4460 (1994), "High–affinity binding of short peptides to major histocompatibility complex class II molecules by anchor combinations".

Jones et al., Abstracts of the 25th Nat'l Medicinal Chemistry Symposium, Jun. 18–22, 1996, Ann Arbor, MI., "The development of peptidomimetic inhibitors of the binding of antigenic peptide to MHC Class II".

Adams et al., Abstracts of 25th Nat'l Medicinal Chemistry Symposium, University of Michigan, Ann Arbor, MI, Jun. 18–22, 1996, Abstract No. 98, "The development of small molecule inhibitors of the binding of antigenic peptide to MHC Class II".

Jones, et al., Abstracts of the XIVth Int'l Symposium on Medicinal Chemistry, Maastricht, The Netherlands, Sep. 8–12, 1996, "Inhibition of MHC Class II ligation by peptidomimetics: prospects for antigen specific immunosuppression".

(List continued on next page.)

*Primary Examiner*—Floyd D. Higel
*Attorney, Agent, or Firm*—Catharine D. Fitch; Melvin Winokur

[57] ABSTRACT

Compounds of the formula

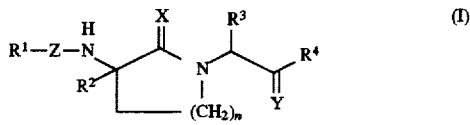

are inhibitors of peptide binding to major histocompatibility complex type II proteins and are useful in the treatment and prevention of autoimmune diseases including: rheumatoid arthritis, Type I diabetes, multiple sclerosis, lupus erythematosis, Graves disease and pemphigus. The present invention also provides novel compositions, methods of treatment employing the compounds of the present invention and methods of manufacture of the compounds of structural formula (I).

9 Claims, No Drawings

OTHER PUBLICATIONS

Acton III et al., Tetra. Lett., vol. 37, No. 25, pp. 4319–4322 (1996), "Synthesis and derivatization of a versatile alpha-substituted lactam dipeptide isostere".

Acton III et al., C&EN, Feb. 19, 1996, 211th ACS Nat'l Meeting, New Orleans, Mar. 24–28, 1996, "alpha–Allyl lactam dipeptide isosteres: Synthesis and utility of a versatile intermediate".

Rusiecki et al., Abstracts of the 20th IUPAC Symposium on the Chemistry of Natural Products, Chicago, IL, Sep. 15–20, 1996, "Modular synthesis of tripeptide inhibitors of MHC Class II".

Kroemer et al., J. Med. Chem., vol. 38 (1995), pp. 4917–4928, "3D–Quantitative structure–activity relationships of human immunodeficiency virus type–1 proteinase . . .".

Scholz et al., J. Med. Chem., vol. 37 (1994), pp. 3079–3089, "Inhibitors of HIV–1 proteinase containing 2–heterosubstituted 4–amino–3–hydroxy–5–phenylpentanoic acid . . .".

Chapman et al., J. Med. Chem., vol. 36 (1993), pp. 4293–4301, "Inhibition of matrix metalloproteinases by N–carboxyalkyl peptides".

Urban et al. FEBS, vol. 298, No. 1 (1992), pp. 9–13, "Reduced–bond tight–binding inhibitors of HIV–1 protease".

PSEUDOPEPTIDE LACTAM INHIBITORS OF PEPTIDE BINDING TO MHC CLASS II PROTEINS

This application claims the benefit of U.S. Provisional application No. 60/008,060, filed Oct. 30, 1995.

FIELD OF THE INVENTION

The present invention provides novel compounds, novel compositions, methods of their use and methods of their manufacture, where such compounds are generally pharmacologically useful as agents in therapies whose mechanism of action rely on the inhibition of peptide binding to major histocompatibility complex (MHC) class II molecules, and more particularly useful in therapies for the treatment and prevention of autoimmune diseases.

BACKGROUND OF THE INVENTION

A basic function of the immune system is to distinguish self from non-serf, an activity carried out primarily by T cells. Failure of mechanisms which control the tolerance of T cells to self antigens and the prevention of activation of T cells by self antigens may lead to autoimmunity. In individuals afflicted with autoimmune diseases, an increased frequency of alleles for specific human leukocyte antigens (HLAs) are found, and it is believed that the disease-associated HLA molecules have the ability to bind the autoantigen and present it to T cells, thereby inducing and/or maintaining the autoimmune process. Currently available immunosuppressive drugs are inadequate for autoimmune disease therapy because of limited efficacy, lack of selectivity and considerable toxicity.

The present invention is directed to compounds which inhibit the binding of peptides to the major histocompatibility complex class II, a more selective target for therapeutic treatment and prevention of autoimmune diseases.

Major histocompatibility complex class II molecules (MHC class II) are cell-surface glycoproteins that bind antigenic peptide fragments and display them at the cell surface to CD4-positive helper T-cells. The action of these molecules forms part of a pathway of the immune system for identifying and responding to foreign antigens. In brief, antigen presenting cells internalize foreign proteins. Once internalized, the proteins are proteolytically degraded and short sequences of the degraded proteins are bound to MHC class II molecules in an endosomal compartment. These complexes of the short sequences bound to the MHC Class II molecule are then exposed on the cell surface where they initiate a series of immunogenic events.

MHC Class II proteins are synthesized and assembled in the endoplasmic reticulum as trimers composed of highly polymorphic α and β-chain polypeptides and a non-polymorphic invariant chain polypeptide. The invariant chain prevents the premature binding of peptides to MHC class II. In addition, the invariant chain contains a sequence that targets the α/β heterodimer into the low pH, protease-rich endosomal compartment. In this compartment, the invariant chain is removed, leaving the MHC class II α/β heterodimers free to bind antigenic peptides.

Both class I and class II histocompatibility proteins have different domain organizations but similar structures, with two membrane-proximal immunoglobulin-like domains and a membrane-distal peptide-binding site formed by an eight stranded β-sheet and two α-helical regions. Polymorphic residues in both class I and II proteins are clustered in the peptide-binding region and are responsible for the different peptide specificities observed for different histocompatibility proteins. Class I histocompatibility proteins are specific for peptides of defined length, usually 8–10 residues and have allele-specific binding motifs characterized by strong preferences for a few side chains at some positions in the peptide, and wide tolerance for many side chains at the other positions. Class II histocompatibility proteins bind longer peptides with no apparent restriction on peptide length. Class II proteins also have allele specific motifs, which have been more difficult to characterize because of the difficulty in aligning peptide sequences of different lengths.

The mechanism of peptide binding to class II histocompatibility proteins has not been clearly defined. The 3.3 angstrom crystal structure of the human class II histocompatibility protein HLA-DR1 showed that bound peptide extended out the ends of the binding site, but interpretation of HLA-peptide interactions was complicated by the presence of a mixture of endogenous peptides in the peptide-binding site. Brown et at., Nature 364:33–39 (1993).

Stem et al. determined the refined 2.75 angstrom structure of the HLA-DR1/HA peptide complex showing that the peptide binds as a straight extended chain with a pronounced twist. Nature 368:215–221 (1994). Hydrogen bonds between main-chain atoms along the peptide and HLA-DR1 residues from the α-helical regions and the β-sheet provide a component to the binding interaction that is independent of peptide sequence. Twelve of the hydrogen bonds involve residues conserved in most human and mouse class II alleles, and suggest a universal method for peptide binding by class II histocompatibility proteins. Five side chains of the HA peptide are accommodated by polymorphic pockets in the HLA-DR1 binding site. These pockets appear to determine the peptide specificity of different class II proteins.

Antigen presenting cells (APCs) expressing MHC class II molecules capture proteins from extracellular fluids. APCs can take up antigens through surface immunoglobulin receptors, through $F_c$ receptor-mediated internalization of antibody/antigen complexes, or through bulk-phase endocytosis. Internalized antigens are then transported to endosomal compartments where they are digested into peptide fragments. A subset of these peptides can associate with a specific binding groove at the interface of MHC class II α and β-chain heterodimers. Most of the polymorphisms in these proteins are located within this binding groove, so that each different MHC class II allele can bind a distinct, but overlapping, subset of antigenic peptides. MHC class II/peptide complexes are then transported to the cell surface where they are recognized by T-cell receptors (TCRs) on CD4-positive T-cells. This process is pivotal for the generation of both humoral and cellular immune responses.

Three genetic loci within the human MHC encode class II antigen-presenting molecules: HLA-DP, HLA-DQ, and HLA-DR. These loci are highly polymorphic. For instance, there are over 30 DRβ alleles in the human population. Since each individual expresses only a small number of different histocompatibility proteins, each histocompatibility protein must be able to bind a large number of different peptides in order to ensure an immune response against many possible pathogens. The extensive polymorphism of histocompatibility genes may be the result of selection of alleles that can present peptides from particular pathogens.

The inheritance of particular MHC class II alleles is linked to susceptibility to many autoimmune diseases. A prominent example of this is susceptibility to rheumatoid arthritis (RA) which is genetically associated with a small subset of related DR alleles (DR4Dw4, DR4Dw14, and DR1). See, Skinner et at., Annals of the Rheumatic Diseases 53:171–177 (1994). Over 90% of RA patients possess at least one of these 3 DR alleles compared to 27% in an age-matched control group.

Autoimmune conditions are thought to involve the T-cell recognition of self-components by MHC Class II proteins, a situation which is normally avoided. This presentation generates an undesirable immune response to self. Since the function of MHC class II molecules is to present peptide antigens, the present invention is concerned with compounds which interfere with the binding of peptides to MHC class II molecules and a method of treating and preventing autoimmune diseases employing such compounds which interfere with the binding of peptides to MHC class II molecules associated with disease. Specifically blocking the formation of the MHC Class II/self-peptide complex is a manner of disrupting the aberrant process of the autoimmune disorder without globally depressing immune function. Hurtenbach et al., J. Exp. Med. 177:1499–1504 (1993) demonstrated that treatment with MHC class II complex-blocking peptide prevented autoimmune diabetes in non-obese diabetic mice. Further, Guery et al., J. Exp. Med. 177:1461–1468 (1993) administered MHC class II binding peptides to mice and showed suppression of induction of T cell mediated antibody responses. The binding inhibitors of the present invention may prevent the presentation of self-peptides to autoreactive T-cells that drive the disease process. An advantage of the immunotherapy and immunotherapeutic agents of the present invention is that they are very selective agents, targeting only certain alleles of MHC Class II, which may minimize the risk of opportunistic infections during long term treatment. Although competition for MHC binding among peptides is known, no non-peptide (or pseudopeptide) inhibitor of MHC Class II binding is known. Due to the inherent pharmacological limitations of peptides, particularly within a system that involves proteolytic degradation of proteins, the compounds of the present invention having less peptidic character may present a useful avenue for therapy.

SUMMARY OF THE INVENTION

The novel compounds of this invention are those of structural formula I:

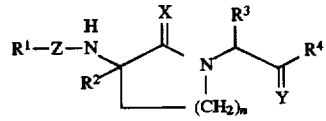

or a pharmaceutically acceptable salt or ester thereof, that inhibit peptide binding to MHC Class II proteins. As inhibitors of binding to MHC Class II proteins, the compounds of the present invention may be used in the treatment and prevention of autoimmune diseases, including rheumatoid arthritis, Type I diabetes, multiple sclerosis, lupus erythematosis, Graves disease and pemphigus.

There is no precedent in the literature for inhibition of MHC Class II proteins by nonpeptides or pseudopeptides.

Therefore it is an object of this invention to provide compounds that have activity in the inhibition of peptide binding to MHC Class II proteins. It is an additional object of this invention to provide methods of using the compounds of formula I for the treatment of autoimmune conditions such as rheumatoid arthritis, Type I diabetes, multiple sclerosis, lupus erythematosis, Graves disease and pemphigus. It is a further object of this invention to provide pharmaceutical compositions for the compounds of formula I. Still another object of the present invention is to provide a method for in vitro inhibition of peptide binding of MHC Class II proteins.

DETAILED DESCRIPTION OF THE INVENTION

The novel compounds of this invention have the general structural formula I:

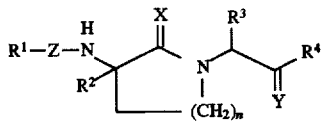

or a pharmaceutically acceptable salt or ester thereof wherein:

Z is selected from:
  (a) $CHR^5$,
  (b) —C(O)—,
  (c) $SO_2$, and
  (d) —C(O)—O—;

X is selected from:
  (a) O, and
  (b) S;

Y is selected from:
  (a) O,
  (b) H,H, and
  (c) $CHR^6$;

$R^1$ is selected from
  (a) $C_{1-10}$ alkyl, unsubstituted or substituted with one to three substituents selected from:
    (1) aryl,
    (2) cycloalkyl,
    (3) halogen,
    (4) $NHR^7$, and
    (5) a heterocyclic ring,
  (b) $C_{2-10}$ alkenyl, unsubstituted or substituted with one to three substituents selected from:
    (1) $C_{1-5}$alkyl,
    (2) aryl,
    (3) cycloalkyl,
    (4) halogen,
    (5) $NHR^7$, and
    (6) a heterocyclic ring,
  (c) cycloalkyl, and
  (d) a heterocylic ring;

$R^2$ is $C_{1-5}$ alkyl or $C_{2-5}$ alkenyl, unsubstituted or substituted with one to three substituents selected from:
  (a) cycloalkyl,
  (b) aryl,
  (c) OH,
  (d) $NH_2$,
  (e) —NHCH=NH($NH_2$),
  (f) —NHCO—aryl, and
  (g) halogen;

$R^3$ is $C_{1-5}$ alkyl, unsubstituted or substituted with one to three substituents selected from:
  (a) cycloalkyl,
  (b) aryl,
  (c) OH,
  (d) $NH_2$, and
  (e) halogen;

$R^4$ selected from:
  (a) H,
  (b) $NHNR^6R^6$, and (c) NHCHR$^6$R$^6$;

R$^5$ is selected from C$_{1-3}$ alkyl and H;

R$^6$ is selected from:
(a) C$_{1-8}$ alkyl, unsubstituted or substituted with one to three substituents selected from:
(1) —CONHR$^5$,
(2) —COOR$^5$,
(3) —COOH,
(4) OH,
(5) C$_{1-5}$alkoxy, and
(6) NH$_2$,
(b) H,
(c) —CONHR$^5$,
(d) —COOR$^5$, and
(e) —COOH;

R$^7$ is selected from:
(a) C$_{1-4}$ alkyl,
(b) C$_{1-4}$ alkoxycarbonyl,
(c) C$_{1-4}$ acyl, and
(d) C$_{1-4}$ sulfonyl;

n is an integer between 1 and 4;

cycloalkyl is selected from:
(a) C$_{3-8}$ saturated cyclo alkyl, unsubstituted or substituted with one to three substituents selected from:
(1) C$_{1-4}$ alkyl,
(2) C$_{1-4}$ alkoxy,
(3) halogen, and
(4) hydroxy,
(b) C$_{3-8}$ saturated cycloalkyl substituted with aryl or C$_{3-8}$ cycloalkyl, and
(c) C$_{3-8}$ saturated cycloalkyl fused with aryl or C$_{3-8}$ cycloalkyl;

aryl is selected from:
(a) phenyl,
(b) naphthyl,
(c) indenyl,
(d) thiophenyl,
(e) benzothiophenyl,
(f) furanyl,
(g) benzofuranyl,
(h) pyrollyl,
(i) indolyl, and
(j) pyridyl;
wherein the aryl group may be unsubstituted or substituted with one to three substituents selected from:
(1) C$_{1-4}$ alkyl,
(2) C$_{1-4}$ alkoxy,
(3) halogen, and
(4) hydroxy;

a heterocyclic ring is selected from:
(a) C$_{3-8}$ cycloalkyl wherein one or two of the carbon atoms are replaced with a heteroatom selected from oxygen, nitrogen and sulfur, unsubstituted or substituted with one to three substituents selected from:
(1) C$_{1-4}$ alkyl,
(2) C$_{1-4}$ alkoxy,
(3) halogen, and
(4) hydroxy;
(b) C$_{3-8}$ saturated cycloalkyl wherein one or two of the carbon atoms are replaced with a heteroatom selected from oxygen, nitrogen and sulfur, substituted with aryl or C$_{3-8}$ cycloalkyl, and
(c) C$_{3-8}$ saturated cycloalkyl wherein one or two of the carbon atoms are replaced with a heteroatom selected from oxygen, nitrogen and sulfur, fused with aryl or C$_{3-8}$ cycloalkyl.

As used herein "alkyl" is intended to include both branched- and straight-chain saturated aliphatic hydrocarbon groups having the specified number of carbon atoms, e.g. methyl, ethyl, propyl, butyl, pentyl, hexyl, heptyl, octyl, nonyl, decyl and isomers thereof such as isopropyl, isobutyl, sec-butyl, tert-butyl, isopentyl, isohexyl, etc. "Alkoxy" represents an alkyl group having the indicated number of carbon atoms attached through an oxygen bridge, e.g. methoxy, ethoxy, propyloxy, isopropoxy, etc. "Alkoxycarbonyl" represents a group of the form alkyl—O—C(O)— wherein the indicated number of carbon atoms refers to those of the alkyl residue. "Acyl" represents an alkyl group having the indicated number of carbon atoms attached through a —C(O)— bridge. "Sulfonyl" represents an alkyl group having the indicated number of carbon atoms attached through a —SO$_2$-bridge.

The terms halogen and halo refer to F, Cl, Br and I.

The heterocyclic or aryl ring may be attached to the structural formula I at any nitrogen (in the case of heterocyclic) or carbon atom (in either case) in the ring which results in the creation of a stable, uncharged structure.

Combinations of substituents and/or variables are permissible only if such combinations result in stable compounds.

In one embodiment of the instant invention are compounds of formula I wherein:

Z is CHR$^5$;
X is O;
Y is O;
R$^1$ is selected from
(a) C$_{1-10}$ alkyl, unsubstituted or substituted with one to three substituents selected from:
(1) aryl,
(2) cycloalkyl, and
(b) cycloalkyl;

R$^2$ is C$_{1-5}$ alkyl, unsubstituted or substituted with:
(a) NH$_2$,
(b) NHCH═NH(NH$_2$), and
(c) aryl;

R$^3$ is C$_{1-5}$ alkyl;

R$^4$ selected from:
(a) NHNR$^6$R$^6$, and
(b) NHCHR$^6$R$^6$;

R$^5$ is selected from C$_{1-3}$ alkyl and H;

R$^6$ is selected from:
(a) C$_{1-8}$ alkyl,
(b) —CONHR$^5$,
(c) —COOR$^5$, and n has a value of 1 or 2.

Examples of compounds within this class include, but are not limited to, the following:

EtOCO-Phe-(R)-γ-Lactam-Nva-Leu-NH$_2$, (9),

EtOCO-Cha-(R)-γ-Lactam-Nva-Leu-NH$_2$, (10), cHx(CH$_2$)$_3$-(R)-γ-Lactam-Nva-Leu-NH$_2$, (11), EtOCO-Pheψ(CH$_2$NH)-(R)-γ-Lactam-Nva-Leu-NH$_2$, (14), Ph(CH$_2$)$_3$-(R)-γ-Lactam-Nva-Leu-NH$_2$, (15), EtOCO-Chaψ(CH$_2$NH)-(R)-γ-Lactam-Nva-Leu-NH$_2$, (18), Ph(CH═CHCH$_2$)-(R)-γ-Lactam-Nva-Leu-NH$_2$, (19), Ph(C(CH$_3$)═CHCH$_2$NH)-(R)-γ-Lactam-Nva-Leu-NH$_2$, (20), cHx(CH═C(CH$_3$)CH$_2$)-(R)-γ-Lactam-Nva-Leu-NH$_2$, (21), cHx(CH$_2$C(CH$_3$)CH$_2$)-(R)-γ-Lactam-Nva-Leu-NH$_2$, (22), cHx((CH₃)C=CHCH₂)-(R)-γ-Lactam-Nva-Leu-NH₂, (23),
cHx((CH₃)CHCH₂CH₂NH)-(R)-γ-Lactam-Nva-Leu-NH₂, (24),
cHp(CH=CHCH₂)-(R)-γ-Lactam-Nva-Leu-NH₂, (25),
cHp(CH₂)₃-(R)-γ-Lactam-Nva-Leu-NH₂, (26),
cOct(CH=CHCH₂)-(R)-γ-Lactam-Nva-Leu-NH₂, (27),
cOct(CH₂)₃-(R)-γ-Lactam-Nva-Leu-NH₂, (28),
cPn(CH₂)₃-(R)-7-Lactam-Nva-Leu-NH₂, (29),
cHx(CH₂)₃-(R)-γ-Lactam-Nva-(α-aza)-Leu-NH₂, (32),
cHx(CH₂)₃HN-(R)-γ-Lactam-Nva-Leu-OBn, (36),
cHx(CH₂)₃-(R)-γ-Lactam-Nva-Leu-OH, (37),
EtOCO-Phe-(S)-γ-Lactam-Nva-Leu-NH₂, (44),
EtOCO-Cha-(S)-γ-Lactam-Nva-Leu-NH₂, (45),
cHx(CH₂)₃-(S)-γ-Lactam-Nva-Leu-NH₂, (46),
EtOCO-Phe-(R)-δ-Lactam-L-Nva-Leu-NH₂, (51),
EtOCO-Phe-(R)-δ-Lactam-D-Nva-Leu-NH₂, (52),
EtOCO-Cha-(R)-δ-Lactam-L-Nva-Leu-NH₂, (53),
EtOCO-Cha-(R)-δ-Lactam-D-Nva-Leu-NH₂, (54),
cHx(CH₂)₃-(R)-δ-Lactam-D,L-Nva-Leu-NH₂, (55),
EtOCO-Phe-(S)-δ-Lactam-L-Nva-Leu-NH₂, (61),
EtOCO-Phe-(S)-δ-Lactam-D-Nva-Leu-NH₂, (62),
EtOCO-Cha-(S)-δ-Lactam-L-Nva-Leu-NH₂, (63),
EtOCO-Cha-(S)-δ-Lactam-D-Nva-Leu-NH₂, (64),
cHx(CH₂)₃-(S)-δ-Lactam-L-Nva-Leu-NH₂, (65),
cHx(CH₂)₃-(S)-δ-Lactam-D-Nva-Leu-NH₂, (66),
cHx(CH₂)₃-α-Propyl-(R)-γ-Lactam-Nva-Leu-NH₂, (76),
cHPCH=CHCH₂-α-Propyl-(R)-γ-Lactam-Nva-Leu-NH₂, (77),
cHP(CH₂)₃-α-Propyl-(R)-γ-Lactam-Nva-Leu-NH₂, (78),
cHx(CH₂)₃-α-(3-Hydroxypropyl)-(R)-γ-Lactam-Nva-Leu-NH₂, (81),
cHx(CH₂)₃-α-Propyl-(S)-γ-Lactam-Nva-Leu-NH₂, (84),
cHx(CH₂)₃-α-propyl-(R)-γ-Lactam-Nva-NHNBu(COOEt), (93),
cHPCH=CHCH₂-α-propyl-(R)-γ-Lactam-Nva-NHNBu(COOEt), (94),
cHP(CH₂)₃-α-propyl-(R)-γ-Lactam-Nva-NHNBu(COOEt), (95),
Boc-Chaψ(CH₂HN)-α-Propyl-(R)-γ-Lactam-Nva-NHNBu(COOEt), (96),
HCl.H₂N-Chaψ(CH₂HN)-α-propyl-(R)-γ-Lactam-Nva-NHNBu(COOEt), (97),
MeSO₂-Chaψ(CH₂HN)-α-Propyl-(R)-γ-Lactam-Nva-NHNBu(COOEt),(98),
Pr-Chaψ(CH₂HN)-α-Propyl-(R)-γ-Lactam-Nva-NHNBu(COOEt), (99),
Ac-Chaψ(CH₂HN)-α-Propyl-(R)-γ-Lactam-Nva-NHNBu(COOEt), (100),
Boc-D-Chaψ(CH₂HN)-α-Propyl-(R)-γ-Lactam-Nva-NHNBu(COOEt),
HCl.H₂N-D-Chaψ(CH₂HN)-α-propyl-(R)-γ-Lactam-Nva-NHNBu(COOEt),
MeSO₂-D-Chaψ(CH₂HN)-α-Propyl-(R)-γ-Lactam-Nva-NHNBu(COOEt),
Ac-D-Chaψ(CH₂HN)-α-Propyl-(R)-γ-Lactam-Nva-NHNBu(COOEt),
Ph(CH₂)₂SO₂-(R)-γ-Lactam-Nva-Leu-NH₂,
Cbz-(R)-γ-Lactam-Nva-Leu-NH₂,
Boc-(R)-γ-Lactam-Nva-CH=CHCO₂Et,
cHx(CH₂)₃-(R)-γ-Lactam-Nvaψ(CH₂NH)Leu-NH₂,
cHx(CH₂)₃-(R)-γ-Thiolactam-Nva-Leu-NH₂,
(CH₃)₂CCH(CH₂)₂CH(CH₃)CH₂-(R)-γ-Lactam-Nva-Leu-NH₂,
cHxCH(CH₂)CHCH₂-(R)-γ-Lactam-Nva-Leu-NH₂,
[4H]-Naphthyl-CH₂-(R)-γ-Lactam -Nva-Leu-NH₂,
cHx(CH₂)₃-α-(3-Hydroxypropyl)-(R)-γ-Lactam-Nva-NHNBu(COOEt),
cHx(CH₂)₃-α-(3-Azidopropyl)-(R)-γ-Lactam-Nva-NHNBu(COOEt),
cHx(CH₂)₃-α-(3-Aminopropyl)-(R)-γ-Lactam-Nva-NHNBu(COOEt),
cHx(CH₂)₃-α-(3-guanidinopropyl)-(R)-γ-Lactam-Nva-NHNBu(COOEt),
cHx(CH₂)₃-(R)-γ-Lactam- Nva-( a- aza )-Leu-OEt,
cHx(CH₂)₃-(R)-γ-Lactam-Nva-NHNBu(COOEt),
cHx (CH₂)₃-(R)-γ-Lactam-Nva-NHN(2-methylbutyl)(COOEt),
cHx(CH₂)₃-(R)-γ-Lactam-Nva-NHN(3-methylbutyl)(COOEt),
cHx(CH₂)₃-(R)-γ-Lactam-Nva-NHNiBu(COOEt),
cHx(CH₂)₃-(R)-γ-Lactam-Nva-NHN(cyclohexylmethyl)(COOEt),
cHx(CH₂)₃-(R)-γ-Lactam-Nva-NHNBu₂,
cHx(CH₂)₃-(R)-γ-Lactam-Nva-NHNBu(SO₂Me),
[4H]-naphthylmethyl-(R)-γ-Lactam-Nva-NHNBu(COOEt),
[10H]-naphthylmethyl-(R)-γ-Lactam-Nva-NHNBu(COOEt),
[8H]-indenylethyl-(R)-γ-Lactam-Nva-NHNBu(COOEt),
[10H]-naphthylmethyl-α-(3-guanidinopropyl)(R)-γ-Lactam-Nva-NHNBu(COOEt),
[10H]-naphthylmethyl-α-(3-Hydroxypropyl)-(R)-γ-Lactam-Nva-NHNBu(COOEt),
[10H]-naphthylmethyl-α-(3-Azidopropyl)-(R)-γ-Lactam-Nva-NHNBu(COOEt), and
[10H]-naphthylmethyl-α-(3-Aminopropyl)-(R)-γ-Lactam-Nva-NHNBu(COOEt).

Examples of compounds within this class include, but are not limited to, the following:
cHx(CH₂)₃-(R)-γ-Lactam-Nva-Leu-NH₂, (11)
Ph(CH₂)₃-(R)-γ-Lactam-Nva-Leu-NH₂, (15)
Ph(CH=CHCH₂)-(R)-γ-Lactam-Nva-Leu-NH₂, (19)
Ph(C(CH₃)=CHCH₂NH)-(R)-γ-Lactam-Nva-Leu-NH₂, (20)
cHx(CH=C(CH₃)CH₂)-(R)-γ-Lactam-Nva-Leu-NH₂, (21)
cHx(CH₂C(CH₃)CH₂)-(R)-γ-Lactam-Nva-Leu-NH₂, (22)
cHx((CH₃)C=CHCH₂)-(R)-γ-Lactam-Nva-Leu-NH₂, (23)
cHx((CH₃)CHCH₂CH₂NH)-(R)-γ-Lactam-Nva-Leu-NH₂, (24)
cHp(CH=CHCH₂)-(R)-γ-Lactam-Nva-Leu-NH₂, (25)
cHp(CH₂)₃-(R)-γ-Lactam-Nva-Leu-NH₂, (26)
cOct(CH=CHCH₂)-(R)-γ-Lactam-Nva-Leu-NH₂, (27)
cOct(CH₂)₃-(R)-γ-Lactam-Nva-Leu-NH₂, (28)
cPn(CH₂)₃-(R)-γ-Lactam-Nva-Leu-NH₂, (29)
cHx(CH₂)₃-(R)-γ-Lactam-Nva-α-aza-Leu-NH₂, (32)
cHx(CH₂)₃-α-Propyl-(R)-γ-Lactam-Nva-Leu-NH₂, (76)

cHPCH=CHCH₂-α-Propyl-(R)-γ-Lactam-Nva-Leu-NH₂, (77)

cHP(CH₂)₃-α-Propyl-(R)-γ-Lactam-Nva-Leu-NH₂, (78)

cHx(CH₂)₃-α-(3-Hydroxypropyl)-(R)-γ-Lactam-Nva-Leu-NH₂, (81)

cHx(CH₂)₃-α-Propyl-(R)-γ-Lactam-Nva-NHNBu(COOEt), (93)

cHPCH=CHCH₂-α-propyl-(R)-γ-Lactam-Nva-NHNBu(COOEt), (94)

cHP(CH₂)₃-α-Propyl-(R)-γ-Lactam-Nva-NHNBu(COOEt), (95)

cHxCH(CH₂)CHCH₂-(R)-γ-Lactam-Nva-Leu-NH₂,

[4H]-Naphthyl-CH₂-(R)-γ-Lactam-Nva-Leu-NH₂, cHx(CH₂)₃-α-(3-Hydroxypropyl)-(R)-γ-Lactam-Nva-NHNBu(COOEt), cHx(CH₂)₃-α-(3-Azidopropyl)-(R)-γ-Lactam-Nva-NHNBu(COOEt), cHx(CH₂)₃-α-(3-Aminopropyl)-(R)-γ-Lactam-Nva-NHNBu(COOEt), cHx(CH₂)₃-α-(3-guanidinopropyl)-(R)-γ-Lactam-Nva-NHNBu(COOEt), cHx(CH₂)₃-(R)-γ-Lactam-Nva-(α-aza)-Leu-OEt, cHx(CH₂)₃-(R)-γ-Lactam-Nva-NHNBu(COOMe), cHx(CH₂)₃-(R)-γ-Lactam-Nva-NHN(2-methylbutyl)(COOEt), cHx(CH₂)₃-(R)-γ-Lactam-Nva-NHN (3-methylbutyl)(COOEt), cHx(CH₂)₃-(R)-γ-Lactam-Nva-NHNiBu(COOEt), cHx(CH₂)₃-(R)-γ-Lactam-Nva-NHN(cyclohexylmethyl)(COOEt), cHx(CH₂)₃-(R)-γ- Lactam-Nva-NHNBu₂, cHx(CH₂)₃-(R)-γ-Lactam-Nva-NHNBu(SO₂Me),

[4H]-naphthylmethyl-(R)-γ-Lactam-Nva-NHNBu(COOEt),

[10H]-naphthylmethyl-(R)-γ-Lactam-Nva-NHNBu(COOEt),

[8H]-indenylethyl-(R)-γ-Lactam-Nva-NHNBu(COOEt),

[10H]-naphthylmethyl-α-(3-guanidinopropyl)(R)-γ-Lactam-Nva-NHNBu(COOEt),

[10H]-naphthylmethyl-α-(3-Hydroxypropyl)-(R)-γ-Lactam-Nva-NHNBu(COOEt),

[10H]-naphthylmethyl-α-(3-Azidopropyl)-(R)-γ-Lactam-Nva-NHNBu(COOEt), and

[10H]-naphthylmethyl-α-(3-Aminopropyl)-(R)-γ-Lactam-Nva-NHNBu(COOEt).

The compounds of the present invention are named by reference to a tetrapeptide of the general format:

cap-P1-P2-P3-P4 where "PX" represents the amino acid in the "xth" position in the tetrapeptide starting from P1 at the N-terminus. The 'cap' is a non-amino acid group attached to the N-terminus. P4 is the carboxy terminal residue. Names are given in the general form: amino terminus 'cap', followed by a hyphen and the three letter code of the first residue, followed by a hyphen and the three letter code of the second residue, followed by a hyphen and the three letter code of the third residue, followed by a hyphen and the three letter code of the fourth residue (three letter code is standard peptide nomenclature: see Amino Acid and Peptide Nomenclature *J. Biol. Chem* 260, 14–42 and IUPAC-IUB Nomenclature recommendations). Where any portion of the putative tetrapeptide is replaced by a non-peptide the residue (or residues) is replaced by a one line alphanumeric description constructed from IUPAC nomenclature and/or accepted abbreviations. For example, where 'cap-P1' is replaced by a 3-cyclohexylpropyl residue the name is of the format cHx (CH₂)₃-P2-P3-P4. After the last amino acid residue, or replacement, a hyphen is followed by the moiety positioned at the carboxy terminus of the analogous tetrapeptide, i.e. —NH2, —OH, —OEt. Unnatural amino acids are referred to by accepted nomenclature.

Examples of generally accepted abbreviations employed are:

| Name | Abbreviation(s) |
|---|---|
| Alkyl groups | Et, Pr, Bu, iBu . . . etc |
| Benzoyl | Bz |
| Benzyl | Bzl |
| Benzyloxycarbonyl | Cbz or Z |
| t-Butoxycarbonyl | Boc |
| Ethoxycarbonyl | EtOCO |
| Cyclohexyl | cHx |
| Cyclopentyl | cPe |
| Cyclohexylalanine | Cha |
| Norleucine | Nle |
| Norvaline | Nva |
| Xaa | Any amino acid |

Semicarbazide analogs of amino acids wherein the α-CH is replaced by a N-atom are written α-AzaXaa. Similar analogs not corresponding a commonly named amino acids are denoted by an alphanumeric string.

Examples are:

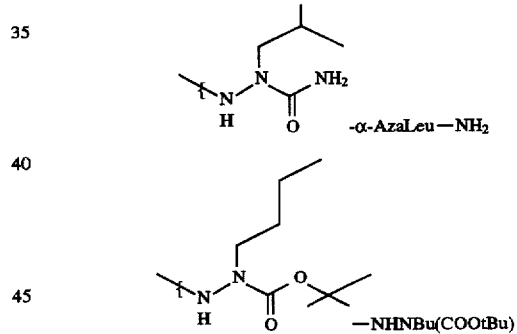

When dipeptide isosteres are employed in the structure in place of two amino acid residues, they are named in the format: 'first residueψ(descriptor of the —CONH— replacement)-second residue'

For example:

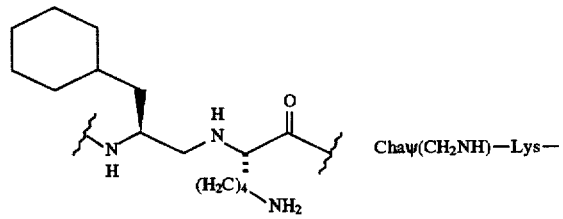

Lactam analogs are named as dipeptide units. R or S is used to designate the stereochemistry at the lactam α-center. γ or δ are used to designate lactam ring size in accord with normal usage. Substitution at the lactam α-center other than H is designated by a preceding 'α-substituent' descriptor. For example:

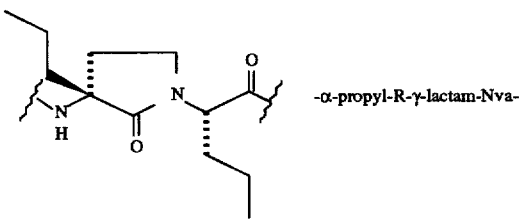

-α-propyl-R-γ-lactam-Nva-

The compounds of the present invention are of substantially non-peptide character, yet inhibit peptide binding MHC Class II proteins. Because the compounds of the present invention have substantially reduced peptide character relative to known inhibitors, the compounds of the present invention will be more likely to penetrate cellular membranes to access the Class II loading compartment within the cell, where competition for peptide binding is thought to occur. They are also likely to be more stable than peptides in the proteolytic environment of the endosomal compartment and hence better able to compete with the endogenous peptides. Based on knowledge within the art regarding peptide versus nonpeptide pharmacology, the compounds of the present invention are expected to have better oral bioavailability and longer in vivo half life than intact peptides.

Also included within the scope of this invention are pharmaceutically acceptable salts of the compounds of formula I, where a basic or acidic group is present on the structure.

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, realate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, and tetramethylammonium hydroxide. These salts may be prepared by standard procedures, e.g. by reacting a free acid with a suitable organic or inorganic base. Where a basic group is present, such as amino, an acidic salt, i.e. hydrochloride, hydrobromide, acetate, pamoate, and the like, can be used as the dosage form.

Also, in the case of an acid (—COOH) or alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

When any variable (e.g., X, Y, $R^1$, etc.) occurs more than one time in any constituent or in formula I, its definition on each occurrence is independent of its definition at every other occurrence. Also, combinations of substituents and/or variables are permissible only if such combinations result in stable compounds.

The compounds of the present invention may have chiral centers other than those centers whose stereochemistry is depicted in formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solyates with water or common organic solvents. Such solvates are encompassed within the scope of this invention.

The term "therapeutically effective amount" means that amount of a drag or pharmaceutical agent that will elicit the biological or medical response of a tissue, system, animal or human that is being sought by a researcher, veterinarian, medical doctor or other clinician, which includes alleviation of the symptoms of the disorder being treated. The novel methods of treatment of this invention are for disorders known to those skilled in the art. The term "mammal" includes humans.

The present invention has the objective of providing methods of treating and preventing autoimmune diseases including: rheumatoid arthritis, Type I diabetes, multiple sclerosis, lupus erythematosis, Graves disease and pemphigus by oral, systemic, parenteral or topical administration of the novel compounds of formula I either alone or in combination with other agents useful in treating autoimmune diseases. For the treatment of rheumatoid arthritis such agents which may be used in combination with the novel compounds of structural formula (I) include, but are not limited to: aspirin; NSAIDs including fenoprofen, tolmetin, sulindac, meclofenamate, indomethacin, ibuprofen, naproxen, ketoprofen, piroxicam, flurbiprofen, and diclofenac; gold sodium thiomalate; aurothioglucose; auranofin; penicillamine; hydroxychloroquine; sulfasalazine, corticosteroids; methotrexate; azathioprine; and cyclophosphamide. For the treatment of type 1 diabetes such agents which may be used in combination with the novel compounds of structural formula (I) include, but are not limited to: insulin therapy. For the treatment of multiple sclerosis such agents which may be used in combination with the novel compounds of structural formula (I) include, but are not limited to: prednisone, dexamethazone, azathioprine, copolymer 1, cyclophosphamide, interferon, plasmapheresis, and baclofen. For the treatment of lupus erythematosis, such agents which may be used in combination with the novel compounds of structural formula (I) include, but are not limited to: antimalarials such as hydroxychloroquinine, chloroquine, and quinacrine; prednisone and methyl prenisolone; and cyclophosphamide. For the treatment of pemphigus, such agents which may be used in combination with the novel compounds of structural formula (I) include, but are not limited to: systemic corticosteroids, prednisone, methotrexate, cyclophosphamide and azathioprine.

The present invention also has the objective of providing suitable topical, oral, systemic and parenteral pharmaceutical formulations for use in the novel methods of treatment and prevention of the present invention. The term "treatment" is intended to include ameliorating the autoimmune symptoms and/or arresting the progression of an autoimmune disease in an individual known to be, or believed to be suffering from an autoimmune disease. The term "prevention" is intended to include ameliorating the underlying cause of an autoimmune condition in an individual who may not have begun to experience recognizable symptoms of an autoimmune condition, and arresting the progress of an autoimmune disease in a patient who has not begun to experience recognizable symptoms of an autoimmune condition. The term "administration of" or "administering a" compound should be understood to mean providing a compound of the invention or a prodrug of a compound of the invention to the individual in need of treatment. The compositions containing the present compounds as the active ingredient for use in the treatment of the above-noted conditions can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

The daily dosage of the products may be varied over a range from 0.01 to 1,000 mg per adult human/per day. For oral administration, the compositions are preferably provided in the form of tablets containing from 0.01 to 1,000 mg, preferably 0.01, 0.05, 0.1, 0.5, 1.0, 2.5, 5.0, 10.0, 15.0, 25.0, or 50.0 milligrams of the active ingredient for the symptomatic adjustment of the dosage to the patient to be treated. An effective amount of the drug is ordinarily supplied at a dosage level of from about 0.0002 mg./kg. to about 50 mg./kg. of body weight per day. The range is more particularly from about 0.001 mg./kg. to 7 mg./kg. of body weight per day.

Advantageously, compounds of the present invention may be administered in a single daily dose, or the total daily dosage may be administered in divided doses of two, three or four times daily. The compounds of the present invention may be used to prepare a medicament or agent useful for the treatment of autoimmune conditions selected from rheumatoid arthritis, Type I diabetes, multiple sclerosis, lupus erythematosis, Graves disease and pemphigus. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For the treatment and prevention of autoimmune diseases, the compounds of the present invention may be administered in a pharmaceutical composition comprising the active compound in combination with a pharmaceutically acceptable carrier adapted for topical administration. Topical pharmaceutical compositions may be, e.g., in the form of a solution, cream, ointment, gel, lotion, shampoo or aerosol formulation adapted for application to the skin. These topical pharmaceutical compositions containing the compounds of the present invention ordinarily include about 0.005% to 5% by weight of the active compound in admixture with a pharmaceutically acceptable vehicle.

For the treatment and prevention of autoimmune diseases, the compounds of the present invention may be used together with agents known to be useful in treating autoimmune disease, discussed previously.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carders (collectively referred to herein as "carder" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The compounds of the present invention can be prepared readily according to the following Schemes and Examples or modifications thereof using readily available starting materials, reagents and conventional synthesis procedures. In these reactions, it is also possible to make use of variants which are themselves known to those of ordinary skill in this art, but are not mentioned in greater detail.

The compounds of the present invention can be prepared readily according to the following Schemes and Examples or modifications thereof using readily available starting materials, reagents and conventional synthesis procedures. In these reactions, it is also possible to make use of variants which are themselves known to those of ordinary skill in this art, but are not mentioned in greater detail.

BACKGROUND FOR LACTAM SYNTHESIS

The compounds outlined here are receptor binding molecules intended to mimic amino terminus proximal residues of known biologically relevant peptide ligands. In general they are tetrapeptide mimics centered about a lactam core unit. The use of lactams as peptide backbone constraints is well documented. Their construction is intended to limit the available conformations of a pseudo-peptide such that the desired active conformation is more highly populated.[1] It would be expected that they would also serve to reduce the lability of the enclosed amide bond to the action of endogenous proteases. The synthesis of several types of lactam constraint have been reported including simple sidechain-to-backbone of varying ring size (A & B)[2], substituted sidechain-to-backbone (C)[3] and backbone-to-backbone (D)[4].

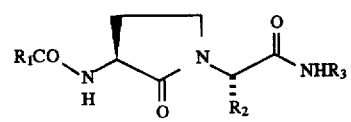

(A)

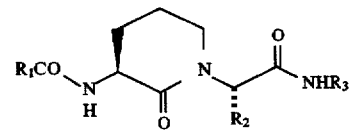

(B)

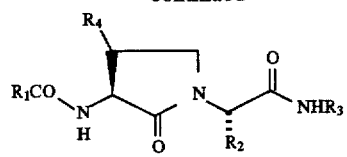

(C)

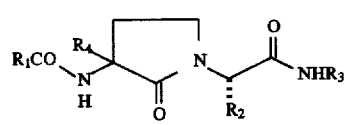

(D)

1. For a general review see Liskamp, R. M. J. Rec. Trav. Chim.Pays-Bas,1994, 113, 1.
2. For example see Freidinger, R. M. et al, J. Org. Chem. 1982, 47, 104.
3. For example see Garvey, D. S. J. Org. Chem. 1990, 55, 936.
4. For example see Zydowsky, T. M. et al J. Org. Chem. 1988, 53, 5607.

The general synthetic schemes draw on these and other known chemistries to build a lactam dipeptide mimetic that is then further elaborated to the final peptidomimetic. In the case of simple analogs (i.e. A or B above) the synthetic protocol for construction of the lactam is as reported.[2] This, along with an example of its extension to a tetrapeptide mimetic, is outlined in Scheme I.

Scheme I

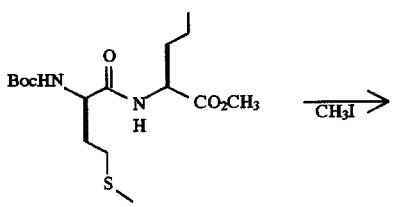

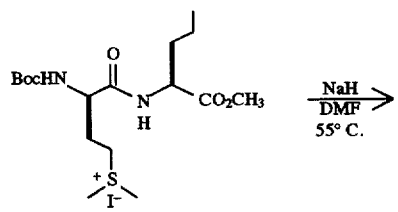

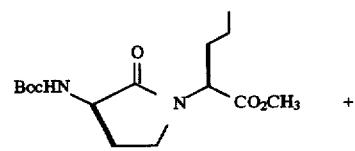

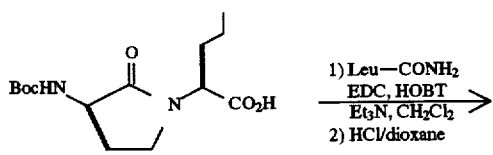

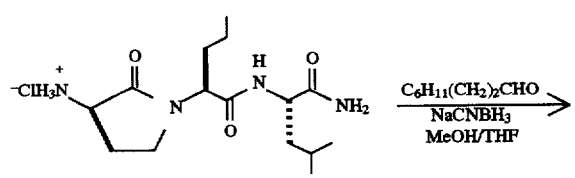

-continued
Scheme I

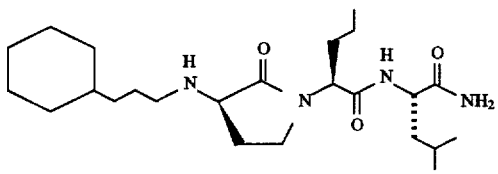

In the case of α-disubstituted lactams (i.e. D above), although individual procedures are precedented (for example, asymmetric alkylation of oxazolidinones[5] and similar sulphonium salt mediated ring closures[2,6]), the combination of synthetic steps employed (see Scheme II, which also shows an example of extension to a tetrapeptide mimetic) and the consequent ability to independently manipulate the lactam side chain ($R_4$ in 4 above) has not, to our knowledge, been reported. In some of these cases functionality in the lactam unit is manipulated subsequent to extension of the dipeptide mimetic.

5. Karady, S. et al, *Tetrahedron Lett.* 1984, 25, 4337.
6. Thaisrivongs, S. et al, *J.Med. Chem.* 1988, 31, 1369.

Scheme II

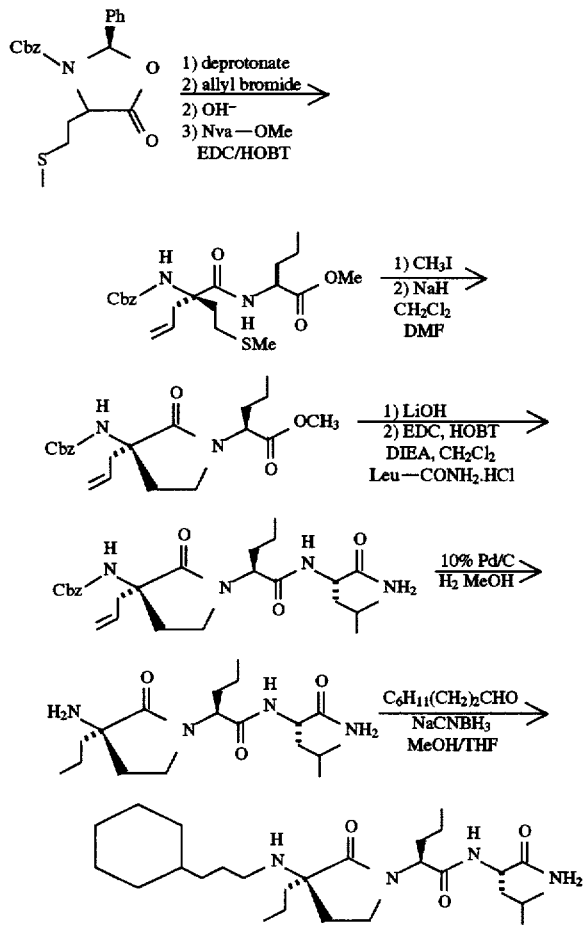

Scheme II outlines an optically defined approach wherein the final mimetic is produced with known absolute stereochemistry. It is also possible to generate the analogs using an optically uncontrolled route (e.g. Scheme III) wherein neither of the stereocenters of the lactam dipeptide mimic is a priori defined. Physical separation of all four possible diastereomers provides access to the required analogs.

Scheme III

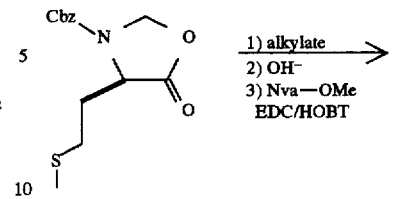

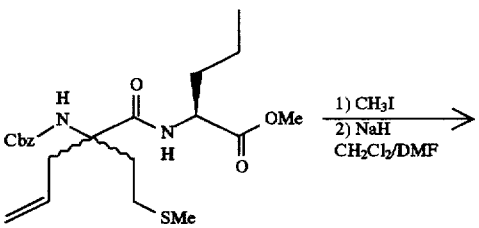

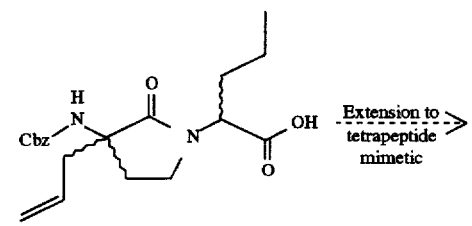

The following examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds.

GENERAL METHODS

All temperatures given in the following examples are in degrees Celsius. $^1$H nuclear magnetic resonance (NMR) spectra were taken at 300, 400 or 500 MHz at ambient temperature in the solvent indicated. Shifts are reported in ppm, referenced to solvent D. Except where indicated, commercially available compounds were used without further purification. Where not noted, natural and unnatural amino acids are of the (L) configuration. Various protected di- and tripeptides were prepared by conventional EDC/HOBT solution phase couplings of appropriately protected amino acids. Anhydrous solvents were purchased from Aldrich. $CH_2Cl_2$ was, in some cases, distilled from $CaH_2$ before use. All reactions run under anhydrous conditions were run under positive pressure of dry nitrogen.

Abbreviations used are as follows: Cha is cyclohexylalanine, Nva is norvaline, NMP is N-methylpyrollidine, DCC is dicyclohexylcarbodiimide, HOBT is hydroxybenzotriazole, BOP is benzotriazol-1-yloxy-tris(dimethylamino)phosphoniam hexafluorophosphate, DIEA is diisopropylethylamine, DMAP is 4-dimethylaminopyridine, TFA is trifluoroacetic acid, Fmoc is 9-fluorenylmethyloxycarbonyl, 9-BBN is 9-borabicyclod[3.3.1]nonane, DMF is dimethyl formamide, THF is THF, EDC is 1-(3-dimethylaminopropyl)-3-ethyl carbodimide hydrochloride, HPLC is high pressure liquid chromatography, RP-HPLC is reversed phase high pressure liquid chromatography, ESI is electrospray ionization, FAB is fast atom bombardment, CS is chemical ionization. TLC is SiO₂ thin layer chromatography.

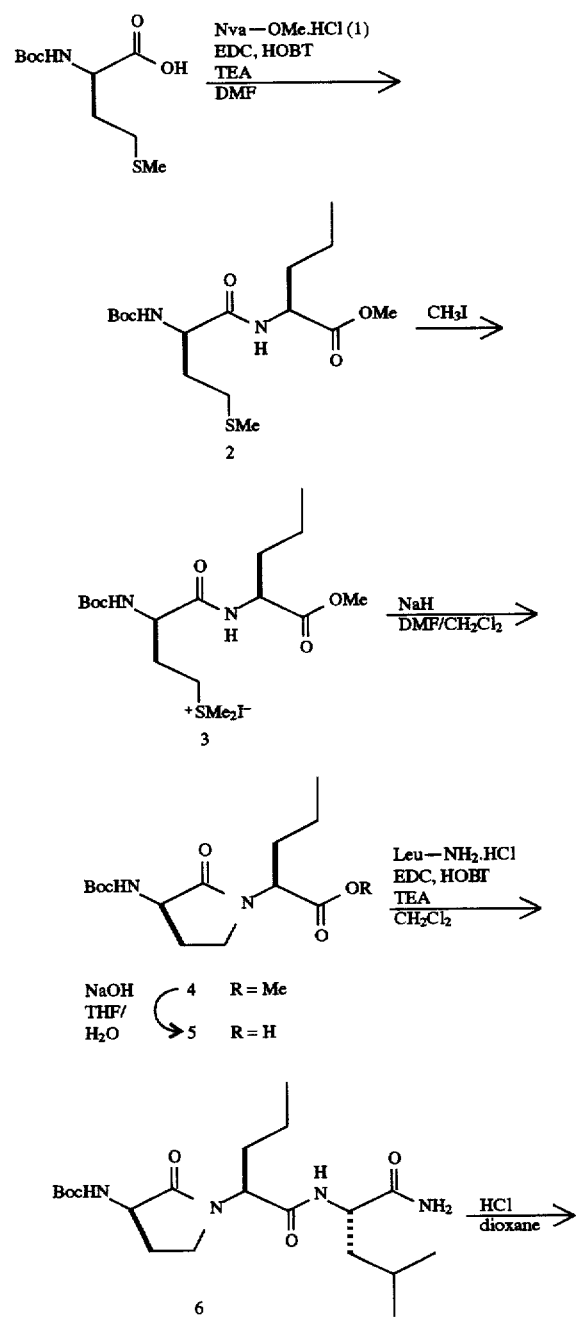

EXAMPLE 1

EtOCO-Phe-(R)-γ-Lactam-Nva-Leu-NH₂

Step 1

Preparation of L-Norvaline Methyl Ester (1)

To 20 mL of methanol was slowly added 2.6 mL acetyl chloride. Then 2.0 g (17.1 mmole) of L-norvaline was added. The solution was heated to reflux and monitored by thin-layer chromatography (TLC) until complete. The methanol was stripped off by rotary evaporation and the resulting oil was pumped under high vacuum overnight to give the title compound. NMR(300 MHZ, CD₃OD): δ 4.03 (t, Nva-α, 1H), 3.81 (s, COOCH₃, 3H), 1.87 (m, CH₂CH₂CH₃, 2H), 1.44 (m, CH₂CH₂CH₃, 2H), 0.98 (t, CH₂CH₂CH₃, 3H).

Step 2

Preparation of Boc-D-Met-Nva-methyl ester (2)

838 mg of L-Nva methyl ester (1; 5.0 mmole) and 1.25 g of Boc-D-methionine (5.0 mmole) were added to 13 mL of dry DMF. Then added 700 μEt₃N (5.0 mmole), followed by 675 mg HOBT and 960 mg EDC (5.0 mmole each) and allowed the reaction to stir overnight. TLC at 16 h showed that the starting materials had disappeared. The reaction mixture was diluted with dichloromethane and washed 3× with 30 mL of 5% citric acid and 2× with 5% NaHCO₃. The separated organic layer was dried over Na₂SO₄ and filtered. The filtrate was evaporated by rotary evaporation and the remaining residue was pumped on high vacuum to give the title compound. NMR (400 MHZ, CD₃OD): δ 4.38 (dd, Nva-α, 1H), 4.18 (dd, Met-α, 1H), 3.70 (s, COOCH₃, 3H), 2.08 (s, CH₂CH₂SCH₃, 3H), 1.43 (s, (CH₃13COCOMet, 9H), 0.93 (t, Nva-CH₃, 3H).

Step 3
Preparation of Boc-D-Met Methylsulfonium Iodide Nva-Methyl Ester (3)

1.60 g (4.4 mmole) of Boc-D-Met-Nva-methyl ester (2) was dissolved in 9 mL of iodomethane and allowed to stir overnight. TLC at 18 h indicated that all starting material had been consumed. The iodomethane was stripped by rotary evaporation on a rotary evaporator that was located in a fume hood. The residue was pumped on high vacuum to give the title compound as a white foam. NMR (300 MHZ, $CD_3OD$): δ 4.38 (dd, Nva-α, 1H), 4.25 (dd, Met-α, 1H), 3.73 (s, $COOCH_3$, 3H), 2.96 (s, $CH_2CH_2S(CH_3)_2I$, 6H), 1.45 (s, $(CH_3)_3COCOMet$, 9H), 0.93 (t, Nva-$CH_3$, 3H).

Step 4
Preparation of Boc-(R)-γ-Lactam-Nva-Methyl Ester (4)

2.16 g (4.3 mmole) of (3) was dissolved in 86 mL of a 1:1 mixture of $DMF/CH_2Cl_2$ (dry). The solution was cooled to 0° C., then 336 mg of 61% sodium hydride dispersion in mineral oil was added (8.6 mmole, 2.0 eq). The reaction was monitored by TLC, which indicated that a minor amount of the polar lactam acid (5) was also present. At 200 min, it was quenched by dropwise addition of ca. 1 mL of glacial acetic acid followed by ca. 1 mL of water. The solution was then evaporated by high vacuum rotary evaporation. 20 mL of water and 50 mL of 5% citric acid was then added to the residue, which was then extracted 3× with 40 mL of $CH_2Cl_2$. The organic layer was washed 2× with 40 mL of 5% citric acid, dried over $Na_2SO_4$, filtered, and the filtrate evaporated by rotary evaporation. The residue was pumped on high vacuum overnight. Silica gel chromatography was used to purify the crude material (1/1 hexanes/ethyl acetate), giving the title compound. Further elution with 1% acetic acid in ethyl acetate resulted in the recovery of the lactam acid (5).

NMR (400 MHZ, $CD_3OD$): δ 4.69 (dd, Nva-α, 1H), 4.23 (br t, Lac-α, 1H), 3.70 (s, $COOCH_3$, 3H), 3.39 (dd, Lac-γ, 2H), 2.42 (m, Lac-β, 1H), 1.91 (m, Lac-β, 1H), 1.43 (s, $(CH_3)_3COCOLac$, 9H), 0.96 (t, Nva-$CH_3$, 3H).

Step 5
Preparation of Boc-(R)-γ-Lactam-Nva (5)

50 mg (160 μmole) of (4) was dissolved in 0.8 mL THF, 0.2 mL of 0.5N NaOH added and monitored by TLC. When hydrolysis was noted to be only ⅓ complete at 90 min, another 20 μL of 5N NaOH was added. TLC 1 h later showed hydrolysis was complete. The reaction mixture was diluted with 20 mL of $CH_2Cl_2$ and washed with 5% citric acid. The aqueous layer was extracted twice more with $CH_2Cl_2$, and the combined extracts were dried over $Na_2SO_4$, filtered, and the filtrates evaporated to give the title compound.

NMR (400 MHZ, $CD_3OD$): δ 4.65 (dd, Nva-α, 1H), 4.24 br t, Lac-α, 1H), 3.39 (m, Lac-γ, 2H), 2.42 (m, Lac-β, 1H), 1.92 (m, Lac-β & $CH_2CH_2CH_3$, 2H), 1.43 (s, $(CH_3)_3COCOLac$, 9H), 0.96 (t, Nva-$CH_3$, 3H).

Step 6
Preparation of Boc-(R)-γ-Lactam-Nva-Leu-$NH_2$ (6)

257 mg of (5) (0.85 mmole) was dissolved in 3.4 mL $CH_2Cl_2$, after which was added 115 mg HOBT and 163 mg EDC (0.85 mmole each). The activated ester complex was stirred for 20 min, after which 142 mg (0.85 mmole) of leucine carboxamide.HCl and 120 mL (0.85 mmole) $Et_3N$ was added. The reaction was monitored by TLC. After 4 h the reaction mixture was diluted with $CH_2Cl_2$ and washed twice each with 5% citric acid and 5% $NaHCO_3$. The organic layer was dried over $Na_2SO_4$, filtered, and the filtrate evaporated by rotary evaporation. The residue was pumped on high vacuum overnight to give the title compound. NMR (300 MHZ, $CD_3OD$): δ 4.57 (dd, Nva-α, 1H), 4.36 (dd, Leu-α, 1H), 4.21 (br t, Lac-α, 1H), 3.44 (m, Lac-γ, 2H), 2.40 (m, Lac-β, 1H), 1.45 (s, $(CH_3)_3COCOLac$, 9H), 0.96 (t, Nva-$CH_3$, 3H), 0.95 (d, Leu-$CH_3$, 3H), 0.89 (d, Leu-$CH_3$, 3H).

Step 7
Preparation of HCl.$H_2$N-(R)-γ-Lactam-Nva-Leu-$NH_2$ (7)

268 mg of (6) (0.65 mmole) was dissolved in 3 mL of 4N hydrogen chloride in dioxane and the mixture allowed to stir. After 2 h the dioxane was evaporated and the residue pumped on high vacuum to give the title compound. NMR (300 MHZ, $CD_3OD$): δ 4.63 (dd, Nva-α, 1H), 4.38 (dd, Leu-α, 1H), 4.08 (dd, Lac-α, 1H), 3.75–3.52 (m, Lac-γ, 2H), 2.58 (m, Lac-β, 1H), 0.96 (t, Nva-$CH_3$, 3H), 0.95 (d, Leu-$CH_3$, 3H), 0.89 (d, Leu-$CH_3$, 3H). Mass spectrum [FAB] 313.4 (M+1).

Step 8
Preparation of EtOCO-Phe (8)

To 4.96 g (30 mmole) phenylalanine was added 76 mL of 1:1 mixture of water and dioxane, followed by 4.15 g (30 mmole) of $K_2CO_3$. After 10 min 2.87 mL of ethyl chloroformate (30 mmole) in 10 mL of dioxane was added dropwise, and the reaction mixture was allowed to stir. The reaction was monitored by TLC, and once complete (ca. 2 hrs) the solvent was stripped by rotary evaporation. The residue was reconstituted in 50 mL of 1N NaOH, then extracted with ethyl acetate. The aqueous layer was then acidified with 2N HCl to pH 2 and extracted 3× with ethyl acetate, after which the extract was dried over $Na_2SO_4$, filtered and the filtrate evaporated. The residue was pumped on high vacuum, after which it was recrystallized from $Et_2O$/hexanes in two crops to give the title compound. NMR (300 MHZ, $CD_3OD$): δ 7.22 (m, Ph, 5H), 4.38 (dd, Phe-α, 1H), 4.00 (q, $CH_3CH_2OCOPhe$, 2H), 3.17 (dd, Phe-β, 1H), 2.90 (dd, Phe-α, 1H), 1.17 (t, $CH_3CH_2OCOPhe$, 3H).

Step 9
Preparation of EtOCO-Phe-(R)-γ-Lactam-Nva-Leu-$NH_2$ (9)

To 13.5 mg of EtOCO-L-Phe (57 μmole) in 250 μL dry $CH_2Cl_2$ was added 8.0 mg HOBT and 11.3 mg EDC (59 μmole each). After stirring for 20 min 20.0 mg of (7) and 8.0 mL $Et_3N$ (57 μmole each) were added, followed by another 250 μL of $CH_2Cl_2$. The reaction was monitored by TLC, and after 4 h was diluted to 30 mL with $CH_2Cl_2$, then washed 2× with 5% citric acid and 3× with 5% $Na_2CO_3$. The organic layer was dried over $Na_2SO_4$, filtered, and the filtrate evaporated. The crude was purified by flash silica gel chromatography to give the title compound at 80% purity by RP-HPLC. The title compound was purified by prep RP-HPLC and lyophilized to give 98% analytically pure title compound. Selected NMR data (500 MHz, $CD_3OD$): δ 7.24 (m, Ph, 5H), 4.55 (dd, Nva-α, 1H), 4.43 (t, Phe-α,1H), 4.37 (dd, Leu-α & Lac-α, 2H), 4.00 (q, $CH_3CH_2OCO$, 2H), 3.43 (m, Lac-γ, 2H), 3.12 (dd, Phe-β, 1H), 2.86 (dd, Phe-β, 1H), 2.34 (m, Lac-β, 2H), 1.18 (t, $CH_3CH_2OCO$, 3H), 0.97 (t, Nva-$CH_3$, 3H), 0.92 (dd, Leu-2$CH_3$, 6H). Mass spectrum [FAB]: 532.2 (M+1).

EXAMPLE 2

EtOCO-Cha-(R)-γ-Lactam-Nva-Leu-$NH_2$ (10)

Using the general acylation method directly above in example 1, (10) was made by acylating (7), prepared according to the procedures of Example 1, Step 7, with EtOCO-Cha. NMR (500 MHz, $CD_3OD$): δ 4.54 (dd, Nva-α, 1H), 4.43 (t, Leu-α, 1H), 4.36 (m, Lac-α), 4.16 (dd, Cha-α, 1H), 4.10 (m, $CH_3CH_2OCO$, 2H), 3.47 (m, Lac-γ, 2H), 2.42 (m, Lac-β, 1H), 1.93 (m, Lac-β, 1H), 1.24 (t, $CH_3CH_2OCO$, 3H), 0.97 (t, Nva-$CH_3$, 3H), 0.91 (dd, Leu-2$CH_3$, 6H). Mass spectrum [FAB]: 538.3 (M+1).

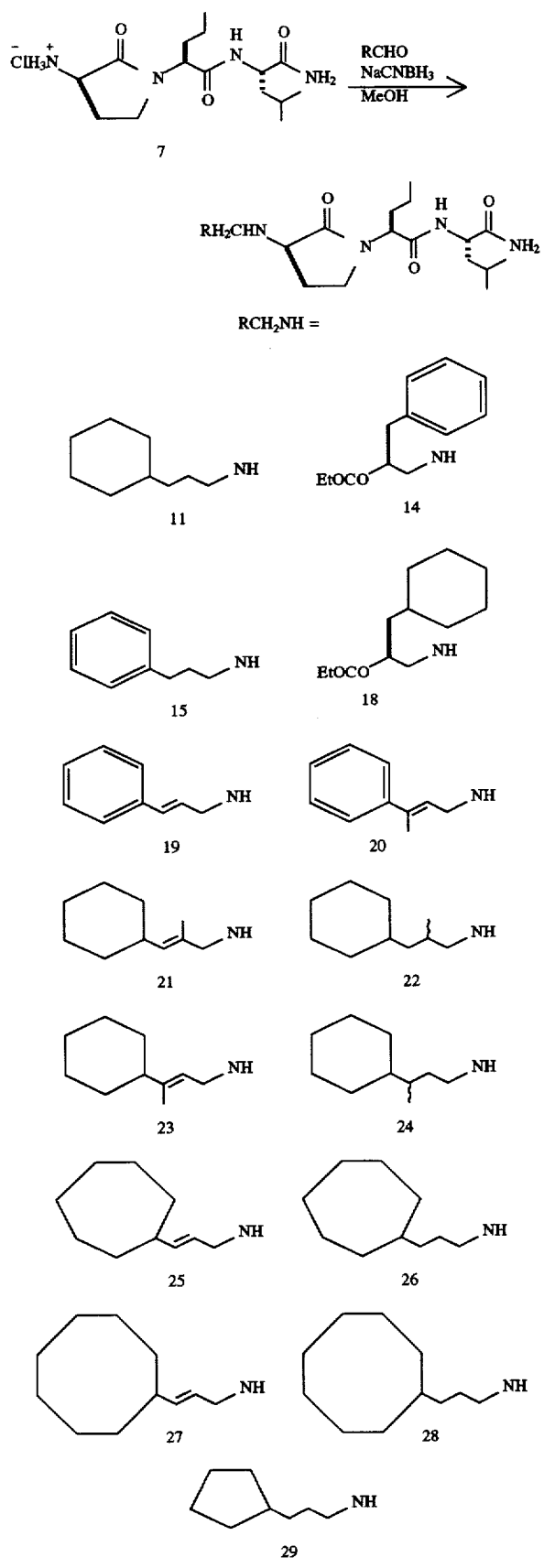

EXAMPLE 3 cHx(CH$_2$)$_3$-(R)-γ-Lactam-Nva-Leu-NH$_2$ (11)

40 mg (115 μmole) of (7), prepared according to the procedures of Example 1, Step 7, was dissolved in 2 mL of MeOH, after which 20 mL (115 μmole) of DIEA was added. After briefly stirring, 19 mL (115 μmole) of 3-cyclohexylpropionaldehyde and 10 mg (158 μmole, 1.4 eq.) sodium cyanoborohydride were added. Allowed the reaction to stir for 16 h, then diluted with 5% NaHCO$_3$ and extracted 3× with ethyl acetate. The organic layer was dried over Na$_2$SO$_4$, filtered, and the filtrate evaporated. The crude isolate was pumped on high vacuum, then purified by flash silica gel chromatography. The isolate was dissolved in CH$_2$Cl$_2$ and washed 2× with 0.25N HCl. The aqueous layer was basified with NaOH and extracted 2× with CH$_2$Cl$_2$ and 1× with ethyl acetate to give the title compound. NMR (500 MHz, CD$_3$OD): δ 4.60 (dd, Nva-α, 1H), 4.35 (dd, Leu-α, 1H), 3.63 (t, Lac-α, 1H), 3.47 (m, Lac-γ, 2H), 2.79 (m, CH$_2$CH$_2$CH$_2$cHx, 1H), 2.68 (m, CH$_2$CH$_2$CH$_2$cHx, 1H), 2.42 (m, Lac-β, 1H), 1.85 (m, Lac-β, 1H), 1.58 (m, CH$_2$CH$_2$CH$_2$cHx, 1H), 0.96 (t, Nva-CH$_3$, 3H). Mass spectrum [FAB]: 437.2 (M+1).

EXAMPLE 4

EtOCO-Pheψ(CH$_2$NH)-(R)-γ-Lactam-Nva-Leu-NH$_2$ (14)

Step 1
Preparation of EtOCO-Phe-N(OMe)Me (12):

To 400 μL CH$_2$Cl$_2$ was added 47.4 mg (200 μmole) of EtOCO-Phe, 34.8 mL (200 μmole) DIEA, and 88.4 mg (200 μmole) BOP. After 3 min, 19.4 mg (200 μmole) N,O-dimethyl-hydroxylamine.HCl and 34.8 mL (200 μmole) DIEA were added. The reaction was monitored by TLC, and after 45 min it was diluted with CH$_2$Cl$_2$, washed 2× with dilute HCl and 2× with saturated NaHCO$_3$. The organic layer was dried with Na$_2$SO$_4$, filtered, and the filtrate evaporated by rotary evaporation to give the title compound. NMR (300 MHz, CDCl$_3$): δ 7.20 (m, Ph, 5H), 4.82 (br m, Phe-α, 1H), 4.00 (q, CH$_3$CH$_2$OCO, 2H), 3.62 (s, N(CH$_3$)OCH$_3$, 3H), 3.11 (s, N(CH$_3$)OCH$_3$, 3H), 3.00 (dd, Phe-b, 1H), 2.85 (dd, Phe-b, 1H), 1.17 (t, CH$_3$CH$_2$OCO, 3H).

Step 2
Preparation of EtOCO-Phe-CHO (13):

To 56 mg (200 μmole) (12), prepared in Step 1, above, was added 2 mL of dry Et$_2$O, and the solution was cooled to 0° C. Lithium aluminum hydride (9.5 mg, 50 μmole, 1.25 eq. H$^-$) was added, and the reaction was monitored by TLC. After 2 h the reaction was quenched with ca. 4 mL ethyl acetate and the solution stirred for 40 min. The organic layer was washed 2× with dilute HCl, 2× with saturated NaHCO$_3$, and 1× with brine. The organic layer was dried with Na$_2$SO$_4$, filtered, and the filtrate evaporated. The residue was pumped on high vacuum overnight, then purified by flash silica gel chromatography to give the title compound. NMR (300 MHz, CDCl$_3$): δ 9.60 (s, CHO, 1H), 7.20 (m, Ph, 5H), 4.45 (br dd, Phe-α, 1H), 4.08 (q, CH$_3$CH$_2$OCO, 2H), 3.08 (d, Phe-β, 2H), 1.20 (t, CH$_3$CH$_2$OCO, 3H).

Step 3
Preparation of EtOCO-Pheψ(CH$_2$NH)-(R)-γ-Lactam-Nva-Leu-NH$_2$ (14):

Using a general reductive amination method, 12.7 mg (57 μmole) of aldehyde (13), 20 mg (57.4 μmole) of (7), 115 mL (115 μmole, 2.0 eq) of 1N sodium cyanoborohydride and 10 μL (57 μmole) of DIEA were combined in 0.5 mL methanol to give the title compound after NaHCO$_3$ workup and silica gel chromatography. NMR (500 MHz, CD₃OD): δ 7.22 (m, Ph, 5H), 4.59 (dd, Nva-α, 1H), 4.35 (dd, Leu-α, 1H), 4.00 (q, CH₃CH₂OCO, 2H), 3.90 (m, Lac-α, 1H), 3.42 (m, Phe-α & Lac-γ, 3H), 2.75 (m, EtOCOPheCH₂, 2H), 2.31 (m, Lac-α, 1H), 1.82 (m, Lac-β, 1H), 1.17 (t,CH₃CH₂OCO, 3H), 0.95 (t, Nva-CH₃, 3H), 0.94 (d, Leu-CH₃, 3H), 0.89 (d, Leu-CH₃, 3H). Mass spectrum [FAB]: 518.3 (M+1).

EXAMPLE 5

Ph(CH₂)₃-(R)-γ-Lactam-Nva-Leu-NH₂ (15)

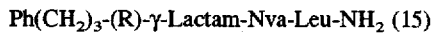

Using the general reductive amination method, 7.6 mL (57 mmole) of hydrocinnamaldehyde, 20 mg (57.4 μmole) of (7), 115 μL (115 μmole, 2.0 eq) of 1N sodium cyanoborohydride and 10 μL (57 μmole) of DIEA were combined in 0.5 mL methanol to give the title compound after acid-base workup and silica gel chromatography. NMR (500 MHz, CD₃OD): δ 7.20 (m, Ph, 5H), 4.60 (dd, Nva-α, 1H), 4.35 (dd, Leu-α, 1H), 3.42 (m, Lac-α & Lac-γ, 3H), 2.68 (m, PhCH₂CH₂CH₂, 4H), 2.34 (m, Lac-β, 1H), 0.96 (t, Nva-CH₃, 3H), 0.95 (d, Leu-CH₃, 3H), 0.89 (d, Leu-CH₃, 3H). Mass spectrum [FAB]: 431.2 (M+1).

EXAMPLE 6

[EtOCO-Chaψ(CH₂NH)-(R)-γ-Lactam-Nva-Leu-NH₂ (18)

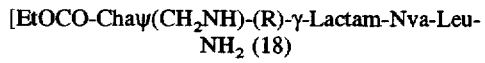

Step 1
Preparation of EtOCO-Cha-N(OMe)Me (16):

To 0.5 mL CH₂Cl₂ was added 48.6 mg (200 μmole) of EtOCO-Cha, 34.8 μL (200 μmole) DIEA, and 88.4 mg (200 μmole) BOP. After 3 min, 19.4 mg (200 μmole) N,O-dimethyl-hydroxylamine·HCl and 34.8 μL (200 μmole) DIEA were added. The reaction was monitored by TLC, and after 90 min it was diluted with CH₂Cl₂, washed 2× with dilute HCl and 2× with saturated NaHCO₃. The organic layer was dried with Na₂SO₄, filtered, and the filtrate evaporated by rotary evaporation to give the title compound. NMR (300 MHz, CDCl₃): a 4.72 (br m, Cha-α, 1H), 4.04 (q, CH₃CH₂OCO, 2H), 3.72 (s, N(CH₃)OCH₃, 3H), 3.13 (s, N(CH₃)OCH₃, 3H), 1.17 (t, CH₃CH₂OCO, 3H).

Step 2
Preparation of EtOCO-Cha-CHO (17):

To 57 mg (200 μmole) (16) was added 1.8 mL of dry THF, and the solution was cooled to 0° C. Then 9.5 mg of lithium aluminum hydride (250 μmole, 1.25 eq H⁻) was added, and the reaction was monitored by TLC. After 45 min the reaction was quenched with ca. 20 mL ethyl acetate and the solution stirred for 40 min. The organic layer was washed 1× with 5% citric acid and 1× with 5% NaHCO₃. The organic layer was dried with Na₂SO₄, filtered, and the filtrate evaporated. The residue was pumped on high vacuum overnight to give the title compound. NMR (300 MHz, CDCl₃): δ 9.52 (s, CHO, 1H), 4.27 (br m, Cha-α, 1H), 4.04 (q, CH₃CH₂OCO, 2H), 1.80–0.80 (m, cHxCH₂, 13H), 1.17 (t, CH₃CH₂OCO, 3H).

Step 3
Preparation of EtOCO-Chaψ(CH₂NH)-(R)-γ-Lactam-Nva-Leu -NH₂ (18):

Using the general reductive amination method, 12.5 mg (55 μmole) of aldehyde (17), from Step 2, above, 20 mg (57.4 μmole) of (7), prepared according to Example 1, Step 7, 115 μL (115 μmole, 2.0 eq) of 1N sodium cyanoborohydride and 10 μL (57 μmole) of DIEA were combined in 0.5 mL methanol to give the title compound after NaHCO₃ workup and silica gel chromatography. NMR (500 MHz, CD₃OD): α 4.59 (dd, Nva-α, 1H), 4.35 (dd, Leu-α, 1H), 4.06 (q, CH₃CH₂OCO, 2H), 3.80 (m, Lac-α, 1H), 3.44 (m, Cha-α & Lac-γ, 3H), 2.72 (dd, EtOCOChaCH₂, 1H), 2.56 (dd, EtOCOChaCH₂, 1H), 2.34 (m, Lac-β, 1H), 1.83 (m, Lac-β, 1H), 1.25 (t, CH₃CH₂OCO, 3H), 0.96 (t, Nva-CH₃, 3H), 0.95 (d, Leu-CH₃, 3H), 0.89 (d, Leu-CH₃, 3H). Mass spectrum [FAB]: 524.5 (M+1).

EXAMPLE 7

Ph(CH=CHCH₂)-(R)-γ-Lactam-Nva-Leu-NH₂ (19)

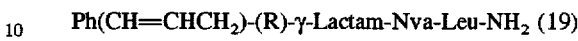

Using the general reductive amination method, 7.3 μL (57 μmole) of trans-cinnamaldehyde, 20 mg (57.4 μmole) of (7), prepared according to Example 1, Step 7, 58 μL (58 μmole) of 1N sodium cyanoborohydride and 10 μL (57 μmole) of DIEA were combined in 0.5 mL methanol to give the title compound after NaHCO₃ workup and silica gel chromatography. NMR (500 MHz, CD₃OD): δ 7.40–7.19 (d,t,dt, Ph, 5H), 6.59 (d, PhCH=CHCH₂, 1H), 6.30 (m, PhCH=CHCH₂, 1H), 4.61 (dd, Nva-α, 1H), 4.35 (dd, Leu-α, 1H), 3.54 (dr, Lac-α, 1H), 3.48 (d, PhCH=CHCH₂, 2H), 3.41 (m, Lac-γ, 2H), 2.38 (m, Lac-β, 1H), 1.84 (m, Lac-β, 1H), 0.96 (t, Nva-CH₃, 3H), 0.91 (d, Leu-CH₃, 3H), 0.87 (d, Leu-CH₃, 3H). Mass spectrum [FAB]: 429.2 (M+1).

EXAMPLE 8

Ph(C(CH₃)=CHCH₂NH)-(R)-γ-Lactam-Nva-Leu-NH₂ (20)

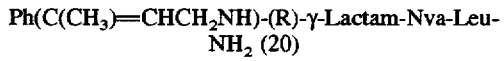

Using the general reductive amination method, 8.0 μL (57 μmole) of α-methyl trans-cinnamaldehyde, 20 mg (57.4 μmole) of (7), prepared according to the procedures of Example 1, Step 7, 58 μL (58 μmole) of 1N sodium cyanoborohydride and 10 μL (57 μmole) of DIEA were combined in 0.5 mL methanol to give the title compound after NaHCO₃ workup and silica gel chromatography. NMR (500 MHz, CD₃OD): δ 7.32–7.17 (t,d,dt, Ph, 5H), 6.50 (m, Ph(CH₃)C=CHCH₂, 1H), 4.62 (dd, Nva-α, 1H), 4.36 (dd, Leu-α, 1H), 3.50 (t, Lac-α, 1H), 3.47 (m, Lac-γ, 2H), 3.40 (d, Ph(CH₃)C=CHCH₂, 2H), 2.40 (m, Lac-β, 1H), 1.90 (s, Ph(CH₃)C=CHCH₂, 3H), 1.86 (m, Lac-β, 1H), 0.96 (t, Nva-CH₃, 3H), 0.91 (d, Leu-CH₃, 3H), 0.87 (d, Leu-CH₃, 3H). Mass spectrum [FAB]: 443.2 (M+1).

EXAMPLE 9 cHx(CH=C(CH₃)CH₂-(R)-γ-Lactam-Nva-Leu-NH₂, (21)

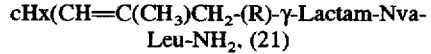

Using the general reductive amination, 15.7 mg (103 μmole, 1.2 eq) of β-methyl trans-hexahydrocinnamaldehyde, 30 mg (86 μmole) of (7), prepared according to Step 7 of Example 1, 172 μL (172 μmole) of 1N sodium cyanoborohydride and 15 μL (86 μmole) of DIEA were combined in 0.5 mL methanol to give the title compound after NaHCO₃ workup and silica gel chromatography. NMR (500 MHz, CD₃OD): δ 5.21 (d, cHxCH=(CH₃)CCH₂, 1H), 4.61 (dd, Nva-α, 1H), 4.35 (dd, Leu-α, 1H), 3.45 (m, Lac-α & Lac-γ, 3H), 2.36 (m, Lac-β, 2H), 0.96 (t, Nva-CH₃, 3H). Mass spectrum [FAB]: 449.3 (M+1), 451.3 (M+3).

EXAMPLE 10 cHx(CHP₂C(CH₃)CH₂)-(R)-γ-Lactam-Nva-Leu-NH₂ (22)

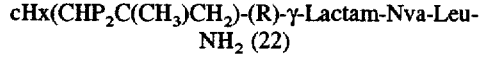

5.8 mg (15 μmole) of (21), prepared according to the procedures of Example 9, was dissolved in 1 mL of methanol and 4.6 mg of 10% palladium on carbon was added. The reaction vessel was evacuated and charged with $H_2$. After 4 h the reaction mixture was filtered over Celite™ diatomaceous earth and the filtrate evaporated. The crude was purified over silica gel twice (95/5 $CH_2Cl_2$/methanol, then 95/5/1 $CH_2Cl_2$/methanol/ammonium hydroxide) to give the title compound. NMR (500 MHz, $CD_3OD$): δ 4.61 (dd, Nva-α, 1H), 4.36 (dd, Leu-α, 1H), 3.45 (m, Lac-α& Lac-γ, 3H), 2.81–2.40 (m, cHxCH$_2$(CH$_3$)CCH$_2$, 2H), 2.36 (m, Lac-β, 2H), 0.96 (t, Nva-CH$_3$, 3H). Mass spectrum [FAB]: 451.4 (M+1).

EXAMPLE 11 cHx((CH$_3$)C═CHCH$_2$)-(R)-γ-Lactam-Nva-Leu-NH$_2$ (23)

Using the general reductive amination, 8.8 mg (57 μmole) of 3-methyl trans-hexahydrocinnamaldehyde, 20 mg (57.4 μmole) of (7), prepared according to procedures of Example 1, Step 7, 60 μL (60 μmole) of 1N sodium cyanoborohydride and 10 μL (57 μmole) of DIEA were combined in 0.5 mL methanol to give 8.0 mg (31% yield) of the title compound combined with 10% of saturated compound (24) after NaHCO$_3$ workup and silica gel chromatography. NMR (500 MHz, CD$_3$OD): δ 5.26 (t, CH$_2$CH═C(CH$_3$), 1H), 4.60 (dd, Nva-α, 1H), 4.36 (dd, Leu-α, 1H), 3.47 (dt, Lac-α, 1H), 3.42 (m, Lac-γ, 1H), 3.31 (m, Lac-γ, 1H), 2.42 (m, Lac-β, 2H), 1.65 (s, CH$_2$CH═C(CH$_3$), 3H), 0.96 (t, Nva-CH$_3$, 3H), 0.94 (d, Leu-CH$_3$, 3H), 0.89 (d, Leu-CH$_3$, 3H). Mass spectrum [FAB]: 449.2 (M+1).

EXAMPLE 12 cHx((CH$_3$)CHCH$_2$CH$_2$NH)-(R)-γ-Lactam-Nva-Leu-NH$_2$ (24)

5.3 mg (12 μmole) of (23), prepared according to procedures of Example 11, was dissolved in 1 mL of methanol and 2.3 mg of 10% palladium on carbon was added. The reaction vessel was evacuated and charged with hydrogen. After 1 hr the reaction mixture was filtered over Celite™ diatomaceous earth and the filtrate evaporated to give the diastereomeric title compound. NMR (500 MHz, CD$_3$OD): δ 4.61 (dd, Nva-α, 1H), 4.36 (dd, Leu-α, 1H), 3.44 (m, Lac-α & Lac-γ, 3H), 2.66 (m, CH$_2$CH$_2$CH(CH$_3$), 2H), 2.37 (m, Lac-β, 2H), 0.96 (t, Nva-CH$_3$, 3H), 0.95 (d, Leu-CH$_3$, 3H), 0.89 (d, Leu-CH$_3$, 3H), 0.86 (d, CH$_2$CH$_2$CH(CH$_3$), 3H). Mass spectrum [FAB]: 451.2 (M+1).

EXAMPLE 13 cHp(CH═CHCH$_2$)-(R)-γ-Lactam-Nva-Leu-NH$_2$ (25)

Using the general reductive amination method, 10.1 mg (66 μmole, 1.16 eq) of 3-cycloheptyl-1-propenal, 3.3 μL (57 μmole) of acetic acid, 20 mg (57.4 μmole) of (7), prepared according to the procedures of Example 1, Step 7, 115 μL (115 μmole) of 1N sodium cyanoborohydride and 10 μL (57 μmole) of DIEA were combined in 0.25 mL methanol to give the title compound combined with 33% of saturated compound (26) after NaHCO$_3$ workup and silica gel chromatography. NMR (500 MHz, CD$_3$OD): δ 5.67 (dd, CH$_2$CH═CHcHp, 1H), 5.44 (m, cHpCH═CHCH$_2$, 1H), 4.60 (dd, Nva-α, 1H), 4.36 (dd, Leu-α, 1H), 3.44 (m, Lac-α& Lac-γ, 3H), 3.24 (t, cHpCH═CHCH$_2$, 2H), 2.35 (m, Lac-α, 2H), 0.96 (t, Nva-CH$_3$, 3H), 0.94 (dd, Leu-CH$_3$, 3H), 0.89 (dd, Leu-CH$_3$, 3H). Mass spectrum [FAB]: 49.4 (M+1), 451.4 (M+3).

EXAMPLE 14 cHp(CH$_2$)$_3$-(R)-γ-Lactam-Nva-Leu-NH$_2$ (26)

3.5 mg (8 μmole) of (25), prepared according to Example 13, was dissolved in 1 mL of methanol and 1 mg of 10% palladium on carbon was added. The reaction vessel was evacuated and charged with $H_2$. After 3 h the reaction mixture was filtered over Celite™ diatomaceous earth and the filtrate evaporated to give the title compound. NMR (500 MHZ, CD$_3$OD): δ 4.60 (dd, Nva-α, 1H), 4.36 (dd, Leu-α, 1H), 3.45 (m, Lac-α & Lac-γ, 3H), 2.65 (m, CH$_2$CH$_2$CH$_2$cHp, 1H), 2.57 (m, CH$_2$CH$_2$CH$_2$cHp, 1H), 2.36 (m, Lac-β, 1H), 0.96 (t, Nva-CH$_3$, 3H), 0.95 (d, Leu-CH$_3$, 3H), 0.89 (d, Leu-CH$_3$, 3H). Mass spectrum [FAB]: 451.2 (M+1).

EXAMPLE 15 cOct(CH═CHCH$_2$)-(R)-γ-Lactam-Nva-Leu-NH$_2$ (27)

Using the general reductive amination method, 18.9 mg (114 μmole, 1.14 eq) of 3-cyclooctyl-1-propenal, 34.9 mg (100 μmole) of (7), prepared in Example 1, Step 7, 9.5 mg (150 μmole, 1.5 eq) of sodium cyanoborohydride and 18 μL (100 μmole) of DIEA were combined in 0.5 mL methanol to give the title compound combined with the saturated compound (28) after NaHCO$_3$ workup and silica gel chromatography. NMR (500 MHz, CD$_3$OD): δ 5.66 (dd, CH$_2$CH═CHcOct, 1H), 5.45 (m, CH$_2$CH═CHcOct, 1H), 4.60 (m, Nva-α, 1H), 4.36 (dd, Leu-α, 1H), 3.43 (m, Lac-α& Lac-γ, 3H), 3.24 (t, CH$_2$CH═CHcOct, 2H), 2.36 (m, Lac-β, 1H), 0.96 (t, Nva-CH$_3$, 3H), 0.95 (dd, Leu-CH$_3$, 3H), 0.89 (dd, Leu-CH$_3$, 3H). Mass spectrum [FAB]: 463.5 (M+1), 465.4 (M+3).

EXAMPLE 16 cOct(CH$_2$)$_3$-(R)-γ-Lactam-Nva-Leu-NH$_2$ (28)

4 mg (9 μmole) of (27), prepared as in Example 15, was dissolved in 1 mL of methanol and 2.5 mg of 10% palladium on carbon was added. The reaction vessel was evacuated and charged with $H_2$. After 2.5 h the reaction mixture was filtered over Celite™ diatomaceous earth and the filtrate evaporated to give the title compound. NMR (500 MHz, CD$_3$OD): δ 4.60 (dd, Nva-α, 1H), 4.36 (dd, Leu-α, 1H), 3.45 (m, Lac-α& Lac-γ, 3H), 2.65 (m, CH$_2$CH$_2$CH$_2$cOct, 1H), 2.57 (m, CH$_2$CH$_2$CH$_2$cOct, 1H), 2.36 (m, Lac-β, 1H), 0.96 (t, Nva-CH$_3$, 3H), 0.95 (d, Leu-CH$_3$, 3H), 0.89 (d, Leu-CH$_3$, 3H). Mass spectrum [FAB]: 465.4 (M+1).

EXAMPLE 17 cPn(CH$_2$)$_3$-(R)-γ-Lactam-Nva-Leu-NH$_2$ (29)

Using the general reductive amination method, 25.2 mg (200 μmole, 2.0 eq) of 3-cyclopentyl-1-propanal, 34.9 mg (100 μmole) of (7), prepared as in Example 1, Step 7, 10 mg (159 μmole, 1.59 eq) of sodium cyanoborohydride and 18 μL (100 μmole) of DIEA were combined in 0.5 mL methanol to give the title compound after NaHCO$_3$ workup and silica gel chromatography. NMR (500 MHz, CD$_3$OD): δ 4.60 (dd, Nva-α, 1H), 4.36 (dd, Leu-α, 1H), 3.44 (m, Lac-α & Lac-γ, 3H), 2.66 (m, CH$_2$CH$_2$CH$_2$cPn, 1H), 2.58 (m, CH$_2$CH$_2$CH$_2$cPn, 1H), 2.36 (m, Lac-β, 1H), 0.96 (t, Nva-CH$_3$, 3H), 0.95 (d, Leu-CH$_3$, 3H), 0.89 (d, Leu-CH$_3$, 3H). Mass spectrum [FAB]: 423.2 (M+1).

EXAMPLE 18 cHx(CH$_2$)$_3$-(R)-γ-Lactam-Nva-α-aza-Leu-NH$_2$ (32)

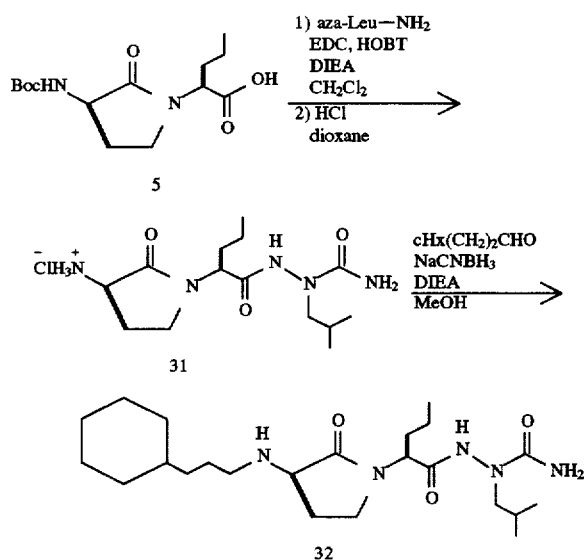

Step 1
Preparation of Boc-(R)-γ-Lactam-Nva-α-aza-Leu-NH$_2$ (30)

Step 2
Preparation of HCl.H$_2$N-(R)-γ-Lactam-Nva-α-aza-Leu-NH$_2$ (31)

10 mg (23.4 μmole) of (30), the product of Step 1, was dissolved in 1 mL of 4N hydrogen chloride. After 45 min the dioxane was evaporated and pumped on high vacuum to give the title compound. NMR (300 MHz, CD$_3$OD): δ 4.53 (br t, Nva-α, 1H), 4.10 (t, Lac-α, 1H), 3.61 (m, Lac-β, 2H), 3.40 & 3.12 (2 br m, aza-Leu-CH$_2$CH(CH$_3$)$_2$, 2H), 2.60 (m, Lac-β, 1H), 2.00 (m, Lac-β, 1H), 1.00 (t, Nva-CH$_3$, 3H), 0.93 (d, aza-Leu-CH$_3$, 3H), 0.91 (d, aza-Leu-CH$_3$, 3H).

Step 3
Preparation of cHx(CH$_2$)$_3$-(R)-γ-Lactam-Nva-α-aza-Leu-NH$_2$ (32)

5 μL (32.6 μmole, 1.4 eq.) of 3-cyclohexyl-1-propanal, 8.5 mg (23.4 μmole) of (31), the product of Step 2, 2 mg (31.7 μmole, 1.4 eq) of 1N sodium cyanoborohydride and 5 μL (28 μmole) of DIEA were combined in 0.5 mL methanol to give the title compound after NaHCO$_3$ workup and silica gel chromatography. NMR (500 MHz, CD$_3$OD): δ 4.45 (br t, Nva-α, 1H), 3.51 (m, Lac-γ, 2H), 3.38 (br m, aza-Leu-CH$_2$CH(CH$_3$)$_2$, 1H), 3.12 (br m, aza-Leu-CH$_2$CH(CH$_3$)$_2$, 1H), 2.68 (m, CH$_2$CH$_2$CH$_2$cHx, 1H), 2.58 (m, CH$_2$CH$_2$CH$_2$cHx, 1H), 2.39 (m, Lac-β, 1H), 1.83 (m, Lac-β & Nva-β, 3H), 0.98 (t, Nva-CH$_3$, 3H), 0.91 (d, aza-Leu-CH$_3$, 3H), 0.90 (d, aza-Leu-CH$_3$, 3H). Mass spectrum FAB]: 438.1 (M+1).

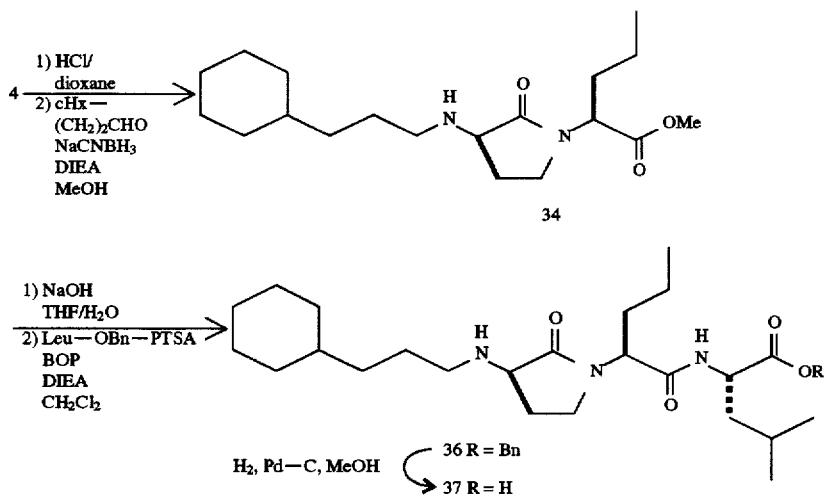

46.1 mg of (5), prepared according to the procedure of Example 1, Step 5, (0.15 mmole) was dissolved in 2 mL CH$_2$Cl$_2$, after which was added 24.3 mg HOBT and 34.6 mg EDC (0.18 mmole, 1.2 eq. each). The activated ester complex was stirred for 20 min, after which 22 mg (0.17 mmole) of (α-aza)-leucine carboxamide in 1 mL CH$_2$Cl$_2$ was added. The reaction was stirred overnight. The reaction mixture was diluted with CH$_2$Cl$_2$ and washed twice each with 5% citric acid and 5% NaHCO$_3$. The organic layer was dried over Na$_2$SO$_4$, filtered, and the filtrate was evaporated by rotary evaporation. The residue was pumped on high vacuum overnight to give the title compound. NMR (300MHz, CD$_3$OD): δ 4.32 (br t, Nva-α, 1H), 4.11 (t, Lac-α, 1H), 3.51 (m, Lac-γ, 2H), 3.08 (br m, aza-Leu-CH$_2$CH(CH$_3$)$_2$, 1H), 2.41 (m, Lac-β, 1H), 2.00 (m, Lac-β, 1H), 0.99 (t, Nva-CH$_3$, 3H), 0.93 (d, aza-Leu-CH$_3$, 3H), 0.91 (d, aza-Leu-CH$_3$, 3H).

EXAMPLE 19 cHx(CH$_2$)$_3$HN-(R)-γ-Lactam-Nva-Leu-OBn (36)

Step 1
Preparation of HCl.H$_2$N-(R)-γ-Lactam-Nva-OMe (33)

150 mg (478 μmole) of (4), prepared according to Example 1, Step 4, was dissolved in 2 mL of 4N hydrogen chloride in dioxane. After 90 min the dioxane was evaporated and pumped on high vacuum to give the title compound. NMR (300 MHz, CD$_3$OD): δ 4.69 (dd, Nva-α, 1H), 4.09 (dd, Lac-α, 1H), 3.73 (s, COOCH$_3$, 3H), 3.49 (m, Lac-γ, 2H), 2.60 (m, Lac-β, 1H), 1.94 (m, Lac-β, 1H), 0.97 (t, Nva-CH$_3$, 3H).

Step 2
Preparation of cHx(CH$_2$)$_3$-(R)-γ-Lactam-Nva-OMe (34)

All of (33), the product of Step 1, was dissolved in 2 mL methanol, after which 83 μL (478 μmole) DIEA, 73 μL (478

μmole) 3-cyclohexyl-1-propanal and 480 μL of 1N sodium cyanoborohydride in THF were all added. Stirred overnight, then gave a NaHCO₃ workup and purified by silica gel chromatography to give the title compound. NMR (300 MHz, CD₃OD): δ 4.68 (dd, Nva-α, 1H), 3.70 (s, COOCH₃, 3H), 3.48 (dd, Lac-α, 1H), 3.37 (m, Lac-γ, 2H), 2.63 (m, CH₂CH₂CH₂cHx, 2H), 2.38 (m, Lac-β, 1H), 1.89 (m, Lac-β, 1H), 0.94 (t, Nva-CH₃, 3H).

Step 3
Preparation of cHx(CH₂)₃-(R)-γ-Lactam-Nva (35)

59 mg (175 μmole) of (34), the product Step 2, was dissolved in a mixture of 1.6 mL of THF and 0.4 mL of 1N NaOH. Stirred for 90 min, then acidified with HCl and extracted with ethyl acetate to isolate the title compound. NMR (400 MHz, CD₃OD): δ 4.47 (dd, Nva-α, 1H), 4.05 (dd, Lac-α, 1H), 3.58 (m, Lac-γ, 1H), 3.42 (t, Lac-γ, 1H), 3.11 (m, CH₂CH₃CH₃cHx, 1H), 2.95 (m, CH₂CH₃CH₃cHx, 1H), 2.52 (m, Lac-β, 1H), 1.97 (m, Lac-γ, 1H), 0.96 (t, Nva-CH₃, 3H).

Step 4
Preparation of cHx(CH₂)₃-(R)-γ-Lactam-Nva-Leu-OBn (36)

29.2 mg (90 μmole) of (35), the product of Step 3, was dissolved in 1.3 mL CH₂Cl₂. Then added 35.5 mg (90 μmole) leucine benzyl ester PTSA salt and 16 μL (90 μmole) DIEA. The solution was briefly stirred, then 40 mg (90 μmole) BOP and 16 μL DIEA were added and the reaction was stirred for 90 min. The reaction was diluted with CH₂Cl₂, then washed 2× each with 5% citric acid and 5% NaHCO₃. The organic layer was dried over Na₂SO₄, filtered, and the filtrate was evaporated. Isolated the title compound after flash silica gel chromatography. NMR (500 MHz, CD₃OD): δ 7.34 (m, Ph, 5H), 5.13 (dd, OCH₂Ph, 2H), 4.58 (dd, Nva-α, 1H), 4.42 (dd, Leu-α, 1H), 3.43 (m, Lac-α & Lac-γ, 3H), 2.64 (m, CH₂CH₂CH₂cHx, 1H), 2.56 (m, CH₂CH₂CH₂cHx, 1H), 2.34 (m, Lac-β, 1H), 0.92 (d, Leu-CH₃, 3H), 0.91 (t, Nva-CH₃, 3H), 0.87 (d, Leu-CH₃, 3H). Mass spectrum [FAB]: 528.4 (M+1).

EXAMPLE 20 cHx(CH₂)₃-(R)-γ-Lactam-Nva-Leu-OH (37)

33 mg (63 μmole) of (36), the product of Example 19, was dissolved in 1.5 mL of methanol. 15 mg of 10% palladium on carbon was then added and the reaction vessel was evacuated and charged with H₂. The reaction was allowed to stir overnight. The catalyst was filtered off over Celite™ diatomaceous earth, and the filtrate was evaporated. NMR of the crude material shows some epimerization at the leucine-α proton. Silica gel chromatography was not helpful in purifying away the other isomer, so the title compound was isolated as a mixture of the two Leu configurations of the pseudo-tetrapeptide. NMR (400 MHz, CD₃OD): δ 4.62 (dd, Nva-α, 1H), 4.29 (dd, Leu-α, 1H), 3.95 (dd, Lac-α, 1H), 3.53 (m, Lac-γ, 2H), 3.06 (m, CH₂CH₂CH₂cHx, 1H), 2.89 (m, CH₂CH₂CH₂cHx, 1H), 2.52 (m, Lac-β, 1H), 0.98 (t, Nva-CH₃, 3H), 0.92 (d, Leu-CH₃, 3H), 0.88 (d, Leu-CH₃, 3H). Mass spectrum [FAB]: 438.3 (M+1).

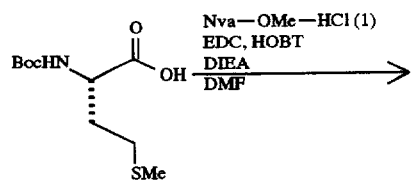

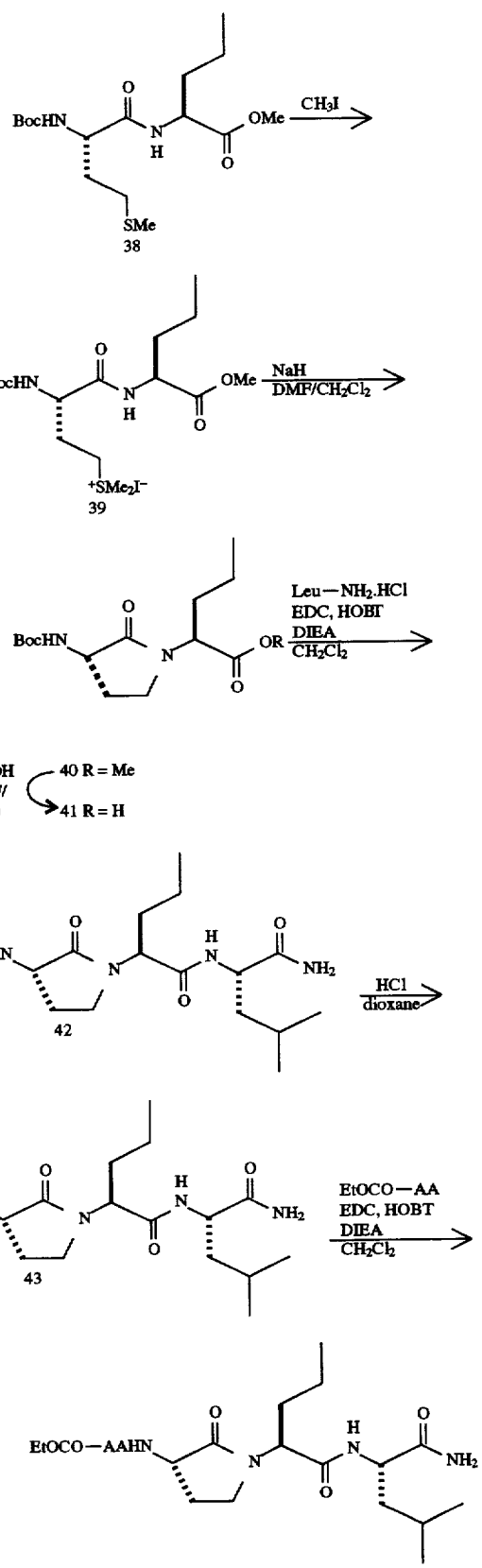

EtOCO—AANH =

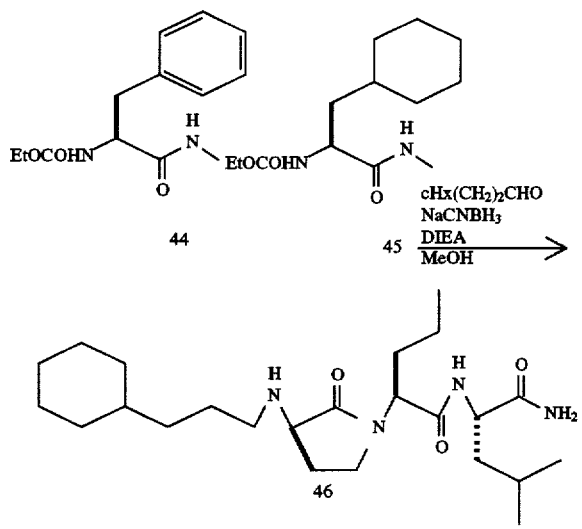

EXAMPLE 21

EtOCO-Phe-(S)-γ-Lactam-Nva-Leu-NH₂ (44)

Step 1
Preparation of Boc-L-Met-Nva-OMe (38)

434 mg of L-Nva methyl ester (1; 2.5 mmole, Example 1, Step 1) methionine (2.5 mmole), Example 1, Step 1, were added to 7.5 mL of dry DMF. Then added 450 μL DIEA (2.5 mmole), followed by 340 mg HOBT and 480 mg EDC (2.5 mmole each) and allowed the reaction to stir overnight. The DMF was stripped by high vacuum rotary evaporation and the residue was diluted with CH₂Cl₂ and washed 2× with 30 mL of 5% citric acid, 2× with 5% NaHCO₃ and 1× with brine. The separated organic layer was dried over Na₂SO₄ and filtered. The filtrate was evaporated by rotary evaporation and the remaining residue was pumped on high vacuum to give the title compound. NMR (300 MHz, CDCl₃): δ 4.56 (ddd, Nva-α, 1H), 4.27 (m, Met-α, 1H), 3.72 (s, COOCH₃, 3H), 2.57 (t, CH₂CH₂SCH₃, 2H), 2.10 (s, CH₂CH₂SCH₃, 3H), 1.43 (s, (CH₃)3COCOMet, 9H), 0.91 (t, Nva-CH₃, 3H).

Step 2
Preparation of Boc-L-Met methylsulfonium iodide-Nva-OMe (39)

732 mg (2.0 mmole) of Boc-L-Met-Nva methyl ester (38), product of Step 1, was dissolved in 4.5 mL of iodomethane and allowed to stir 90 h. The iodomethane was stripped by rotary evaporation on a rotary evaporator that was located in a fume hood. The residue was pumped on high vacuum to give the title compound as a white foam. NMR (300 MHz, CD₃OD): δ 4.41 (dd, Nva-α, 1H), 4.28 (t, Met-α, 1H), 3.73 (s, COOCH₃, 3H), 2.94 (s, CH₂CH₂S(CH₃)₂I, 6H), 1.44 (s, (CH₃)₃COCOMet, 9H), 0.94 (t, Nva-CH₃, 3H).

Step 3
preparation of Boc-(S)-γ-Lactam-Nva-OMe (40) and Boc-(S)-γ-Lactam-Nva-OH (41)

1.01 g (2.0 mmole) of (39), product of Step 2, was dissolved in 40 mL of a 1:1 mixture of DMF:CH₂Cl₂ (dry). The solution was cooled to 0° C., then 165 mg of 61% sodium hydride dispersion in mineral oil was added (4.0 mmole, 2.0 eq). The reaction was monitored by TLC, which indicated that a minor amount of the polar lactam acid (41) was also present. At 3 h it was quenched by dropwise addition of ca. 1 mL of glacial acetic acid followed by ca. 1 mL of water. The solution was then evaporated by high vacuum rotary evaporation. The residue was reconstituted with 40 mL CH₂Cl₂ and washed 3× with 5% citric acid. The organic layer was then washed 4× with 20 mL of 2N NaOH. The organic layer was then dried over Na₂SO₄, filtered, and the filtrate was evaporated by rotary evaporation to give crude ester (40), which appears to contain two isomers. The basic aqueous layer was acidified with 2N HCl, then extracted 4× with ethyl acetate. The ethyl acetate was dried over Na₂SO₄, filtered, and the filtrate evaporated to give the acid (41). NMR (40) (300 MHz, CD₃OD): δ 4.67 (dd, Nva-α, 1H), 4.23 (br m, Lac-α, 1H), 3.71 (s, COOCH₃, 3H), 3.39 (dd, Lac-γ, 2H), 2.43 (m, Lac-β, 1H), 1.89 (m, Lac-β, 1H), 1.45 (s, (CH₃)₃COCOLac, 9H), 0.95 (t, Nva-CH₃, 3H).

NMR (41) (300 MHz, CD₃OD): δ 4.61 (dd, Nva-α, 1H), 4.36 (br m, Lac-α, 1H), 3.52 (br t, Lac-γ, 1H), 3.35 (m, Lac-γ, 1H), 2.44 (m, Lac-β, 1H), 1.91 (m, Lac-β, 1H), 1.44 (s, Boc, 9H), 0.96 (t, Nva-CH₃, 3H).

Step 4
Preparation of Boc-(S)-γ-Lactam-Nva-Leu-NH₂ (42)

267 mg of (41) (0.88 mmole), product of Step 3, was dissolved in 5 mL CH₂Cl₂, after which was added 120 mg HOBT and 170 mg EDC (0.88 mmole each). The activated ester complex was stirred for 5 min, after which 147 mg (0.88 mmole) of leucine carboxamide HCl and 153 μL (0.88 mmole) DIEA was added, and the reaction stirred overnight. The reaction mixture was diluted with CH₂Cl₂ and washed twice each with 5% citric acid and 5% NaHCO₃. The organic layer was dried over Na₂SO₄, filtered, and the filtrate was evaporated by rotary evaporation. The crude isolate was purified by flash silica gel chromatography. The residue was pumped on high vacuum overnight to give the title compound. NMR (300 MHz, CD₃OD): δ 4.63 (dd, Nva-α, 1H), 4.36 (dd, Leu-α, 1H), 4.07 (t, Lac-α, 1H), 3.39 (m, Lac-γ, 2H), 2.44 (m, Lac-β, 1H), 1.45 (s, Boc, 9H), 0.95 (t, Nva-CH₃, 3H), 0.95 (d, Leu-CH₃, 3H), 0.90 (d, Leu-CH₃, 3H).

Step 5
Preparation of HCl.H₂N-(S)-γ-Lactam-Nva-Leu-NH₂ (43)

225 mg of (42) (0.55 mmole), product of Step 4, was dissolved in 3 mL of 4N HCl in dioxane and the mixture allowed to stir. After 2 h the dioxane was evaporated and the residue pumped on high vacuum to give the title compound. NMR (300 MHz, CD₃OD): δ 4.59 (dd, Nva-α, 1H), 4.36 (dd, Leu-α, 1H), 4.12 (t, Lac-α, 1H), 3.80 (t, Lac-γ, 1H), 3.48 (m, Lac-γ, 1H), 2.57 (m, Lac-β, 1H), 0.96 (t, Nva-CH₃, 3H), 0.96 (d, Leu-CH₃, 3H), 0.91 (d, Leu-CH₃, 3H).

Step 6
Preparation of EtOCO-Phe-(S)-γ-Lactam-Nva-Leu-NH₂ (44)

The title compound was made by acylating (43), the product of Step 5, with EtOCO-Phe followed by purification via silica gel chromatography. NMR (500 MHz, CD₃OD): δ 7.24 (m, Ph, 5H), 4.60 (dd, Nva-α, 1H), 4.35 (m, Leu-α & Phe-α, 2H), 4.23 (q, Lac-α,1H), 4.00 (q, CH₃CH₂OCO, 2H), 3.47 (m, Lac-γ, 2H), 3.14 (dd, Phe-β, 1H), 2.86 (dd, Phe-β, 1H), 2.40 (m, Lac-β, 1H), 1.99 (m, Lac-β & Leu-β, 2H), 1.17 (t, CH₃CH₂OCO, 3H), 0.97 (dd, Leu-CH₃, 3H), 0.96 (t, Nva-CH₃, 3H), 0.92 (dd, Leu-CH₃, 3H). Mass spectrum [FAB]: 532.1 (M+1).

EXAMPLE 22

EtOCO-Cha-(S)-γ-Lactam-Nva-Leu-NH₂ (45)

The title compound was made by acylating (43), the product of Example 21, Step 5, with EtOCO-Cha followed by silica gel chromatography. NMR (500 MHz, CD₃OD): δ

4.61 (dd, Nva-α, 1H), 4.34 (m, Leu-α, 1H), 4.22 (m, Lac-α), 4.15 (dd, Cha-α, 1H), 4.06 (m, CH₃CH₂OCO, 2H), 3.43 (br t, Lac-γ, 2H), 2.47 (m, Lac-β, 1H), 2.06 (m, Lac-β, 1H), 2.02 (m, Cha-β, 1H), 1.22 (t, CH₃CH₂OCO, 3H), 0.96 (t, Nva-CH₃, 3H), 0.95 (d, Leu-CH₃, 3H), 0.91 (d, Leu-CH₃, 3H). Mass spectrum [FAB]: 538.2 (M+1).

EXAMPLE 23 cHx(CH₂)₃-(S)-γ-Lactam-Nva-Leu-NH₂ (46)

10 μL (57 μmole) of 3-cyclohexyl-1-propanal, 20 mg (57.4 μmole) of (43), the product of Example 21, Step 5, excess sodium cyanoborohydride (ca. 7 mg) and 10 μL (57 μmole) of DIEA were combined in 1 mL methanol to give the title compound after NaHCO₃ workup and silica gel chromatography. NMR (500 MHz, CD₃OD): δ 4.59 (dd, Nva-α, 1H), 4.36 (dd, Leu-α, 1H), 3.57 (dt, Lac-α, 1H), 3.51 (dd, Lac-γ, 1H), 3.36 (m, Lac-γ, 1H), 2.67 (m, CH₂CH₂CH₂cHx, 1H), 2.56 (m, CH₂CH₂CH₂cHx, 1H), 2.37 (m, Lac-β, 1H), 1.83 (m, Lac-β, 1H), 0.96 (t, Nva-CH₃, 3H), 0.96 (d, Leu-CH₃, 3H), 0.90 (d, Leu-CH₃, 3H). Mass spectrum [FAB]: 437.1 (M+1).

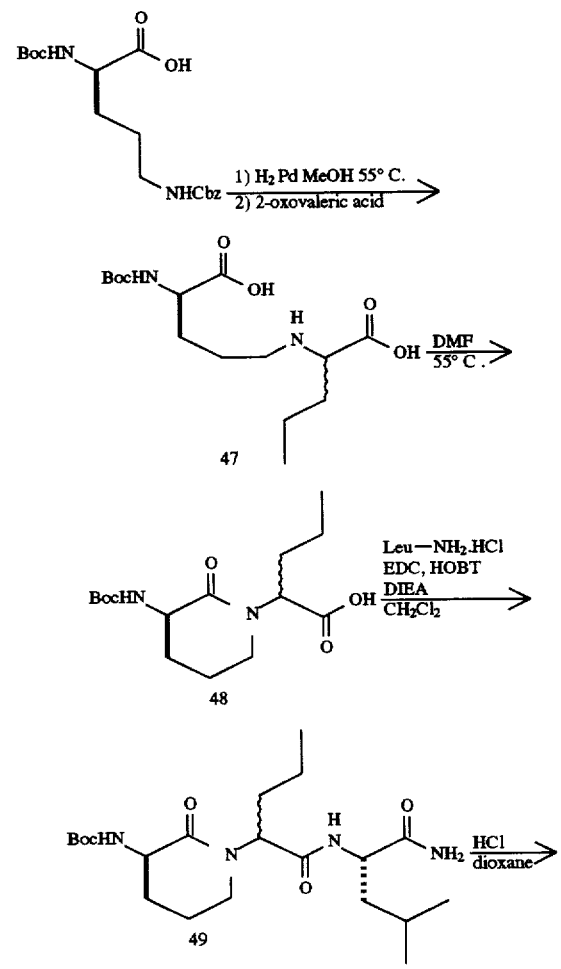

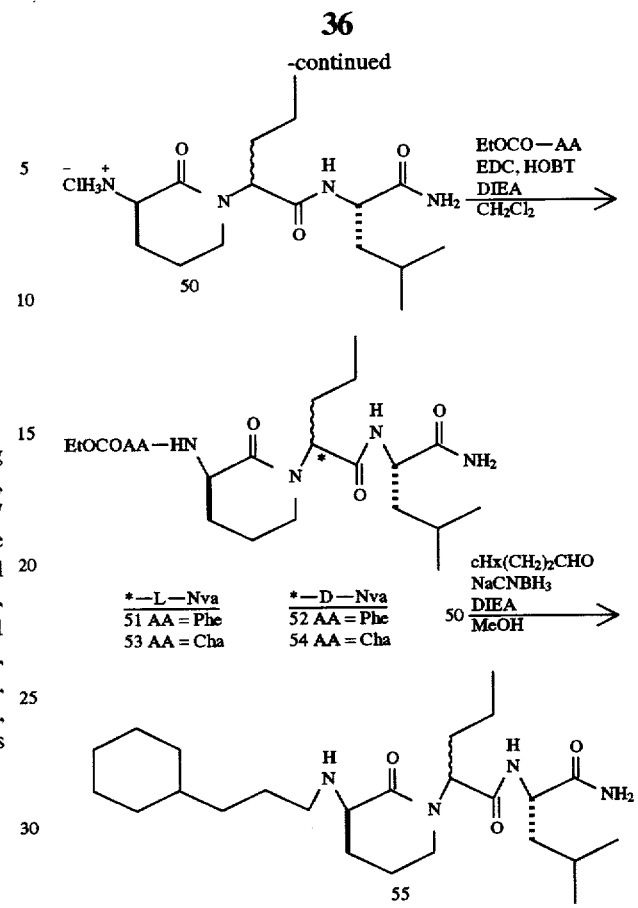

EXAMPLE 24

BtOCO-Phe-(R)-δ-Lactam-L-Nva-Leu-NH₂ and EtOCO-Phe-(R)-δ-Lactam-D-Nva-Leu-NH₂ (51 and 52)

Step 1
Preparation of Boc-D-Orn(CHPr(COOH))-OH (47)

915 mg (2.5 mmole) of commercially available Boc-D-Orn(Cbz)-OH was dissolved in 10 mL methanol and the reaction vessel was evacuated and charged with N₂. 100 mg of palladium black was added and the vessel was evacuated and charged with H₂. the reaction was heated to 55° C. for 2 h. TLC monitoring indicated that the reaction was not complete, so it was stirred at room temperature overnight. After 16 h, no change was noted by TLC, so another 50 mg of palladium black was added and the reaction was heated to 55° C. for 3 h. TLC showed that the hydrogenolysis was ca. 80% complete. At this stage, 290 mg (2.5 mmole) of 2-oxovaleric acid was added and the reaction was stirred overnight. Another 100 mg 2-oxovaleric acid was added when TLC showed that the reductive amination was not complete, and the reaction was stirred another 24 h. The reaction was then filtered over Celite™ diatomaceous earth and the filtrate evaporated by rotary evaporation. The title compound was crystallized from methanol/Et₂O. NMR (400 MHz, CD₃OD): δ4.08 (m, Ore-co, 1H), 3.48 (t, NHCHPr (COOH), 1H), 2.98 (m, Orn-δ, 2H), 1.42 (s, Boc, 9H), 0.95 (t, CHCH₂CH₂CH₃, 3H).
Step 2
Preparation of Boc-(R)-δ-Lactam-D,L-Nva (48)

380 mg (1.15 mmole), Step 1, of (47) was dissolved in 10 mL of dry DMF and heated to 55° C. for 6 h. The reaction was then stirred at room temperature for an additional 72 h, after which the DMF was stripped by high vacuum rotary evaporation. The title compound was recovered by crystallization from ethyl acetate/hexanes. NMR (300 MHz, CD$_3$OD): δ4.96 (dd, Nva-α, 1H), 4.04 (t, Lac-α, 1H), 3.30 (m, Lac-δ, 2H), 2.11 (m, Lac-β, 1H), 1.42 (s, Boc, 9H), 0.93 (t, Nva-CH$_3$, 3H).

Step 3

Preparation of Boc-(R)-δ-Lactam-D,L-Nva-Leu-NH$_2$ (49)

119 mg (0.38 mmole) of (48), the product of Step 2, was dissolved in 2 mL of CH$_2$Cl$_2$, after which was added 56.7 mg HOBT and 80.6 mg EDC (0.42 mmole, 1.1 eq. each). After stirring the activated ester complex for 5 min, 63.5 mg (0.38 mmole) of leucine carboxamide HCl and 66 µL (0.38 mmole) of DIEA were added. TLC monitoring after 90 min showed the reaction was only about 50% complete, so another 66 µL DIEA, 15 mg HOBT, and 20 mg EDC were added. The reaction was allowed to stir overnight. The reaction mixture was then diluted with 15 mL CH$_2$Cl$_2$ and washed 2× each with 5% citric acid and 5% NaHCO$_3$. The organic layer was dried over Na$_2$SO$_4$, filtered, and the filtrate evaporated by rotary evaporation. TLC indicated that the crude material was ca. 2:1 mix of diastereomers but was otherwise pure (confirmed by NMR). The title compound was recovered. NMR (300 MHz, CD$_3$OD): δ 5.03 (br dd & dd, Nva-α, 1H), 4.36, (t, Leu-α, 1H), 4.01 (2 m, Lac-δ, 1H), 3.30 (m, Lac-δ, 2H), 2.08 (m, Lac-β, 1H), 1.44 (s, Boc, 9H), 0.94 (t & d, Nva-CH$_3$ & Leu-CH$_3$, 6H), 0.90 (d, Leu-CH$_3$, 3H).

Step 4

Preparation of HCl.H$_2$N-(R)-δ-Lactam-D,L-Nva-Leu-NH$_2$ (50)

129 mg (0.30 mmole) of (49), the product of Step 2, was dissolved in 1 mL of 4N HCl in dioxane and allowed to stir while monitored by TLC. After 45 min the solvent was stripped by rotary evaporation. The residue was triturated with ether and the ether decanted to give the title compound. NMR (300 MHz, CD$_3$OD): δ 5.01 & 4.91 (2 m, Nva-α, 1H), 4.37, (m, Leu-α, 1H), 3.98 (m, Lac-β, 1H), 3.43 (m, Lac-δ, 1H), 3.30 (m, Lac-δ, 1H), 2.28 (m, Lac-α, 1H), 0.96 (t & d, Nva-CH$_3$ & Leu-CH$_3$, 6H), 0.92 (d, Leu-CH$_3$, 3H).

Step 5

Preparation of EtOCO-Phe-(R)-δ-Lactam-L-Nva-Leu-NH$_2$ and EtOCO-Phe-(R)-δ-Lactam-D-Nva-Leu-NH$_2$ (51 and 52)

The title compounds (51) and (52) were made by acylating (50), the product of Step 3, with EtOCO-Phe followed by silica gel chromatography purification to separate the two diastereomers.

Less polar isomer: NMR (500 MHz, CD$_3$OD): δ 7.24 (m, Ph, 5H), 4.99 (dd, Nva-α, 1H), 4.36 (m, Phe-α & Leu-α, 2H), 4.22 (dd, Lac-α, 1H), 4.00 (q, CH$_3$CH$_2$OCO, 2H), 3.38 (m, Lac-δ, 1H), 3.30 (m, Lac-δ), 3.12 (dd, Phe-β, 1H), 2.87 (dd, Phe-β, 1H), 1.16 (t, CH$_3$CH$_2$OCO, 3H), 0.96 (t, Nva-CH$_3$, 3H), 0.96 (d, Leu-CH$_3$, 3H), 0.91 (d, Leu-CH$_3$, 3H). Mass spectrum [FAB]: 546.2 (M+1).

More polar isomer: NMR (500 MHz, CD$_3$OD): δ 7.24 (m, Ph, 5H), 4.93 (dd, Nva-α, 1H), 4.38 (m, Phe-α & Leu-α, 2H), 4.32 (dd, Lac-α, 1H), 4.00 (q, CH$_3$CH$_2$OCO, 2H), 3.34 (m, Lac-δ, 2H), 3.13 (dd, Phe-β, 1H), 2.87 (dd, Phe-β, 1H), 1.17 (t, CH$_3$CH$_2$OCO, 3H), 0.97 (t, Nva-CH$_3$, 3H), 0.96 (d, Leu-CH$_3$, 3H), 0.90 (d, Leu-CH$_3$, 3H). Mass spectrum [FAB]: 546.2 (M+1).

EXAMPLE 25

EtOCO-Cha-(R)-δ-Lactam-L-Nva-Leu-NH$_2$ and EtOCO-Cha-(R)-δ-Lactam-D-Nva-Leu-NH$_2$ (53 and 54)

The title compounds (53) and (54) were made by acylating (50), the product of Example 24, Step 3, with EtOCO-Cha followed by silica gel chromatography to separate the two diastereomers.

Less polar isomer: NMR (500 MHz, CD$_3$OD): δ 5.03 (dd, Nva-α, 1H), 4.38 (dd, Lac-α, 1H), 4.16 (m, Cha-α & Leu-α, 2H), 4.10 (q, CH$_3$CH$_2$OCO, 2H), 3.35 (m, Lac-δ, 2H), 1.24 (t, CH$_3$CH$_2$OCO, 3), 0.96 (t, Nva-CH$_3$, 3H), 0.96 (d, Leu-CH$_3$, 3H), 0.92 (d, Leu-CH$_3$, 3H). Mass spectrum [FAB]: 552.2 (M+1).

More polar isomer: NMR (500 MHz, CD$_3$OD): δ 4.93 (dd, Nva-α, 1H), 4.28 (m, Cha-α & Leu-α, 2H), 4.17 (dd, Lac-α, 1H), 4.08 (q, CH$_3$CH$_2$OCO, 2H), 3.36 (m, Lac-δ, 2H), 1.24 (t, CH$_3$CH$_2$OCO, 3H), 0.95 (t, Nva-CH$_3$, 3H), 0.95 (d, Leu-CH$_3$, 3H), 0.90 (d, Leu-CH$_3$, 3H). Mass spectrum [FAB]: 552.2 (M+1).

EXAMPLE 26 cHx(CH$_2$)$_3$-(R)-δ-Lactam-D,L-Nva-Leu-NH$_2$ (55)

10 µL (57 µmole) of 3-cyclohexyl-1-propanal, 20 mg (57.4 µmole) of (50), product of Example 24, Step 3, excess sodium cyanoborohydride (ca. 7 mg) and 10 µL (57 µmole) of DIEA were combined in 1 mL methanol to give 6.6 mg (26% yield) of the title compound after NaHCO$_3$ workup and silica gel chromatography. The diastereomers were not separable in the solvent system that was used. NMR (500 MHz, CD$_3$OD): δ 5.06 (dd, Nva-α, 1H), 4.37 (ddd, Leu-α, 1H), 3.42 (ddd, Lac-α, 1H), 3.36 (m, Lac-δ, 1H), 3.28 (m, Lac-δ, 1H), 2.57 (dt, CH$_2$CH$_2$CH$_2$cHx, 2H), 0.96 (m, 2xLeu-CH$_3$, 6H), 0.91 (t, Nva-CH$_3$, 3H). Mass spectrum [FAB]: 451.2 (M+1).

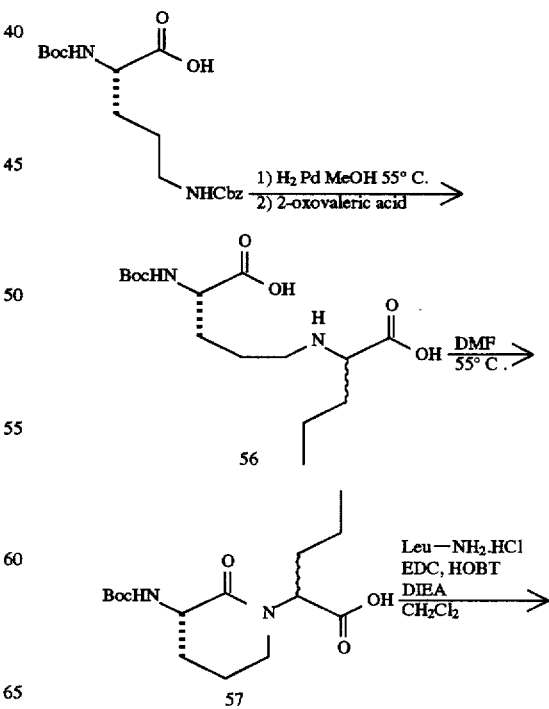

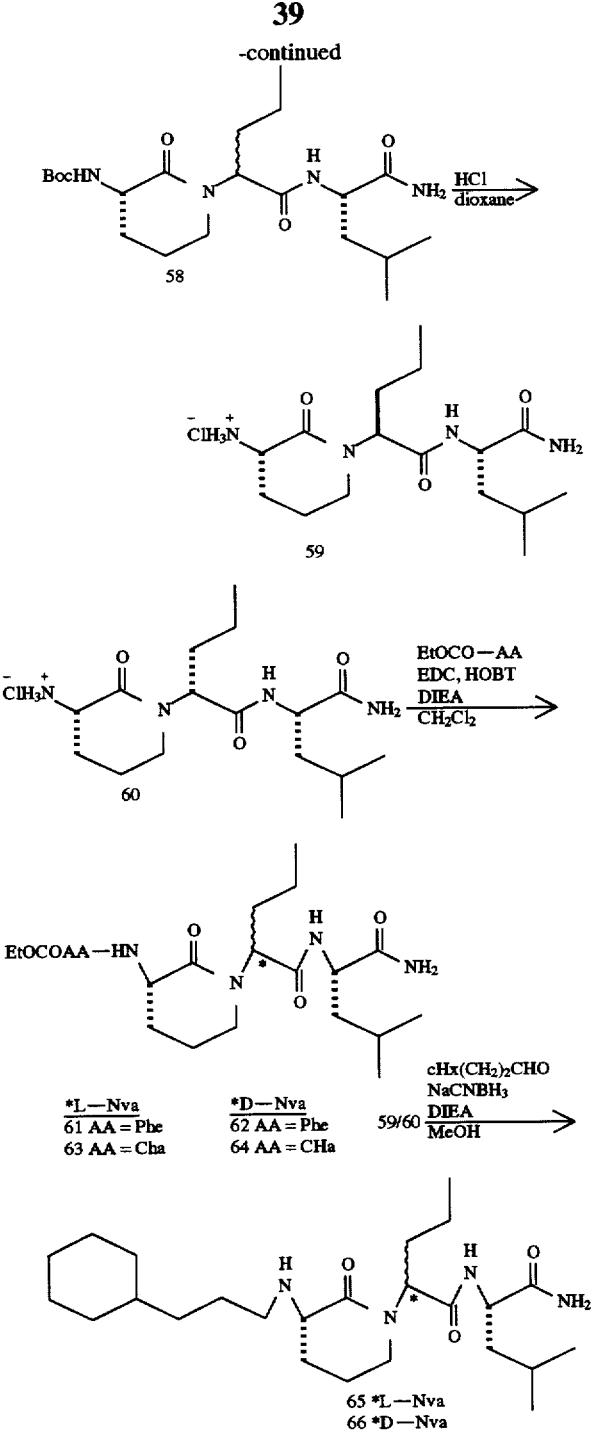

EXAMPLE 27

EtOCO-Phe-(S)-δ-Lactam-L-Nva-Leu-NH₂ and
EtOCO-Phe-(S)-δ-Lactam-D-Nva-Leu-NH₂
(61 and 62)

Step 1
Preparation of Boc-L-Orn(NHCHPr(COOH))-OH (56)

915 mg (2.5 mmole) of Boc-L-Orn(Cbz) was dissolved in 10 mL methanol and the reaction vessel was evacuated and charged with N₂. 100 mg of palladium black was added and the vessel evacuated. It was charged with H₂ and stirred at room temperature overnight. TLC indicated that the hydrogenolysis was complete, so 345 mg (3.75 mmole, 1.5 eq) of 2-oxovaleric acid was added and the reaction was stirred overnight. The reaction was then filtered over Celite™ (diatomaceous earth) and the filtrate evaporated by rotary evaporation. The crude residue was directly used in the lactam cyclization. NMR (400 MHz, CD₃OD): δ 4.08 (m, Orn-α, 1H), 3.51 (t, NHCHPr(COOH), 1H), 2.98 (m, Orn-α, 2H), 1.42 (s, Boc, 9H), 0.96 (t, CHCH₂CH₂CH₃, 3H).

Step 2
Preparation of Boc-(S)-δ-Lactam-D,L-Nva (57)

960 mg (2.5 mmole plus impurities, product of Step 1) of (56) was dissolved in 30 mL of dry DMF and heated to 55° C. for 3.5 h. The reaction was then heated to 75° C. for 1 h, after which the DMF was stripped by high vacuum rotary evaporation. The title compound was recovered by crystallization from ethyl acetate/hexanes. NMR (300 MHz, CD₃OD): δ 4.97 (dd, Nva-α, 1H), 4.07 (dd, Lac-α, 1H), 3.30 (m, Lac-δ, 2H), 2.12 (m, Lac-β, 1H), 1.43 (s, Boc, 9H), 0.95 (t, Nva-CH₃, 3H).

Step 3
Preparation of Boc-(S)-δ-Lactam-D,L-Nva-Leu-NH₂ (58)

157 mg (0.50 mmole, product of Step 2) of (57) was dissolved in 2.5 mL of CH₂Cl₂, after which was added 69 mg HOBT and 96 mg EDC (0.50 mmole each). After stirring the activated ester complex for 20 min, 84 mg (0.50 mmole) of leucine carboxamide HCl and 87 µL (0.50 mmole) of DIEA were added. TLC monitoring after 16 h showed the reaction was only about 50% complete, so another 87 µL DIEA, 36 mg HOBT, and 46 mg EDC were added. The reaction was allowed to another 2 h. The reaction mixture was then diluted with 15 mL CH₂Cl₂ and washed 2× each with 5% citric acid and 5% NaHCO₃. The organic layer was dried over Na₂SO₄, filtered, and the filtrate evaporated by rotary evaporation. TLC indicated that the crude material was a mix of diastereomers but was otherwise pure (confirmed by NMR). The title compound was recovered. NMR (300 MHz, CD₃OD): δ 5.20 & 4.70 (dd & m, Nva-α, 1H), 4.36, (m, Leu-α, 1H), 3.96 & 3.85 (2 m, Lac-α, 1H), 3.40 (m, Lac-δ, 1H), 3.30 (m, Lac-δ, 1H), 2.09 (m, Lac-β, 1H), 1.44 (s, Boc, 9H), 0.95 (t & d, Nva-CH₃ & Leu-CH₃, 6H), 0.90 (d, Leu-CH₃, 3H).

Step 4
Preparation of HCl.H₂-N-(S)-δ-Lactam-D-Nva-Leu-NH₂ and HCl.H₂N-L-δ-Lactam-L-Nva-Leu-NH₂. (59 and 60)

128 mg (0.30 mmole, product of Step 3) of (58) was dissolved in 1.5 mL of 4N HCl in dioxane and allowed to stir while monitored by TLC. After 45 min the solvent was stripped by rotary evaporation. The title compounds were separated by multiple flash silica gel chromatographies, but were not assigned stereochemically.

Less polar isomer: NMR (300 MHz, CD₃OD): δ4.94 (dd, Nva-α, 1H), 4.36, (dd, Leu-α, 1H), 3.36 (m, Lac-α & Lac-δ, 3H), 2.15 (m, Lac-β, 1H), 0.96 (t, Nva-CH₃, 3H), 0.95 (d, Leu-CH₃, 3H), 0.86 (d, Leu-CH₃, 3H).

More polar isomer: NMR (300 MHz, CD₃OD): δ 4.90 (dd, Nva-α, 1H), 4.37, (dd, Leu-α, 1H), 3.40 (m, Lac-α & Lac-β, 3H), 2.15 (m, Lac-β, 1H), 0.96 (t, Nva-CH₃, 3H), 0.96 (d, Leu-CH₃, 3H), 0.86 (d, Leu-CH₃, 3H).

Step 5
Preparation of EtOCO-Phe-(S)-δ-Lactam-L-Nva-Leu-NH₂ and EtOCO-Phe-(S)-δ-Lactam-D-Nva-Leu-NH₂ (61 and 62)

The title compounds (61) and (62) were made by acylating (59) and (60), the products of Step 4, with EtOCO-Phe followed by silica gel chromatography.

Less polar isomer: NMR (500 MHz, CD₃OD): δ 7.24 (m, Ph, 5H), 5.15 (dd, Nva-α, 1H), 4.36 (m, Phe-α & Leu-α, 2H), 4.04 (dd, Lac-α, 1H), 4.00 (q, CH₃CH₂OCO, 2H), 3.31 (m, Lac-δ, 2H), 3.16 (dd, Phe-β, 1H), 2.85 (dd, Phe-β, 1H), 1.17 (t, CH$_3$CH$_2$OCO, 3H), 0.96 (t, Nva-CH$_3$, 3H), 0.96 (d, Leu-CH$_3$, 3H), 0.92 (d, Leu-CH$_3$, 3H). Mass spectrum [FAB]: 546.2 (M+1).

More polar isomer: NMR (500 MHz, CD$_3$OD): δ 7.25 (m, Ph, 5H), 4.63 (dd, Nva-α, 1H), 4.35 (m, Phe-α & Leu-α, 2H), 4.17 (dd, Lac-α, 1H), 3.99 (q, CH$_3$CH$_2$OCO, 2H), 3.43 (m, Lac-δ, 2H), 3.17 (dd, Phe-β, 1H), 2.82 (dd, Phe-β, 1H), 1.16 (t, CH$_3$CH$_2$OCO, 3H), 0.97 (t, Nva-CH$_3$, 3H), 0.97 (d, Leu-CH$_3$, 3H), 0.92 (d, Leu-CH$_3$, 3H). Mass spectrum [FAB]: 546.2 (M+1).

EXAMPLE 28

EtOCO-Cha-(S)-δ-Lactam-L-Nva-Leu-NH$_2$ and EtOCO-Cha-(S)-δ-Lactam-D-Nva-Leu-NH$_2$ (63 and 64)

The title compounds (63) and (64) were made by acylating (59) and (60), the products of Example 27, Step 4 with EtOCO-Cha followed by silica gel chromatography.

Less polar isomer: NMR (500 MHz, CD$_3$OD): δ 5.15 (dd, Nva-α, 1H), 4.34 (dd, Lac-α, 1H), 4.15 (m, Leu-α, 1H), 4.10 (m, Cha-α & CH$_3$CH$_2$OCO, 3H), 3.30 (m, Lac-δ, 2H), 1.23 (t, CH$_3$CH$_2$OCO, 3H), 0.95 (t, Nva-CH$_3$, 3H), 0.94 (d, Leu-CH$_3$, 3H), 0.91 (d, Leu-CH$_3$, 3H). Mass spectrum [FAB]: 552.2 (M+1).

More polar isomer: NMR (500 MHz, CD$_3$OD): δ 4.50 (dd, Nva-α, 1H), 4.34 (m, Leu-α, 1H), 4.13 (m, Lac-α, 1H), 4.09 (q, CH$_3$CH$_2$OCO, 2H), 3.42 (m, Lac-δ, 2H), 1.26 (t, CH$_3$CH$_2$OCO, 3H), 0.96 (t, Nva-CH$_3$, 3H), 0.96 (d, Leu-CH$_3$, 3H), 0.91 (d, Leu-CH$_3$, 3H). Mass spectrum [FAB]: 552.2 (M+1).

EXAMPLE 29 cHx(CH$_2$)$_3$-(S)-δ-Lactam-L-Nva-Leu-NH$_2$ and cHx(CH$_2$)$_3$-(S)-δ-Lactam-D-Nva-Leu-NH$_2$ (65 and 66)

1 eq. 3-cyclohexyl-1-propanal, 1 eq. of (59) and (60) (separately, products of Example 27, Step 4), excess sodium cyanoborohydride and 1 eq. of DIEA were combined in 0.5 mL methanol to give the title compounds after NaHCO$_3$ workup and silica gel chromatography.

Less polar isomer: NMR (500 MHz, CD$_3$OD): a 4.94 (dd, Nva-α, 1H), 4.36 (dd, Leu-α, 1H), 3.35 (dd, Lac-δ, 2H), 3.28 (dd, Lac-α, 1H), 2.58 (t, CH$_2$CH$_2$CH$_2$cHx, 2H), 0.95 (t, Nva-CH$_3$, 3H), 0.95 (d, Leu-CH$_3$, 3H), 0.90 (d, Leu-CH$_3$, 3H). Mass spectrum [FAB]: 451.2 (M+1).

More polar isomer: NMR (500 MHz, CD$_3$OD): δ 4.95 (dd, Nva-α, 1H), 4.38 (dd, Leu-α, 1H), 3.42 (m, Lac-α, 1H), 3.32 (m, Lac-δ, 2H), 2.58 (t, CH$_2$CH$_2$CH$_2$cHx, 2H), 0.97 (t, Nva-CH$_3$, 3H), 0.97 (d, Leu-CH$_3$, 3H), 0.92 (d, Leu-CH$_3$, 3H). Mass spectrum [FAB]: 451.2 (M+1).

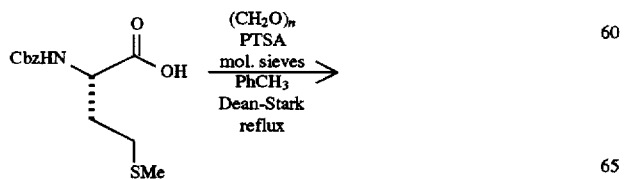

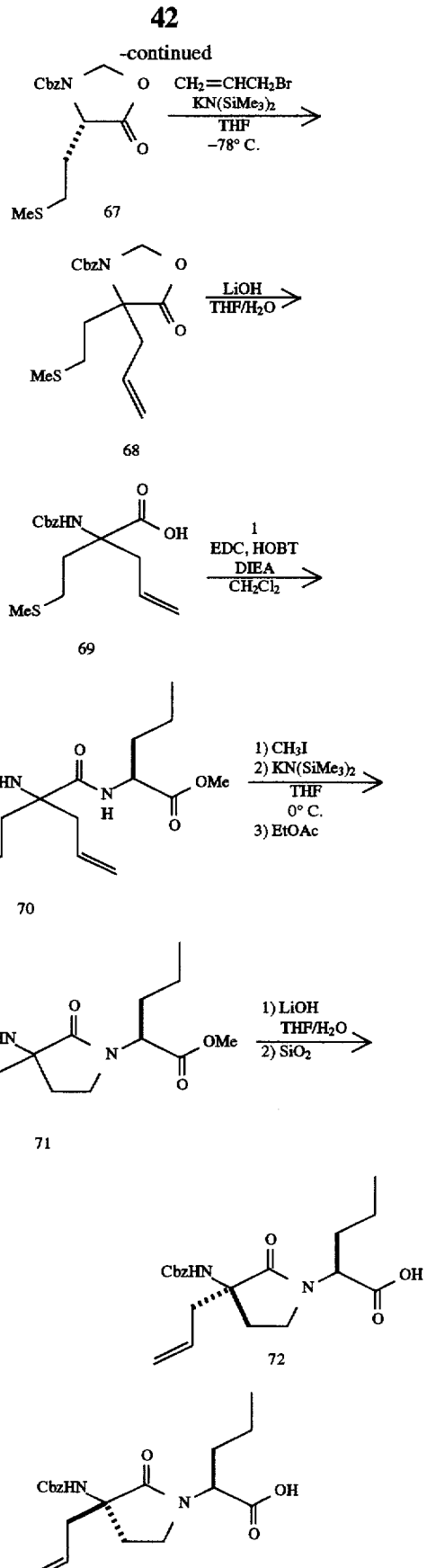

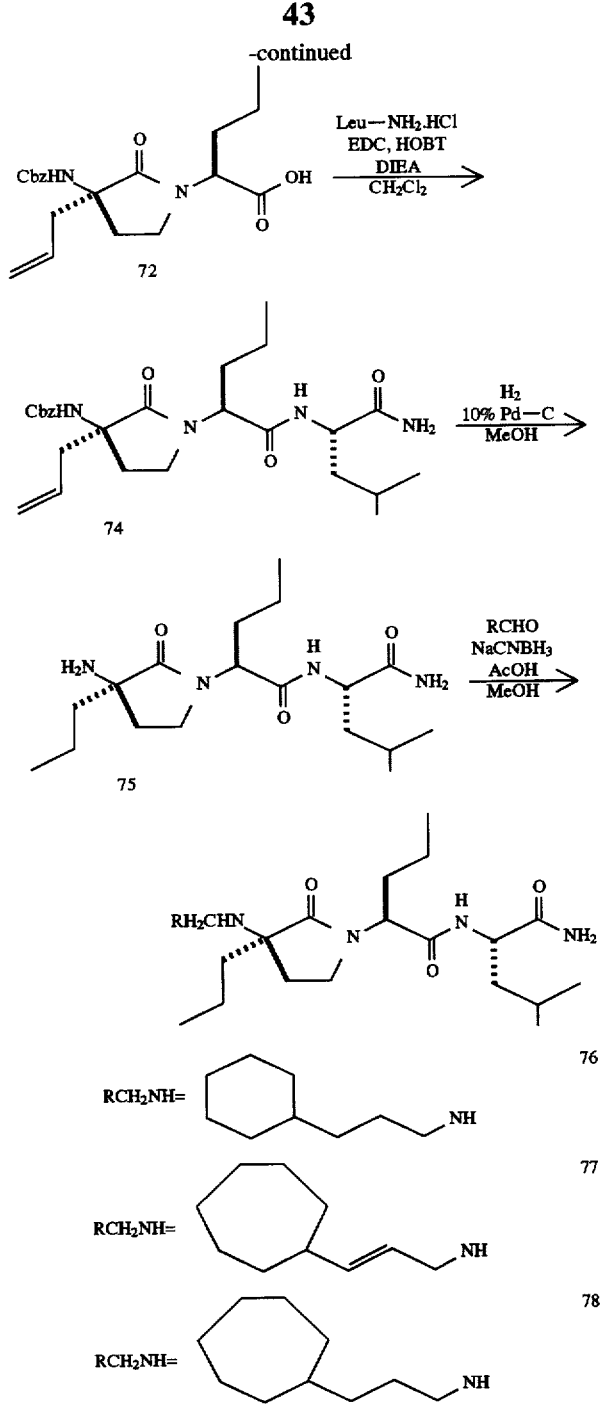

EXAMPLE 30 cHx(CH$_2$)$_3$-α-Propyl-(R)-γ-Lactam-Nva-Leu-NH$_2$ (76)

Step 1
Preparation of 3-N-Cbz-4(S)-(3-Thiobutyl)-Oxazolidinone (67)

10.0 g (35.2 mmole) of Cbz-L-methionine was dissolved in 150 mL of toluene. 4 g of 3 Å molecular sieves, 3.0 g (100 mmole) of paraformaldehyde, and 640 mg of p-toluenesulfonic acid (3.3 mmole) were then added to the stirring solution. The flask was fitted with a Dean-Stark trap and a reflux condenser. The solution was heated to reflux until water had ceased azeotroping for 1 h. The reaction was cooled to room temperature, diluted with Et$_2$O, and washed 2× with saturated NaHCO$_3$ and 2× with brine. The organic was dried over Na$_2$SO$_4$, filtered, and the filtrate evaporated. The crude oil was pumped on high vacuum overnight to remove residual toluene to give the title compound. NMR (300 MHz, CDCl$_3$): δ 7.35 (m, Ph, 5H), 5.55 (br, NCH$_2$O, 1H), 5.28 (d, NCH$_2$O, 1H), 5.20 (dd, OCH$_2$Ph, 2H), 4.38 (t, CHCH$_2$CH$_2$SCH$_3$, 1H), 2.54 (m, CHCH$_2$CH$_2$SCH$_3$, 2H), 2.24 (br m, CHCH$_2$CH$_2$SCH$_3$, 2H), 2.03 (br s, CHCH$_2$CH$_2$SCH$_3$, 3H).

Step 2
Preparation of 3-N-Cbz-4-(3-Thiobutyl)-4-allyl-Oxazolidinone (68)

4.97 g (16.8 mmole) of (67), the product of Step 1, was added to a time dried flask and dissolved in 42 mL of freshly distilled THF. The flask was evacuated and charged with N$_2$, then cooled to −78° C. and stirred at that temperature for 30 min. 1.85 mL (20.2 mmole, 1.2 eq) of allyl iodide and 40.5 mL of 0.5N potassium bis(trimethyl-silyl)amide in toluene (20.2 mmole, 1.2 eq) were then added. TLC monitoring showed the reaction was complete within 20 min, so the reaction was quenched with a large excess (ca. 50 mL) of aqueous NH$_4$Cl, then brought to room temperature. The reaction was then extracted 3× with ethyl acetate. The combined organics were dried over Na$_2$SO$_4$, filtered, and the filtrate evaporated. The title compound was isolated by silica gel chromatography. NMR (400 MHz, CDCl$_3$): δ 7.35 (m, Ph, 5H), 5.55 (m, CCH$_2$CH=CH$_2$, 1H), 5.30–4.90 (m, NCH$_2$O, OCH$_2$Ph, CCH$_2$CH=CH$_2$, 6H), 1.99 & 1.95 (2 s, CHCH$_2$CH$_2$SCH$_3$, 3H).

Step 3
Preparation of (+)-Cbz-α-Allyl Methionine (69)

3.09 g (9.2 mmole) of (68), the product of Step 2, was dissolved in 80 mL of THF. 40 mL of 0.5N LiOH was then added and the reaction monitored by TLC. The THF was evaporated by rotary evaporation, extracted 1× with CH$_2$Cl$_2$, the extract discarded, and the remaining aqueous layer acidified with 2N HCl. The aqueous was then extracted 3× with CH$_2$Cl$_2$, the combined extracts dried over Na$_2$SO$_4$, filtered, and the filtrate evaporated to give the racemic title compound. NMR (400 MHZ, CD$_3$OD, 55° C.): δ 7.32 (m, Ph, 5H), 5.65 (m, CH$_2$CH=CH$_2$, 1H), 5.05 (s, PhCH$_2$O & CH$_2$CH-CH$_2$, 3H), 5.02 (dd, CH$_2$CH=CH$_2$, 1H), 2.01 (s, Met-CH$_3$, 3H).

Step 4
Preparation of Cbz-α-Allyl-Met-Nva methyl ester (70)

2.95 g (9.1 mmole) of (69), the product of Step 3, 45 mL of CH$_2$Cl$_2$, 1.47 g HOBT and 2.09 g EDC (10.9 mmole, 1.2 eq. each) were stirred for 10 min, then 1.53 g (9.1 mmole) of (1), from Example 1, Step 1, and 1.59 mL (9.1 mmole) of DIEA were added and the reaction was stirred 16 h. The reaction mixture was washed 2× with 5% citric acid, 2× with 5% NaHCO$_3$, and 1× with brine. The organic layer was dried over Na$_2$SO$_4$, filtered, the filtrate evaporated and pumped on high vacuum to give the title compound. NMR (400 MHz, CD$_3$OD): δ 7.33 (m, Ph, 5H), 5.63 (m, CH$_2$CH=CH$_2$, 1H), 5.05 (s & m, PhCH$_2$O & CH$_2$CH=CH$_2$, 4H), 4.37 (dd, Nva-α, 1H), 3.68 (s, COOCH$_3$, 3H), 2.01 (s, Met-CH$_3$, 3H), 0.91 (dt, Nva-CH$_3$, 3H).

Step 5
Preparation of Cbz-α-Allyl-(R,S)-γ-Lactam-Nva methyl ester (71)

3.68 g (8.4 mmole) of (70), the product of Step 4, was dissolved in 18 mL of iodomethane and stirred for 36 h. The iodomethane was then evaporated and the residue pumped on high vacuum for 45 min. It was then transferred to a flame-dried flask and dissolved in 185 mL of THF and cooled to 0° C. After 20 min, 16.9 mL of 0.5N potassium bis(trimethylsilyl)amide in toluene (8.4 mmole) was added over 2 min. After 75 min the reaction was quenched with 125 mL ethyl acetate, then after 10 min aqueous $NH_4Cl$ was added. The solution was then transferred to a separatory funnel, the aqueous layer separated, and the organic washed a second time with $NH_4Cl$. The combined aqueous layers were extracted a second time with ethyl acetate, and the combined organics were then dried over $Na_2SO_4$. The organic layer was filtered and the solvent stripped by rotary evaporation. The title compound was isolated by silica gel chromatography. NMR (400 MHz, $CD_3OD$): δ 7.30 (m, Ph, 5H), 5.82 (m, $CH_2CH=CH_2$, 1H), 5.16 (d & dd, $CH_2CH=CH_2$, 2H), 5.02 (s, $PhCH_2O$, 2H), 4.71 & 4.54 (2 dd, Nva-α, 0.5 H each), 3.70 (s, $COOCH_3$, 3H), 3.56 (dt, Lac-γ, 1H), 3.32 (t, Lac-γ, 1H),2.42 (m, $CH_2CH=CH_2$ & Lac-β, 3H), 2.22 (m, Lac-β, 1H), 0.93 (t, Nva-$CH_3$, 3H).

The lactam cyclization can also be performed using NaH as the base. NaH cyclizations of these lactams produce final products that can be partially epimerized at the norvaline center. Hydrolysis of the methyl ester gives two separable diastereomeric pairs of compounds, and subsequent acylation with L-leucine carboxamide and purification of each pair leads to isolation of all four of the diastereomers. Ester hydrolysis and acylation procedures are analogous to those found below.

Step 6
Preparation of Cbz-α-Allyl-(R)-γ-Lactam-Nva (72) and Cbz-(α-Allyl)-(S)-γ-Lactam-Nva (73)

210 mg (541 μmole) of (71), the product of Step 5, was dissolved in 5 mL THF, and 1.25 mL of 1N LiOH was added. After 80 min the THF was evaporated and the remaining solution was diluted with water and $CH_2Cl_2$. The layers were separated and the organic extracted a second time with aqueous NaOH. The combined aqueous was acidified with HCl and extracted 2× with $CH_2Cl_2$. The $CH_2Cl_2$ was dried over $Na_2SO_4$, filtered, and the filtrate evaporated. The title compounds were isolated by multiple silica gel chromatographies. Compound (72) was assigned as the R-γ-lactam by comparison of its NMR with the R-γ-lactam made by a chiral synthetic method (see (90)&(72)).

(R)-γ-Lactam: NMR (400 MHz, $CD_3OD$): δ 7.31 (m, Ph, 5H), 5.84 (m, $CH_2CH=CH_2$, 1H), 5.16 (d &dd, $CH_2CH=CH_2$, 2H), 5.03 (s, $PhCH_2O$, 2H), 4.68 (dd, Nva-α, 1H), 3.39 (m, Lac-γ, 2H), 2.42 (m, $CH_2CH=CH_2$ & Lac-β, 3H), 2.20 (m, Lac-β, 1H), 0.95 (t, Nva-$CH_3$, 3H). Mass spectrum [FAB]: 375.1 (M+1).

(S)-γ-Lactam: NMR (400 MHz, $CD_3OD$): δ 7.30 (m, Ph, 5H), 5.81 (m, $CH_2CH=CH_2$, 1H), 5.16 (d & dd, $CH_2CH=CH_2$, 2H), 5.03 (s, $PhCH_2O$, 2H), 4.52 (dd, Nva-α, 1H), 3.61 (t, Lac-γ, 1H), 3.30 (m, Lac-γ, 1H), 2.44 (m, $CH_2CH=CH_2$ & Lac-β, 3H), 2.26 (m, Lac-β, 1H), 0.95 (t, Nva-$CH_3$, 3H). Mass spectrum [FAB]: 375.2 (M+1).

Step 7
Preparation of Cbz-α-Allyl-(R)-γ-Lactam Nva-Leu-$NH_2$ (74)

21.2 mg (57 μmole) of (72), a product of Step 6, was dissolved in 0.5 mL $CH_2Cl_2$, after which was added 9.2 mg HOBT and 13.1 mg EDC (68 μmole, 1.2 eq. each). After 10 min of stirring, 9.5 mg (57 μmole) of leucine carboxamide HCl and 10 μL DIEA were added. The reaction mixture was quite murky after 90 min and TLC indicated limited progress, so 0.5 mL of DMF was added to aid dissolution. After 1 h TLC shows the reaction is complete, so it was diluted with 20 mL of $CH_2Cl_2$ and washed 2× each with 5% citric acid and 5% $NaHCO_3$. The organic layer was dried over $Na_2SO_4$, filtered, and the filtrate evaporated and pumped on high vacuum to give the title compound. NMR (400 MHz, $CD_3OD$): δ 7.31 (m, Ph, 5H), 5.75 (m, $CH_2CH=CH_2$, 1H), 5.17 (m, $CH_2CH=CH_2$, 2H), 5.06 (s, $PhCH_2O$, 2H), 4.41 (dd, Nva-α, 1H), 4.35 (dd, Leu-α, 1H), 3.51 (m, Lac-γ, 1H), 3.41 (m, Lac-γ, 1H), 2.37 (m, $CH_2CH=CH_2$ & Lac-β, 3H), 2.21 (m, Lac-β, 1H), 0.96 (t, Nva-$CH_3$, 3H), 0.91 (dd, 2 Leu-$CH_3$, 6H).

Step 8
Preparation of $H_2N$-α-Propyl-(R)-γ-Lactam-Nva-Leu-$NH_2$ (75)

26.6 mg (55 μmole) of (74), the product of Step 7, was dissolved in 1 mL of methanol and 20 mg of 10% palladium on carbon was added. The reaction vessel was evacuated and charged with $H_2$. The reaction was complete within 90 min, so the catalyst was filtered off through Celite™ the diatomaceous earth and the filtrate evaporated and pumped on high vacuum to give the title compound. NMR (400 MHz, $CD_3OD$): δ 4.57 (dd, Nva-α, 1H), 4.38 (dd, Leu-α, 1H), 3.42 (m, Lac-γ, 2H), 2.14 (m, Lac-β, 1H), 1.88 (m, Lac-β, 1H), 0.96 (t, Nva-$CH_3$, 3H), 0.94 (d, Leu-$CH_3$, 3H), 0.91 (t, -$CH_2CH_2CH_3$, 3H), 0.89 (d, Leu-$CH_3$, 3H). Mass spectrum [FAB]: 355.3 (M+1).

Step 9
Preparation of cHx$(CH_2)_3$-α-Propyl-(R)-γ-Lactam-Nva-Leu-$NH_2$ (76)

3.7 μL (24 μmole) of 3-cyclohexyl-1-propanal, 8.5 mg (24 mmole) of (75), the product of Step 8, 48 μL (48 μmole, 2.0 eq) of 1N sodium cyanoborohydride and 0.7 μL (12 μmole, 0.5 eq.) of AcOH were combined in 0.25 mL methanol to give the title compound after $NaHCO_3$ workup and silica gel chromatography. NMR (500 MHz, $CD_3OD$): δ 4.62 (dd, Nva-α, 1H), 4.37 (dd, Leu-α, 1H), 3.44 (m, Lac-γ, 2H), 2.51 (m, $CH_2CH_2CH_2cHx$, 1H), 2.30 (m, $CH_2CH_2CH_2cHx$, 1H), 2.08 (m, Lac-β, 2H), 0.96 (t, Nva-$CH_3$, 3H), 0.95 (d, Leu-$CH_3$, 3H), 0.92 (t, propyl $CH_3$, 3H), 0.91 (d, Leu-$CH_3$, 3H). Mass spectrum [FAB]: 479.3 (M+1).

EXAMPLE 31 cHpCH=CHCH$_2$-α-Propyl-(R)-γ-Lactam-Nva-Leu-$NH_2$ (77)

4.3 mg (28 μmole, 1.2 eq.) of 3-cycloheptyl-1-propenal, 8.3 mg (23 μmole) of (75), the product of Example 30, Step 8, 47 μL (47 μmole, 2.0 eq) of 1N sodium cyanoborohydride and 0.7 μL (12 μmole, 0.5 eq.) of AcOH were combined in 0.25 mL methanol to give the title compound after $NaHCO_3$ workup and silica gel chromatography. NMR (400 MHz, $CD_3OD$): δ 5.62 (dd, cHpCH=CHCH$_2$, 1H), 5.44 (m, cHpCH=CHCH$_2$, 1H), 4.62 (dd, Nva-α, 1H), 4.37 (dd, Leu-α, 1H), 3.44 (m, Lac-γ, 2H), 2.51 (m, cHpCH=CHCH$_2$, 1H), 2.30 (m, cHpCH=CHCH$_2$, 1H), 2.08 (m, Lac-β, 2H), 0.96 (t, Nva-$CH_3$, 3H), 0.94 (d, Leu-$CH_3$, 3H), 0.92 (t, propyl $CH_3$, 3H), 0.90 (d, Leu-$CH_3$, 3H).

EXAMPLE 32 cHp$(CH_2)_3$-α-Propyl-(R)-γ-Lactam-Nva-Leu-$NH_2$ (78)

All of (77), the product of Example 31, was dissolved in 0.5 mL of methanol. 2 mg of 10% palladium on carbon was then added, followed by evacuation of the reaction vessel and a $H_2$ charge. After 1 h the catalyst was filtered off over Celite™ diatomaceous earth, and the filtrate evaporated. Flash silica gel chromatography was used to isolate the title compound. NMR (500 MHz, $CD_3OD$): δ 4.62 (dd, Nva-α, 1H), 4.37 (dd, Leu-α, 1H), 3.44 (m, Lac-γ, 2H), 2.51 (m, $CH_2CH_2CH_2$cHp, 1H), 2.30 (m, $CH_2CH_2CH_2$cHp, 1H), 2.08 (m, Lac-β, 2H), 0.96 (t, Nva-CH₃, 3H), 0.94 (d, Leu-CH₃, 3H), 0.92 (t, propyl CH₃, 3H), 0.90 (d, Leu-CH₃, 3H). Mass spectrum [FAB]: 493.2 (M+1).

EXAMPLE 33 cHx(CH₂)₃-α-(3-Hydroxypropyl)-(R)-γ-Lactam-Nva-Leu-NH₂ (81)

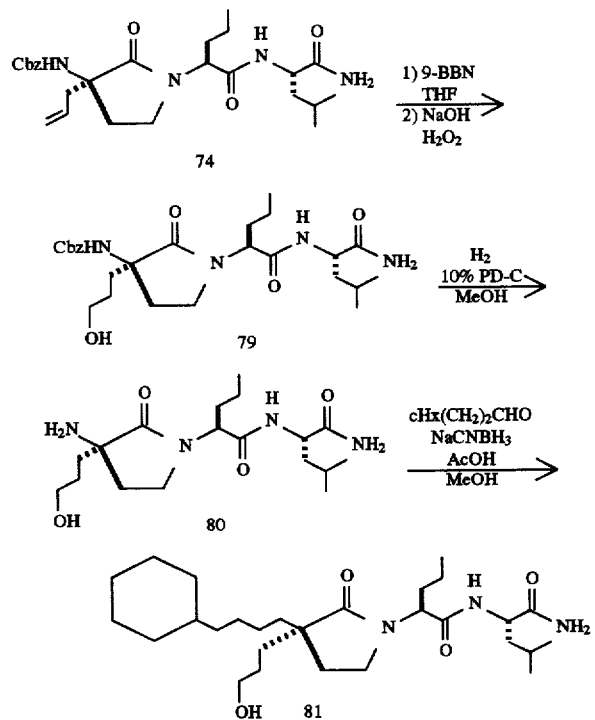

Step 1
Preparation of Cbz-α-(3-Hydroxypropyl)-D-γ-Lactam-Nva-Leu-NH₂ (79)

29 mg (60 μmole) of (74), the product of Example 30, Step 7, was dissolved in 100 μL of THF, and 300 μL of 0.5N 9-BBN. Allowed to stir overnight. Workup of a small aliquot (10 μL; NaOH/H₂O₂) showed that very little conversion had occurred. Another 300 μL of 9-BBN was added and the reaction monitored by TLC. 800 μL of additional 9-BBN was added over the next 8 h as additional progress was seen. Let stir overnight. TLC showed reaction was now complete, so 5 mL of 0.2N NaOH was added, followed by 3 mL of 30% H₂O₂. After 15 min of stirring, the reaction mixture was extracted 3× with CH₂Cl₂, then the organic was dried over Na₂SO₄, filtered, and the filtrate evaporated. The title compound was isolated after multiple silica gel chromatographies. NMR (400 MHz, CD₃OD): δ 7.32 (m, Ph, 5H), 5.05 (s, PhCH₂O, 2H), 4.39 (dd, Nva-α, 1H), 4.33 (dd, Leu-α, 1H), 3.51–3.41 (m, Lac-γ & CH₂CH₂CH₂OH, 4H), 2.44 (m, Lac-β, 1H), 2.04 (m, Lac-β, 1H), 0.96 (t, Nva-CH₃, 3H), 0.95 (d, Leu-CH₃, 3H), 0.89 (d, Leu-CH₃, 3H).

Step 2
Preparation of H₂N-α-(3-Hydroxypropyl)-(R)-γ-Lactam-Nva-Leu-NH₂ (80)

11.4 mg (23 μmole) of (79), the product of Step 1, was dissolved in 1 mL of methanol. 5 mg of 10% palladium on carbon was added, and the vessel was evacuated and charged with H₂. 90 min later the reaction mixture was filtered over Celite™ diatomaceous earth, the filtrate evaporated, and the title compound isolated by flash silica gel chromatography. NMR (400 MHz, CD₃OD): d 4.56 (dd, Nva-α, 1H), 4.37 (dd, Leu-α, 1H), 3.53 (m, Lac-γ, 2H), 3.44 (m, CH₂CH₂CH₂OH, 2H), 2.07 (m, Lac-β, 1H), 0.96 (t, Nva-CH₃, 3H), 0.95 (d, Leu-CH₃, 3H), 0.89 (d, Leu-CH₃, 3H).

Step 3
Preparation of cHx(CH₂)₃-α-(3-Hydroxypropyl)-(R)-γ-Lactam-Nva-Leu-NH₂ (81)

2.8 μL (18 μmole) of 3-cyclohexyl-1-propanal, 6.7 mg (18 μmole) of (80), and 19 μL (19 μmole) of 1N sodium cyanoborohydride were combined in 0.20 mL methanol to give the title compound after NaHCO₃ workup and silica gel chromatography. NMR (500 MHz, CD₃OD): d 4.61 (dd, Nva-α, 1H), 4.36 (dd, Leu-α, 1H), 3.52 (m, Lac-γ, 2H), 3.44 (m, CH₂CH₂CH₂OH, 2H), 2.53 (m, CH₂CH₂CH₂cHx, 1H), 2.32 (m, CH₂CH₂CH₂cHx, 1H), 2.07 (m, Lac-β, 2H), 0.96 (t, Nva-CH₃, 3H), 0.95 (d, Leu-CH₃, 3H), 0.90 (d, Leu-CH₃, 3H). Mass spectrum [FAB]: 495.3 (M+1).

EXAMPLE 34 cHx(CH₂)₃-α-Propyl-(S)-γ-Lactam-Nva-Leu-NH₂ (84)

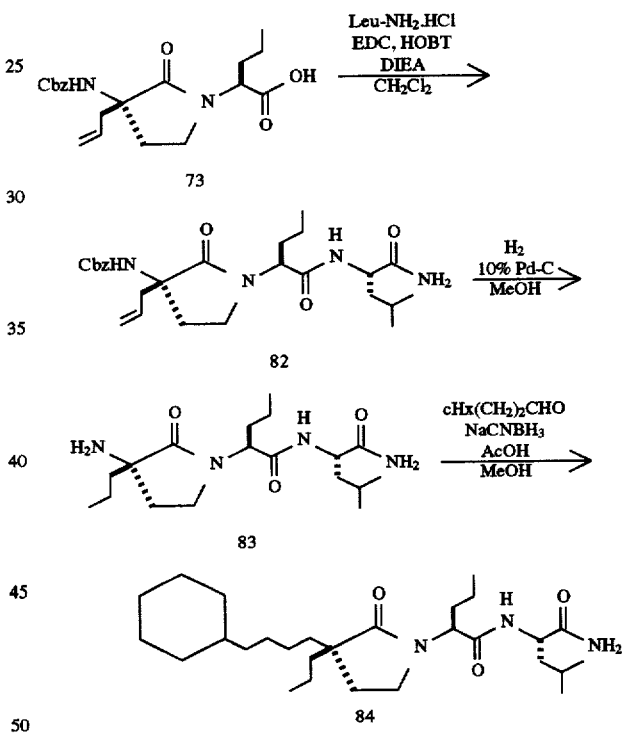

Step 1
Preparation of Cbz-α-Allyl-(S)-γ-Lactam-Nva-Leu-NH₂ (82)

10 mg (27 μmole) of (73), a product of Example 30, Step 6, was dissolved in 175 μL of DMF. 4.3 mg HOBT and 6.2 mg EDC (32 μmole, 1.2 eq. each) were added and the activated ester complex was stirred for 10 min. Then 4.5 mg (27 μmole) of leucine carboxamide HCl and 4.7 mL (27 μmole) of DIEA were then added and the reaction was stirred overnight. The reaction was then dumped into water and extracted 2× with ethyl acetate. The combined extracts were washed 2× each with 5% citric acid and 5% NaHCO₃. The organic was dried over Na₂SO₄, filtered, and the filtrate evaporated. The crude isolate was purified by silica gel chromatography to give of the title compound. NMR (400 MHz, CD₃OD): δ 7.31 (m, Ph, 5H), 5.78 (m, CH₂CH=CH₂, 1H), 5.21 (m, CH₂CH=CH₂, 2H), 5.07 (dd, PhCH₂O, 2H), 4.63 (dd, Nva-α, 1H), 4.32 (dd, Leu-α, 1H), 3.30 (m, Lac-γ, 1H), 2.47 (m, Lac-β, 2H), 2.38 (t, CH₂CH=CH₂, 2H), 0.94 (t, Nva-CH₃, 3H), 0.89 (d, Leu-CH₃, 3H), 0.87 (d, Leu-CH₃, 3H).

Step 2

Preparation of H₂N-α-Propyl-(S)-γ-Lactam-Nva-Leu-NH₂ (83)

5.8 mg (12 μmole) of (82), the product of Step 1, was dissolved in 0.5 mL of methanol and 1 mg of 10% palladium on carbon was added. The reaction vessel was evacuated and charged with H₂. After 2 h, the reaction was complete and the catalyst was filtered off through Celite™ diatomaceous earth and the filtrate evaporated and pumped on high vacuum to give the title compound. NMR (400 MHz, CD₃OD): δ 4.55 (dd, Nva-α, 1H), 4.36 (dd, Leu-α, 1H), 3.53 (dt, Lac-γ, 1H), 3.30 (m, Lac-γ, 1H), 2.14 (m, Lac-β, 1H), 1.90 (m, Lac-β, 1H), 0.96 (t, Nva-CH₃, 3H), 0.91 (d, Leu-CH₃, 3H), 0.89 (d, Leu-CH₃, 3H).

Step 3

Preparation of cHx(CH₂)₃-α-Propyl-(S)-γ-Lactam Nva Leu-NH₂ (84).

1.8 μL (12 μmole) of 3-cyclohexyl-1-propanal, 4.4 mg (12 μmole) of (83), the product of Step 2, 24 μL (24 μmole, 2.0 eq) of 1N sodium cyanoborohydride and 0.7 μL (12 μmole) of AcOH were combined in 0.5 mL methanol to give the title compound after NaHCO₃ workup and silica gel chromatography. NMR (500 MHz, CD₃OD): 67 4.59 (dd, Nva-α, 1H), 4.38 (dd, Leu-α, 1H), 3.57 (dt, Lac-γ, 1H), 3.34 (ddd, Lac-γ, 1H), 2.50 (m, CH₂CH₂CH₂cHx, 1H), 2.31 (m, CH₂CH₂CH₂cHx, 1H), 2.07 (m, Lac-β, 2H), 0.96 (t, Nva-CH₃, 3H), 0.94 (d, Leu-CH₃, 3H), 0.91 (t, propyl CH₃, 3H), 0.91 (d, Leu-CH₃, 3H).

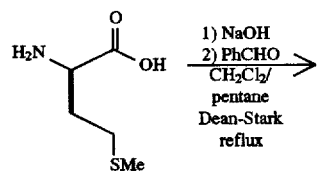

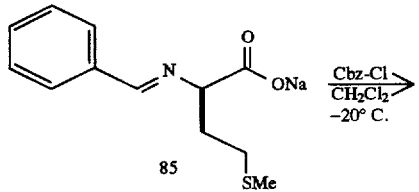

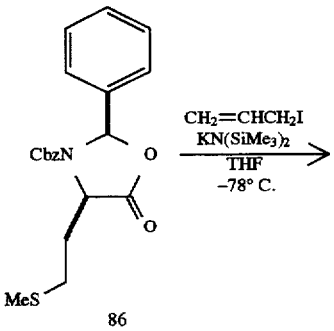

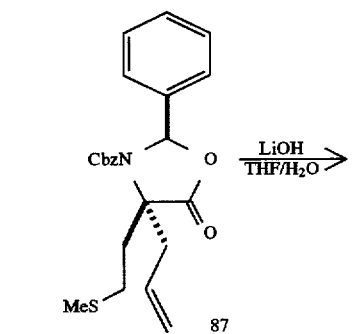

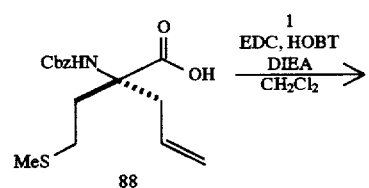

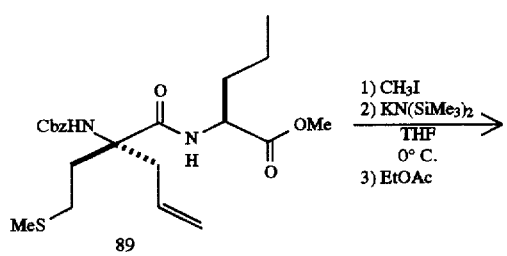

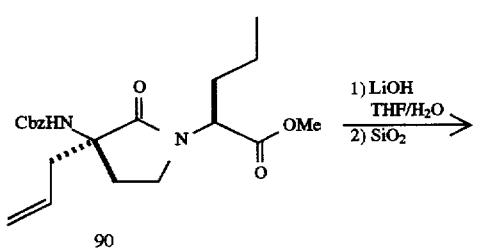

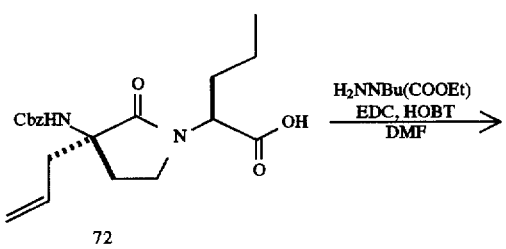

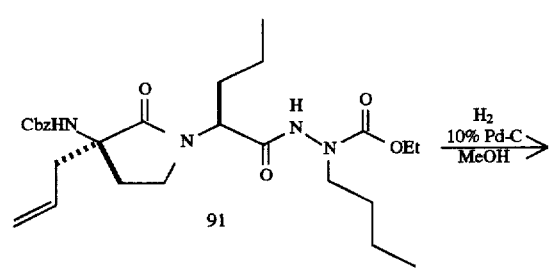

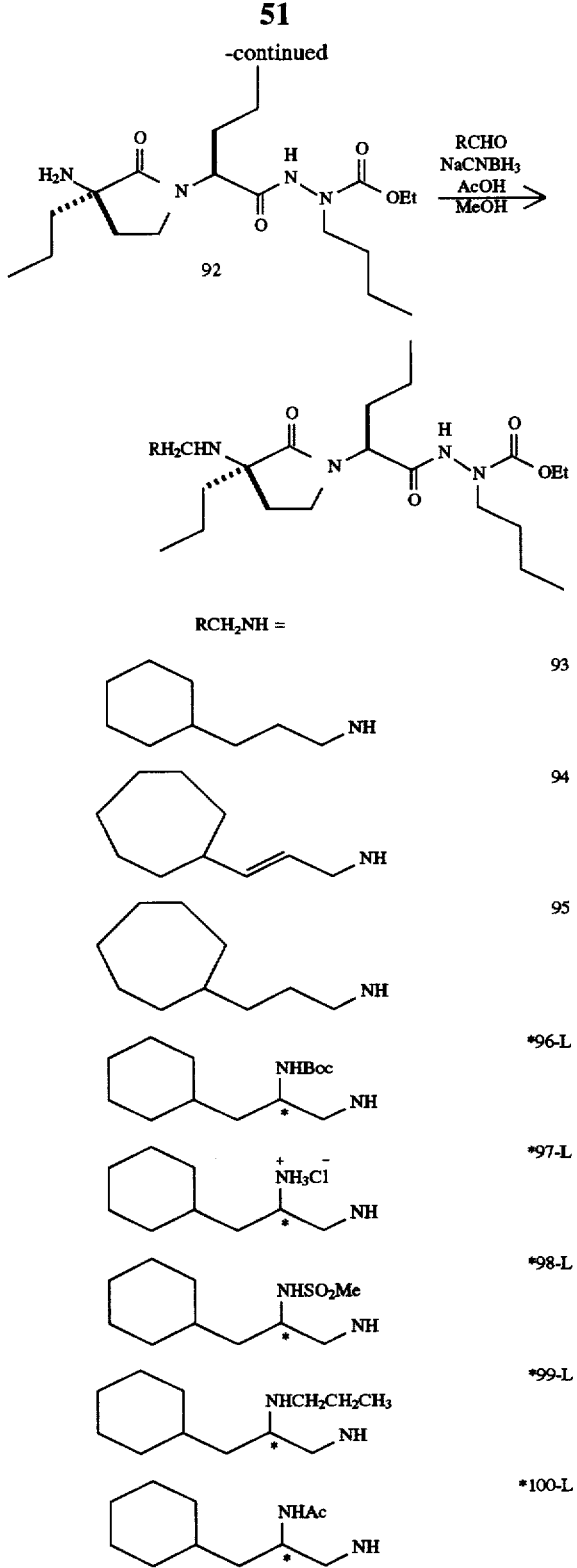

EXAMPLE 35 cHx(CH₂)₃-α-propyl-(R)-γ-Lactam-Nva-NHNBu (COOEt) (93)

Step 1

Preparation of D-Methionine Benzyl Imine Sodium Salt (85)

7.46 g (50 mmole) of D-methionine was dissolved in 50 mL of 1N NaOH (50 mmole) and 50 mL ethanol. The solution was gently warmed for 15 min, then the liquid was evaporated. 25 mL CH₂Cl₂, 25 mL pentane, and 5.1 mL (50 mmole) of benzaldehyde were added, and the reaction vessel was fitted with a Dean-Stark trap and a reflux condenser. The reaction mixture was heated to reflux for 3 h. The solvent was evaporated and pumped on high vacuum to give the title compound as a slightly yellowish solid. NMR (300 MHz, CDCl₃): δ 7.92, 7.58, 7.25 (s, d, d, Ph, 5H), 3.73 (dd, Met-α, 1H), 1.83 (s, Met-CH₃, 3H).

Step 2

Preparation of 2-(R)-Phenyl-3-N-(Cbz)-4-(S)-(3-Thiobutyl)-Oxazolidinone (86)

3.0 g (11.7 mmole) of (85), the product of Step 1, was dissolved in 50 mL of CH₂Cl₂. The solution was cooled to −20° C., after which 2.5 mL (17.6 mole, 1.5 eq) benzyl chloroformate in 10 mL CH₂Cl₂ was added. Stirred at −20° C. for 93 h, warmed to room temperature, and diluted with CH₂Cl₂. The reaction mixture was washed 2× each with water, aq. NaHCO₃, aq. sodium bisulfite, and water again. The organic was dried over Na₂SO₄, filtered, and the filtrate evaporated. The crude isolate was first purified to give a mixture of the cis and trans oxazolidinones. The cis title compound was purified by prep RP-18 HPLC. 915 mg of >99% pure cis compound was isolated after one pass, as was 700 mg of cis enriched compound. The stereochemistry (cis configuration) was determined by NOE spectroscopy. NMR (400 MHz, CDCl₃): δ 7.34 (m, Ph, 5H), 6.72 (s, CbzNCH(Ph)O, 1H), 5.19 (s, PhCH₂O, 2H), 4.59 (t, CHCH₂CH₂SCH₃, 1H), 2.02 (s, Met-CH₃, 3H). Mass spectrum [FAB]: 372.2 (M+1).

Step 3

Preparation of 2-(R)-Phenyl-3-N-(Cbz)-4-(R)-(3-Thiobutyl)-4-Allyl-Oxazolidinone (87)

371 mg (1 mmole) of (86), the product of Step 2, was added to a flame-dried flask and 5 mL of freshly distilled THF was added. The solution was cooled to −78° C. Then added 108 μL (1.2 mmole, 1.2 eq.) of allyl iodide, followed by 3.0 mL of 0.5N (1.5 mmole, 1.5 eq.) potassium bis(trimethylsilyl)amide. TLC at 60 min showed the reaction was complete, so it was quenched with aqueous NH₄Cl and warmed to room temperature. Then the solution was diluted with water and extracted 2× with ethyl acetate. The combined ethyl acetate extracts were washed with dilute aqueous NH₄Cl, dried over Na₂SO₄, filtered, and the filtrate evaporated. The crude isolate was purified by silica gel chromatography to give the title compound. NMR (400 MHz, CD₃OD): δ 7.34 (m, Ph, 5H), 6.30 (s, CbzNCH(Ph)O, 1H), 5.66 (m, CH₂CH=CH₂, 1H), 5.20–4.95 (m, PhCH₂O & CH₂CH=CH₂, 4H), 2.02 (s, Met-CH₃, 3H). Mass spectrum [FAB]: 412.1 (M+1).

Step 4

Preparation of CbzNH-α-Allyl-D-Methionine (88)

220 mg (0.54 mmole) of (87), the product of Step 3, was dissolved in 4 mL of THF. 1 mL of 1N NaOH was added, and the reaction started at room temperature. TLC after 30 min showed little change, so the temperature was raised to 50° C. Once the reaction was complete, the THF was evaporated, diluted with CH₂Cl₂ and water, and acidified with HCl. Extracted 2× with CH₂Cl₂, dried the organic with Na₂SO₄, filtered, and the filtrate was evaporated. The residue was pumped on high vacuum to give the title compound. NMR (400 MHz, CD₃OD): δ 7.34 (m, Ph, 5H), 5.60 (m, CH₂CH=CH₂, 1H), 5.05 (s, PhCH₂O & CH₂CH=CH₂, 4H), 2.02 (s, Met-CH₃, 3H).

Step 5

Preparation of Cbz-α-Allyl-D-Met-Nva methyl ester (89)

165 mg (0.51 mmole) of (88), the product of Step 4, 2.5 mL of CH₂Cl₂, 83 mg HOBT and 118 mg EDC (0.61 mmole, 1.2 eq. each) were mixed and the activated ester complex stirred for 5 min. 85 mg (0.51 mmole) Nva methyl ester.HCl and 89 mL (0.51 mmole) DIEA were then added and the reaction stirred 3.5 h. The reaction was diluted with $CH_2Cl_2$ and washed 2× each with 5% citric acid and 5% $NaHCO_3$, dried over $Na_2SO_4$, filtered, and the filtrate evaporated. The title compound was isolated by silica gel chromatography. NMR (400 MHz, $CD_3OD$): δ 7.32 (m, Ph, 5H), 5.66 (m, $CH_2CH=CH_2$, 1H), 5.05 (m, $PhCH_2O$ & $CH_2CH=CH_2$, 4H), 4.37 (dd, Nva-α, 1H), 3.68 (s, $COOCH_3$, 3H), 2.01 (s, Met-$CH_3$, 3H), 0.91 (t, Nva-$CH_3$, 3H).

Step 6
Preparation of Cbz-α-Allyl-(R)-γ-Lactam-Nva-Methyl Ester (90)

44.2 mg (101 μmole) of (89), the product of Step 5, was dissolved in 1 mL iodomethane, and the reaction stirred for 64 h. The iodomethane was evaporated and the residue dissolved in 2.2 mL freshly distilled THF and transferred to a flame dried flask. The solution was cooled to −5° C., then 200 mL of 0.5 N potassium bis(trimethylsilyl) amide (100 μmole) was added and the reaction stirred for 90 min. 1 mL of ethyl acetate was added and the reaction was stirred for 15 min, then mL of aq. $NH_4Cl$ was added and the aqueous was extracted 2× with ethyl acetate. The organic was washed a second time with aq. $NH_4Cl$, then dried over $Na_2SO_4$, filtered, and the filtrate evaporated. The crude isolate was purified by silica gel to give the title compound as a Single isomer. NMR (400 MHz, $CD_3OD$): δ 7.31 (m, Ph, 5H), 5.84 (m, $CH_2CH=CH_2$, 1H), 5.16 (d & dd, $CH_2CH=CH_2$, 2H), 5.03 (s, $PhCH_2O$, 2H), 4.72 (dd, Nva-α, 1H), 3.71 (s, $COOCH_3$, 3H), 3.37 (m, Lac-γ, 2H), 2.44 (m, $CH_2CH=CH_2$ & Lac-β, 3H), 2.22 (m, Lac-β, 1H), 0.95 (t, Nva-$CH_3$, 3H).

Step 7
Preparation of Cbz-α-Allyl-(R)-γ-Lactam-Nva (72)

22 mg (57 μmole) of (90), the product of Step 6, was dissolved in 0.57 mL of THF. 0.14 mL of 1.0 N LiOH was added and the reaction was stirred for 30 min. It was then diluted with water and $CH_2Cl_2$, then acidified with HCl. The aqueous layer was extracted 3× with $CH_2Cl_2$, dried over $Na_2SO_4$, filtered, and the filtrate evaporated. The title compound was isolated by silica gel chromatography. NMR (400 MHz, $CD_3OD$): δ 7.31 (m, Ph, 5H), 5.84 (m, $CH_2CH=CH_2$, 1H), 5.16 (d &dd, $CH_2CH=CH_2$, 2H), 5.03 (s, $PhCH_2O$, 2H), 4.68 (dd, Nva-α, 1H), 3.39 (m, Lac-γ, 2H), 2.42 (m, $CH_2CH=CH_2$ & Lac-β, 3H), 2.20 (m, Lac-β, 1H), 0.95 (t, Nva-$CH_3$, 3H).

Step 8
Preparation of Cbz-α-Allyl-(R)-γ-Lactam-Nva-NHNBu (COOEt) (91)

20 mg (58.5 μmole) of (72), the product of Step 7, was dissolved in 1 mL of DMF and the reaction mixture was cooled to 0° C. 15.8 mg HOBT and 22.5 mg EDC (117 μmole, 2.0 eq. each) were added and the activated ester complex stirred for 10 min. Then 14 mg (88 μmole, 1.5 eq.) of $H_2NNBu(COOEt)$ was added and the reaction mixture stirred at room temperature overnight. Water was poured into the reaction mixture, which was then extracted with ethyl acetate. The organic was then washed 2× each with 5% citric acid and 5% $NaHCO_3$. The organic was dried over $Na_2SO_4$, filtered, and the filtrate evaporated. The title compound was recovered after silica gel chromatography. NMR (400 MHz, $CD_3OD$, 55° C.): δ 7.30 (m, Ph, 5H), 5.78 (m, $CH_2CH=CH_2$, 1H), 5.17 (m, $CH_2CH=CH_2$, 1H), 5.06 (s, $PhCH_2O$, 2H), 4.49 (dd, Nva-α, 1H), 4.12 (q, $OCH_2CH_3$, 2H), 3.53–3.34 (m, Lac-γ & $NCH_2CH_2CH_2CH_3$, 4H), 2.41 (m, Lac-β & $CH_2CH=CH_2$, 3H), 2.23 (m, Lac-β, 1H), 1.23 (t, $OCH_2CH_3$, 3H), 0.96 (t, Nva-$CH_3$, 3H), 0.92 (t, $NCH_2CH_2CH_2CH_3$, 3H).

Step 9
Preparation of $H_2$N-α-propyl-(R)-γ-Lactam-Nva-NHNBu (COOEt) (92)

20 mg (39 μmole) of (91), the product of Step 7, was dissolved in 1 mL methanol. 15 mg of 10% palladium on carbon was added, the vessel evacuated, then charged with $H_2$. At 1 h the catalyst was filtered off over Celite™ diatomaceous earth and the filtrate evaporated to give the title compound. NMR (400 MHz, $CD_3OD$): δ 4.56 (dd, Nva-α, 1H), 4.12 (q, $OCH_2CH_3$, 2H), 3.53–3.34 (m, Lac-γ & $NCH_2CH_2CH_2CH_3$, 4H), 2.16 (m, Lac-β, 1H), 1.87 (m, Lac-β, 1H), 1.23 (t, $OCH_2CH_3$, 3H), 0.96 (t, Nva-$CH_3$, 3H), 0.92 (t, $NCH_2CH_2CH_2CH_3$, 3H), 0.90 (t, propyl $CH_3$, 3H).

Step 10
Preparation of $cHx(CH_2)_3$-α-propyl-(R)-γ-Lactam-Nva-NHNBu(COOEt) (93)

3.7 μL (24 μmole, 1.26 eq.) of 3-cyclohexyl-1-propanol, 7.3 mg (19 μmole) of (92), the product of Step 8, 38 μL (38 μmole, 2.0 eq) of 1N sodium cyanoborohydride and 0.7 μL (12 μmole, 0.63 eq.) of AcOH were combined in 0.2 mL methanol to give the title compound after $NaHCO_3$ workup and silica gel chromatography. NMR (500 MHz, $CD_3OD$): δ 4.61 (dd, Nva-α, 1H), 4.12 br q, $OCH_2CH_3$, 2H), 3.53–3.34 (m, Lac-γ & $NCH_2CH_2CH_2CH_3$, 4H), 2.52 (m, $CH_2CH_2CH_2$cHx, 1H), 2.31 (m, $CH_2CH_2CH_2$cHx, 1H), 2.07 (m, Lac-β, 2H), 0.98 (t, Nva-$CH_3$, 3H), 0.93 (t, $NCH_2CH_2CH_2CH_3$, 3H), 0.91 (t, propyl $CH_3$, 3H). Mass spectrum [FAB]: 509.3 (M+1).

EXAMPLE 36 cHpCH=CHCH$_2$-α-propyl-(R)-γ-Lactam-Nva-NHNBu( COOEt) (94)

3.4 mg (23 μmole, 1.2 eq.) of 3-cycloheptyl-1-propenal, 7.2 mg (19 μmole) of (92), the product of Example 35, Step 8, 38 μL (38 μmole, 2.0 eq) of 1N sodium cyanoborohydride and 0.7 μL (12 μmole, 0.63 eq.) of AcOH were combined in 0.2 mL methanol to give the title compound after $NaHCO_3$ workup and silica gel chromatography. NMR (400 MHz, $CD_3OD$): δ 5.62 (dd, cHpCH=CHCH$_2$, 1H), 5.45 (m, cHpCH=CHCH$_2$, 1H), 4.59 (dd, Nva-α, 1H), 4.12 (br q, $OCH_2CH_3$, 2H), 3.53–3.34 (m, Lac-γ & $NCH_2CH_2CH_2CH_3$, 4H), 2.52 (m, cHpCH=CHCH$_2$, 1H), 2.30 (m, cHpCH=CHCH$_2$, 1H), 2.07 (m, Lac-β, 2H), 0.98 (t, Nva-$CH_3$, 3H), 0.93 (t, $NCH_2CH_2CH_2CH_3$, 3H), 0.91 (t, propyl $CH_3$, 3H).

EXAMPLE 37

CHp$(CH_2)_3$-α-propyl-(R)-γ-Lactam-Nva-NHNBu (COOEt) (95)

All of the product of Example 36, (94) was dissolved in 0.5 mL of methanol. 2 mg of 10% palladium on carbon was then added, followed by evacuation of the reaction vessel and a $H_2$ charge. After 1 h the catalyst was filtered off over Celite™ diatomaceous earth, and the filtrate evaporated. Flash silica gel chromatography was used to isolate the title compound. NMR (500 MHz, $CD_3OD$): δ 4.61 (dd, Nva-α, 1H), 4.12 (br q, $OCH_2CH_3$, 2H), 3.53–3.34 (m, Lac-γ & $NCH_2CH_2CH_2CH_3$, 4H), 2.52 (m, cHpCH$_2CH_2CH_2$, 1H), 2.30 (m, cHpCH$_2CH_2CH_2$, 1H), 2.07 (m, Lac-β, 2H), 0.98 (t, Nva-$CH_3$, 3H), 0.93 (t, $NCH_2CH_2CH_2CH_3$, 3H), 0.91 (t, propyl $CH_3$, 3H). Mass spectrum [FAB]: 523.3 (M+1).

EXAMPLE 38

Boc-L-Chaψ(CH$_2$HN)-α-Propyl-(R)-γ-Lactam-Nva-NHNBu(COOEt) (96)

46.2 mg (181 μmole) of Boc-Cha-CHO, 69.6 mg (181 μmole) of (92), the product of Example 35, Step 8, 362 μL (362 μmole, 2.0 eq) of 1N sodium cyanoborohydride and 9 μL (150 μmole, 0.8 eq.) of AcOH were combined in 1 mL methanol to give the title compound after NaHCO₃ workup and silica gel chromatography. NMR (500 MHz, CD₃OD): δ 4.59 (dd, Nva-α, 1H), 4.11 (br q, OCH₂CH₃, 2H), 3.63 (m, Cha-α, 1H), 3.52–3.34 (m, Lac-γ & NCH₂CH₂CH₂CH3, 4H), 2.49 (m, BocChaCH₂NH, 1H), 2.40 (m, BocChaCH₂NH, 1H), 2.04 (m, Lac-β, 2H), 1.43 (s, t-Bu, 9H), 0.97 (t, Nva-CH₃, 3H), 0.92 (t, NCH₂CH₂CH₂CH₃, 3H), 0.90 (t, propyl CH₃, 3H). Mass spectrum [FAB]: 624.6 (M+1).

EXAMPLE 39

HCl.H₂N-Chaψ(CH₂HN)-α-Propyl-(R)-γ-Lactam-Nva-NHNBu(COOEt) (97)

40 mg (64 μmole) of (96), the product of Example 38, was dissolved in 1 mL of 4N HCl in dioxane. After 45 min the dioxane was filtered, then CH₂Cl₂ and hexanes were added and evaporated to give a hygroscopic white solid as the title compound. NMR (500 MHz, CD₃OD): δ 4.58 (dd, Nva-α, 1H), 4.13 (br q, OCH₂CH₃, 2H), 3.67 (br m, Cha-α, 1H), 3.62–3.34 (br t, br m, br m, Lac-γ & NCH₂CH₂CH₂CH₃, 4H), 2.42 (br t, ChaCH₂NH, 2H), 1.89 (m, Lac-β, 2H), 1.00 (t, Nva-CH₃, 3H), 0.98 (t, NCH₂CH₂CH₂CH₃, 3H), 0.93 (t, propyl CH₃, 3H). Mass spectrum [FAB]: 524.3 (M+1).

EXAMPLE 40

MeSO₂-Chaψ(CH₂HN)-α-Propyl-(R)-γ-Lactam-Nva-NHNBu(COOEt) (98)

5.6 mg (10 μmole) of (97), the product of Example 39, was dissolved in 50 μL CH₂Cl₂, after which was added 1.2 mg DMAP (10 μmole) and 0.8 μL (10 μmole) methanesulfonyl chloride. Allowed to stir overnight. TLC showed that the reaction was not complete, so another 4.5 mg (38 μmole) DMAP was added. After 5 h the reaction was complete, so it was diluted with CH₂Cl₂ and washed 2× with 0.5 N HCl. The organic was dried over Na₂SO₄, filtered and the filtrate evaporated and pumped on high vacuum to give the title compound. NMR (500 MHz, CD₃OD): δ 4.60 (dd, Nva-α, 1H), 4.12 (br q, OCH₂CH₃, 2H), 3.57 (br m, Cha-α, 1H), 3.55–3.34 (br m, Lac-γ & NCH₂CH₂CH₂CH₃, 4H), 3.00 (s, CH₃SO₂, 3H), 2.88 (br m, CH₃SO₂NHChaCH₂NH, 1H), 2.88 (br m, CH₃SO₂NHChaCH₂NH, 1H), 2.23 (m, Lac-β, 2H), 1.00 (t, Nva-CH₃, 3H), 0.95 (t, NCH₂CH₂CH₂CH₃, 3H), 0.94 (t, propyl CH₃, 3H). Mass spectrum [FAB]: 602.4 (M+1).

EXAMPLE 41

Pr-Chaψ(CH₂HN)-α-Propyl-(R)-γ-Lactam-Nva-NHNBu(COOEt) (99)

Using a typical reductive amination procedure, 5.6 mg (10 μmole) of (97), the product of Example 39, 50 μL methanol, 0.7 μL (10 μmole) of 1-propanal, and 2 mg sodium cyanoborohydride (32 μmole, 3.2 eq.) were allowed to stir 36 h. Subsequent NaHCO₃ workup and silica gel chromatography gave the title compound. NMR (500 MHz, CD₃OD): δ4.61 (dd, Nva-α, 1H), 4.12 (br q, OCH₂CH₃, 2H), 3.53–3.35 (br m, Lac-γ & NCH₂CH₂CH₂CH₃, 4H), 2.84 (br m, Cha-α, 1H), 2.76 (br m, PrNHChaCH₂NH, 1H), 2.64 (br m, CH₃CH₂CH₂NHChaCH₂NH, 2H), 2.47 (m, PrNHChaCH₂NH, 1H), 2.06 (t, CH₃CH₂CH₂NHChaCH₂NH, 2H), 0.99 (t, Nva-CH₃, 3H), 0.99 (t, CH₃CH₂CH₂NHChaCH₂NH, 3H), 0.93 (t, NCH₂CH₂CH₂CH₃, 3H), 0.93 (t, propyl CH₃, 3H). Mass spectrum [FAB]: 566.4 (M+1).

EXAMPLE 42

Ac-Chaψ(CH₂HN)-α-Propyl-(R)-γ-Lactam-Nva-NHNBu(COOEt) (100)

5.6 mg (10 μmole) of 97, the product of Example 39, was dissolved in 50 μL CH₂Cl₂, then 7 μL (50 μmole, 5.0 eq.) Et₃N and 1.5 μL (15 μmole, 1.5 eq.) acetic anhydfide were added and the reaction stirred for 75 min. The solution was directly purified by mini-flash silica gel chromatography to give the title compound. NMR (500 MHz, CD₃OD): δ 4.59 (dd, Nva-α, 1H), 4.11 (br q, OCH₂CH₃, 2H), 3.97 (m, Cha-α, 1H), 3.53–3.34 (br m, Lac-γ & NCH₂CH₂CH₂CH₃, 4H), 2.53 (m, CH₃CONHChaCH₂NH, 1H), 2.41 (m, CH₃CONHChaCH₂NH, 1H), 2.03 (m, Lac-β, 2H), 1.94 (s, CH₃CONHCha, 3H), 0.98 (t, Nva-CH₃, 3H), 0.93 (t, NCH₂CH₂CH₂CH₃, 3H), 0.90 (t, propyl CH₃, 3H). Mass spectrum [FAB]: 566.4 (M+1).

EXAMPLE 43

Ph(CH₂)₂SO₂-(R)-γ-Lactam-Nva-Leu-NH₂ (102)

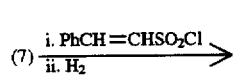

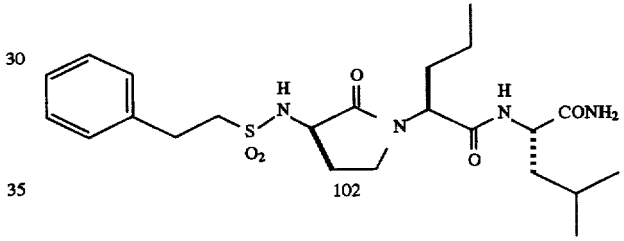

Step 1
Preparation of PhCH=CHSO₂-(R)-γ-lactam-Nva-Leu-NH₂ (101)

(7) (30 mg, 96 μmol, the product of Example 1, Step 7) was dissolved in CH₂Cl₂ (1 mL) at ambient temperature and Et₃N (20 μL, 1.5 eq) added, followed by trans-β-styrenesulfonyl chloride (19 mg, 1eq). After 1 h the mixture was diluted with aq. NaHCO₃ solution and extracted with CH₂Cl₂. The organics were washed with 0.5N HCl, then brine, dried over MgSO₄, filtered and concentrated. The residue was chromatographed on silica gel to give the title compound as a white powder. NMR (400 MHz, CD₃OD): δ 7.60 (2H, m, Ar), 7.45 (1H, d, CH=CH), 7.40 (3H, m, Ar), 7.15 (1H, d, CH=CH), 4.60 (1H, dd, H-α), 4.35 (1H,dd, H-α), 4.10 (1H, dd, H-α, 3.40 (2H, m, Lac-γ), 2.50 (1H, m, Lac-β), 0.95 (3H, t, Nva-CH₃), 0.90 (3H, d, Leu-CH₃), 0.85 (3H, d, Leu-CH₃). Mass spectrum [ESI]: 479 (MH⁺), 462, 348, 321.
Step 2
Preparation of Ph(CH₂)-₂SO₂-(R)-γ-lactam-Nva-Leu-NH₂ (102)

(101) (24 mg, the product of Step 1) was dissolved in ethanol (1.5 mL) and 5% palladium on carbon added. The mixture was hydrogenated at 1 atm and ambient temperature overnight. The mixture was filtered through Celite™ diatomaceous earth and concentrated, to give the title compound. NMR (500 MHz, CDCl₃): α 7.34–7.20 (5H, m, Ar), 6.21 (1H, br s, CONH₂), 5.99 (1H, br s, CONH₂), 5.69 (1H, d, SO₂NH), 4.50 (1H, dd, H-α), 4.41 (1H, dd, H-α), 4.18 (1H, m, H-α), 3.41 (4H, m, Lac-γ & CH₂SO₂N), 3.22 (1H, ddd, ArCH), 3.15 (1H, ddd, ArCH), 2.59 (1H, m, Lac-β), 0.95 (3H, t, Nva-CH₃), 0.90 (3H, d, Leu-CH₃), 0.88 (3H, d, Leu-CH₃). Mass spectrum [ESI]: 481 (MH⁺), 464, 351, 323.

EXAMPLE 44

Cbz-(R)-γ-Lactam-Nva-Leu-NH₂ (103)

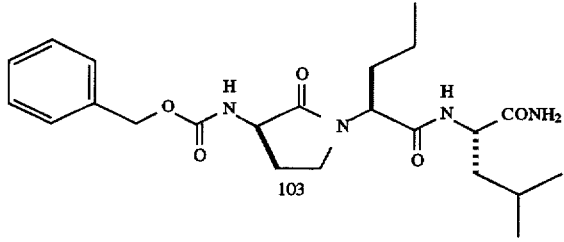

(7) (10mg, 29 μmol, the product of Example 1, Step 7) was dissolved in CH₂Cl₂ (1 mL) at ambient temperature and DMAP (5mg, 1.5 eq) added, followed by benzyl chloroformate (5 μL, 1.2 eq). After 2.5 h the mixture was diluted with aq. NaHCO₃ solution and extracted with CH₂Cl₂. The organics were washed with 0.5N HCl, dried over Na₂SO₄, filtered and concentrated. The residue was chromatographed on silica gel to give the title compound as an oil. NMR (400 MHz, CD₃OD): δ 7.35 (5H, m, Ar), 5.10 (2H, s, ARCH₂), 4.60 (1H, dd, H-α), 4.35 (1H, dd, H-α), 4.25 (1H, dd, H-α), 3.45 (2H, m, Lac-γ), 2.45 (1H, m, Lac-β), 0.95 (9H, m, Nva-CH₃, Leu-CH₃, Leu-CH₃). Mass spectrum [ESI]: 448 (MH₂⁺), 430, 317, 289.

EXAMPLE 45

Boc-(R)-γ-Lactam-Nva-CH=CHCO₂Et (106)

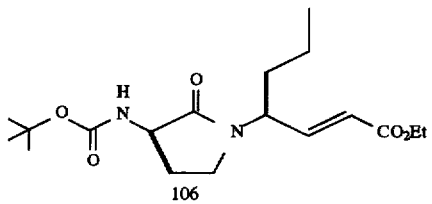

Step 1
Preparation of Boc-(R)-γ-lactam-Nva-Leu-N(OMe)Me (104)

(5) (1.0g, 3.3 mmol, the product of Example 1, Step 5) was dissolved in CH₂Cl₂ (1 mL) at ambient temperature and Et₃N (1.2 mL, 2.5 eq) added, followed by N,O-dimethylhydroxylamine (341 mg, 1.05 eq) and then BOP (1.55 g, 1.05 eq). After stirring overnight the mixture was diluted with aq. K₂CO₃ solution and extracted with CH₂Cl₂. The organics were washed with 0.5N HCl, dried over MgSO₄, filtered and concentrated. The residue was chromatographed on silica gel to give the title compound as a foam (1.0 g). NMR (400 MHz, CD₃OD): δ 5.15 (1H, br, Nva-α), 4.20 (1H, t, Lac-α), 3.80 (3H, s, OMe), 3.45 (2H, m, Lac-γ), 3.20 (3H, br s, NMe), 2.40 (1H, ddd, Lac-β), 1.90 (1H, m, Lac-β), 1.75 (2H, m, Nva-β), 1.45 (9H, s, tBuOCO), 0.95 (3H, t, Nva-CH₃).

Step 2
Preparation of Boc-(R)-γ-lactam-Nva-Leu-CH=CHCO₂Et (106)

(104) (5 mg, 140 μmol, the product Step 1) was dissolved in Et₂O (1.5 mL) at ambient temperature and lithium aluminum hydride (7 mg, 1.25 eq) added. After 30 min the mixture was quenched with aq. KHSO₄ solution (730 μL, 0.35N) and stirred for 30 min before being extracted with Et₂O. The organics were dried over Na₂SO₄, filtered and concentrated. The crude aldehyde so formed (105) was dissolved in THF at ambient temperature and (carbethoxymethylene)triphenylphosphorane (50 mg, 1 eq) added. After 90 min the mixture Was diluted with aq. NaHCO₃ solution and extracted with EtOAc. The organics were dried over Na₂SO₄, filtered and concentrated. The residue was chromatographed on silica gel to give the title compound as an oil (28 mg). NMR (400 MHz, CD₃OD): δ 6.80 (1H, dd, CH=CHCO₂Et), 5.90 (1H, dd, CH=CHCO₂Et), 4.65 (1H, m, Nva-α), 4.25 (1H, dd, Lac-α), 4.20 (2H, q, CO₂CH₂), 3.35 (1H, dd, Lac-γ), 3.25 (1H, dd, Lac-γ), 2.40 (1H, m, Lac-β), 1.90 (1H, m, Lac-β), 1.45 (9H, s, tBuOCO), 0.95 (3H, t, Nva-CH₃). Mass spectrum [CI, PB-NH₃]: 355 (MH⁺), 341,330.

EXAMPLE 46 cHx(CH₂)₃-(R)-γ-Lactam-Nvaψ(CH₂NH)Leu-NH₂ (108)

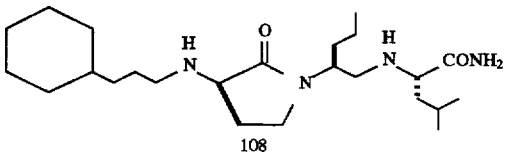

Step 1
Preparation of Boc-(R)-γ-Lactam-Nvaψ(CH₂NH)Leu-NH₂ (107):

The intermediate aldehyde (105) described in Example 45 Step 2 was reductively aminated with Leu-NH₂ using the typical procedure. Silica gel chromatography of the crude product gave the title compound. NMR (400 MHz, CD₃OD): δ 4.25 (1H, m, H-α), 4.05 (1H, m, H-α), 3.35–3.15 (2H, m, Lac-γ), 3.10 (1H, dd, H-α), 2.60 (2H, m, CH₂NH), 2.40 (1H, m, Lac-β), 0.95 (9H, m, Nva-CH₃, Leu-CH₃, Leu-CH₃).

Step 2
Preparation of cHx(CH₂)₃-(R)-γ-Lactam-Nvaψ(CH₂NH)Leu-NH₂ (108)

(107) (45 mg, the product of Step 1) was dissolved in 4N HCl in dioxane (1 mL). After 30 min the mixture was concentrated to give the crude amine salt as an oil. This was dissolved in methanol (1 mL) and 3-cyclohexylpropionaldehyde (17 μL, 1 eq) added followed by sodium cyanoborohydride (9 mg, 1.2 eq). After 90 min the mixture was diluted with aq. NaHCO₃/K₂CO₃ solution and extracted with EtOAc. The organics were dried over MgSO₄, filtered and concentrated. The residue was chromatographed on silica gel to give the title compound as an oil (13 mg). NMR (400 MHz, CD₃OD): δ 4.10 (1H, m, Nva-α), 3.50 (1H, dd, Lac-α), 3.35–3.20 (2H, m, Lac-γ), 3.05 (1H, dd, Leu-α), 2.60 (2H, m, CH₂NH), 2.35 (1H, m, Lac-β), 0.95 (9H, m, Nva-CH₃, Leu-CH₃, Leu-CH₃).

EXAMPLE 47 cHx(CH$_2$)$_3$-(R)-γ-Thiolactam-Nva-Leu-NH$_2$ (110)

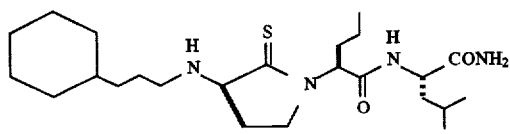

Step 1
Preparation of Boc-(R)-γ-Thiolactam-Nva-OMe (109)

(4) (260 mg, 0.8 mmol, the product of Example 1, Step 4) was dissolved in benzene (5 mL) and 2,4-bis(4-methoxyphenyl)-1,3-dithia-2,4-diphosphetane-2,4-disulfide [Lawesson's reagent] (168 mg, 0.5 eq) was added and the mixture was heated to reflux. After 6 h the mixture was cooled to ambient temperature, loaded directly onto a silica gel chromatography column and chromatographed to give the title compound as an oil (125 mg). NMR (400 MHz, CD$_3$OD): δ 5.60 (1H, dd, Lac-α), 4.45 (1H, br, Nva-α), 3.70 (3H, s, CO$_2$Me), 3.70–3.65 (2H, m, Lac-γ), 2.55 (1H, m, Lac-β), 1.45 (9H, s tBuOCO), 0.95 (3H, t, Nva-CH$_3$). Mass spectrum [ESI]: 331 (MH$^+$).

Step 2
Preparation of cHx(CH$_2$)$_3$-(R)-γ-Thiolactam-Nva-Leu-NH$_2$ (110)

Using procedures analogous to those employed in the conversion of (4) to (11), in Example 1 the thiolactam product of Step 1 (108) was converted to the title compound. NMR (500 MHz, CD$_3$OD): δ 5.38 (1H, dd, Lac-α, 4.36 (1H, dd, H-α), 3.87 (1H, dd, H-α), 3.67 (2H, m, Lac-γ), 2.64 (2H, m, CH$_2$NH), 2.45 (1H, m, Lac-β), 1.00–0.95 (3H, t, Nva-CH$_3$). Mass spectrum [Cl, PB-NH$_3$]: 453 (MH$^+$).

EXAMPLE 48

(CH$_3$)$_2$CCH(CH$_2$)$_2$CH(CH$_3$)CH$_2$-(R)-γ-Lactam-Nva-Leu-NH$_2$ (111)

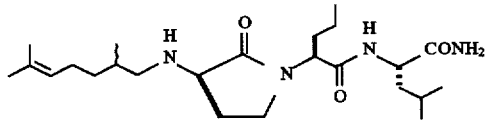

Using procedures analogous to those employed in Example 3, (7), the product of Example, Step 7, was converted to the title compound. Mass spectrum [ESI]: 437 (MH+).

EXAMPLE 49 cHxCH(CH$_2$)CHCH$_2$-(R)-γ-Lactam-Nva-Leu-NH$_2$ (112)

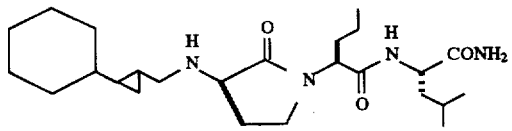

Using procedures analogous to those employed in Example 3, (7), the product of Example 1, Step 7, was converted to (112). NMR (400 MHz, CD$_3$OD): Characteristic absorptions, 4.64 (dd, 1H, J=10, 5.8 Hz), 4.36 (m, 1H), 4.15 (dt, 1H, J=10.4, 8 Hz), 3.56 (m, 2H), 3.35 (m, 1H), 3.07 (Isomer A: alpha protons of cyclohexylcyclopropylmethyl sidechain, AB of ABX, 2H, Δδ=33.79, JAB=12.9, JAX=7.9, JBX=7.3), 2.79 (Isomer B: alpha proton of cyclohexylcyclopropylmethyl sidechain, dd, 1H, J=12.8, 8.7 Hz. Second α-proton obscured at 3.3), 2.56 (m, 1H), 0.98 (t, 3H, J=7.3 Hz), 0.65 (m, 2H), 0.55 (m, 2H). Mass spectrum [ESI 80/29 CH$_3$CN/H$_2$O 0.01% TFA]m/z: 449.2, M+1 for calculated MW 448.3.

EXAMPLE 50

[4H]-Naphthyl-CH$_2$-(R)-γ-Lactam-Nva-Leu-NH$_2$ (113)

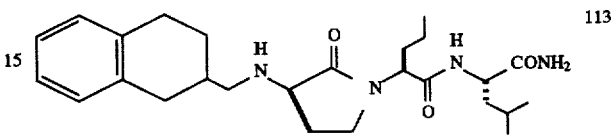

Using procedures analogous to those employed in Example 3, (7), the product of Example 1, Step 7, was converted to (113). NMR (400 MHz, CD$_3$OD): Characteristic absorptions, 7.08 (m, 4H), 4.66 (dd, 1H, J=6.3, 8.9 Hz), 4.22 (dd with fine coupling, 1H, J=11, 8.9, 1.9 Hz), 4.13 (brd m, 2H), 3.6 (brd d, 2H), 3.3–3.5 (2 brd m's, 2H), 3.38 (m, 1H), 3.07 (dd, 1H, J=12.2, 7.7 Hz), 2.95 (m, 1H), 2.87 (m, 2H), 2.6 (m, 2H), 1.00 (overlapping t's, 3H, two isomers offset by 1.24 Hz, J=7.3 Hz), 0.927 (overlapping t's, 3H, two isomers offset 0.88 Hz, J=7.4 Hz).

EXAMPLE 51 cHx(CH$_2$)$_3$-α-(3-Hydroxypropyl)-(R)-γ-Lactam-Nva-NHNBu(COOEt) (114)

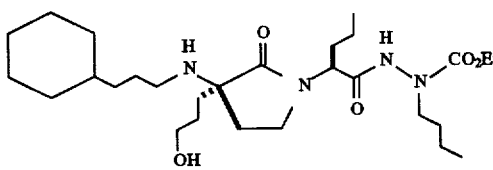

Using procedures analogous to those employed in Example 33 (74→81), (91), the product of Example 35, Step 8, was converted to (114). NMR (500 MHz, CD$_3$OD): δ 4.61 (1H, dd, Nva-α), 4.12 (2H, br, CO$_2$CH$_2$), 3.57–3.35 (6H, m CH$_2$OH, CH$_2$NCO$_2$Et, Lac-γ), 2.53 (1H, m, CH$_2$NH), 2.34 (1H, m, CH$_2$NH), 0.99 (3H, t, CH$_3$), 0.93 (3H, t, CH$_3$). Mass spectrum [ESI]: 525 (MH$^+$).

EXAMPLE 52 cHx(CH$_{23}$-α-(3-Azidopropyl)-(R)-γ-Lactam-Nva-NHNBu(COOEt) (119)

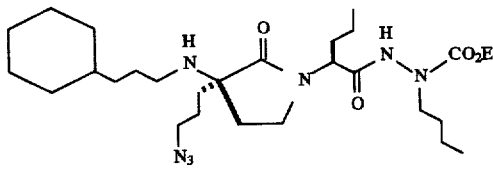

Step 1
Preparation of H$_2$N-α-(3-hydroxypropyl)-(R)-γ-Lactam-Nva-NHNBu(COOEt) (115)

Using procedures analogous to those employed in Example 33 (74→80), (91), the product of Example 35, Step 8, was converted to (115) NMR (500 MHz, CD$_3$OD): δ 4.56

(1H, dd, Nva-α), 4.12 (2H, br, CO₂CH₂), 3.55–3.35 (6H, m CH₂OH, CH₂NCO₂Et, Lac-γ), 0.98 (3H, t, CH₃), 0.92 (3H, t, CH₃).

Step 2

Preparation of Boc-α-(3-hydroxypropyl)-(R)-γ-Lactam-Nva-NHNBu(COOEt) (116)

(115) (64 mg, 0.16 mmol, a product of Step 1) was dissolved in CH₂Cl₂ at ambient temperature and Et₃N (33 μL, 1.5 eq) added, followed by Boc anhydride (38 mg, 1.1 eq). After 24 h and further additions of reagents the mixture was diluted with aq. NaHCO₃ solution and extracted with CH₂Cl₂. The organics were washed with 0.5N HCl, dried over Mg₂SO₄, filtered and concentrated. The residue was chromatographed on silica gel to give the title compound as a foam. NMR (400 MHz, CD₃OD): δ 4.50 (1H, br, Nva-a), 4.12 (2H, br, CO₂CH₂), 3.60–3.30 (6H, m CH₂OH, CH₂NCO₂Et, Lac-γ), 2.43 (1H, m), 1.41 (9H, s, tBuOCO), 0.98 (3H, t, CH₃), 0.92 (3H, t, CH₃).

Step 3

Preparation of Boc-α-(3-mesyloxypropyl)-(R)-γ-Lactam-Nva-NHNBu(COOEt) (117)

(116) (40 mg, 80 μmol, a product Step 2) was dissolved in CH₂Cl₂ at ambient temperature and pyridine (65 μL, 10 eq) added, followed by mesyl chloride (12 μL, 2 eq). After 3 h and mixture was loaded directly onto a silica gel chromatography column and chromatographed to give the title compound as an oil. NMR (400 MHz, CDCl₃): δ 4.42 (1H, br, Nva-α), 4.10 (2H, br, CH₂OMs), 4.10 (2H, q, CO2CH₂), 3.55–3.30 (4H, m, CH₂NCO₂Et, Lac-γ), 2.98 (3H, s, OSO₂CH₃), 1.44 (9H, s, tBuOCO), 0.92 (3H, t, CH₃), 0.88 (3H, t, CH₃).

Step 4

Preparation of Boc-α-(3-azidopropyl)-(R)-γ-Lactam-Nva-NHNBu(COOEt) (118)

(117) (45 mg, the product of Step 3) was dissolved in DMF and NaN₃ (8 mg, 1.5 eq) added. The mixture was heated to 80° C. After 2 h the mixture was cooled to ambient temperature, diluted with water and extracted with CH₂Cl₂. The organics were washed with water, dried over Mg₂SO₄, filtered and concentrated to give the title compound as an oil. NMR (500 MHz, CDCl₃): δ 5.15 (1H, br, NH), 4.57 (1H, br, Nva-α), 4.15 (2H, m, CO₂CH₂), 3.58–3.26 (6H, m, CH₂N₃, CH₂NCO₂Et, Lac-γ), 1.44 (9H, s, tBuOCO), 0.98 (3H, t, CH₃), 0.93 (3H, t, CH₃). Mass spectrum [ESI]: 548 (MNa⁺), 526 (MH⁺), 470, 426, 310.

Step 5

Preparation of cHx(CH₂)₃-α-(3-aziodopropyl)-(R)-γ-Lactam-Nva-NHNBu(COOEt) (119)

(118) (33 mg, the product of Step 4) was dissolved in 4N HCl in dioxane (1 mL). After 1 h the mixture was concentrated to give the crude amine salt as an oil. This was dissolved in methanol (750 μL) and 3-cyclohexylpropionaldehyde ( 17 μL, 1.5 eq) added followed by sodium cyanoborohydride (7 mg, 1.5 eq). After 90 min the mixture was diluted with aq. NaHCO₃ solution and extracted with EtOAc. The organics were dried over MgSO₄, filtered and concentrated. The residue was chromatographed twice on silica gel to give the title compound as an oil (20 mg). NMR (500 MHz, CD₃OD): δ 4.60 (1H, dd, Nva-α), 4.12 (2H, m, CO₂CH₂), 3.56–3.24 (6H, m, CH₂N₃, CH₂NCO₂Et, Lac-γ), 2.52 (1H, m, CH₂NH), 2.33 (1H, m, CH₂NH), 2.10 (1H, m, Lac-β), 2.05 (1H, m, Lac-β), 0.98 (3H, t, CH₃), 0.98 (3H, t, CH₃). Mass spectrum [ESI]: 550 (MH⁺).

EXAMPLE 53 cHx(CH₂)₃-α-(3-Aminopropyl)-(R)-γ-Lactam-Nva-NHNBu(COOEt) (120)

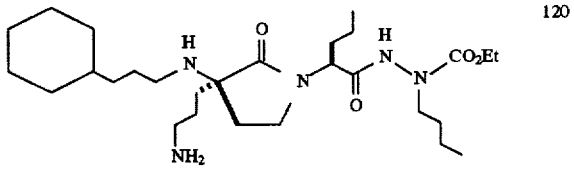

(119) (20 mg, the product of example 52) was dissolved in ethanol (1 mL) and 10% palladium on carbon added. The mixture was hydrogenated at 1 atm and ambient temperature. After 4 h the mixture was filtered through Celite™ diatomaceous earth and concentrated. The residue was chromatographed on silica gel to give the title compound as an oil (7 mg). NMR (500 MHz, CD₃OD): δ 4.61 (1H,m, Nva-α), 4.12 (2H, m, CO₂CH₂), 3.54–3.35 (4H, m, CH₂NCO₂Et, Lac-γ), 2.78 (1H, m, CH₂NH₂), 2.55 (2H, m, CH₂NH, CH₂NH₂), 2.33 (1H, m, CH₂NH), 2.08 (2H, m, Lac-β), 0.98 (3H, t, CH₃), 0.93 (3H, t, CH₃).

EXAMPLE 54 cHx(CH₂)₃-α-(3-guanidinopropyl)-(R)-γ-Lactam-Nva-NHNBu(COOEt) (121)

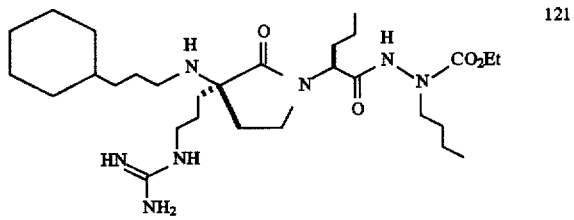

Using procedures analogous to those employed in Example 33 (74→79), the product of Example 35 Step 8 (91) was converted to Cbz-α-(3-hydroxypropyl)-(R)-γ-Lactam-Nva-NHNBu(COOEt). Cbz-α-(3-hydroxypropyl)-(R)-γ-Lactam-Nva-NHNBu(COOEt) (26 mg, 49 μmol), N,N'-bis(t-butoxycarbonyl)guanidine (25 mg, 2 eq) and triphenylphosphine (19 mg, 1.5 eq) were dissolved in toluene (0.5 mL) and cooled to 0° C. Diisopropyl azodicarboxylate (14 mg, 1.5 eq) was added over 15 min. The mixture allowed to warm to ambient temperature and stirred overnight. Purification by silica gel chromatography (direct loading of the reaction mixture) gave Cbz-α-(3-N,N'-bis(t-butoxycarbonyl)-guanidinopropyl)-(R)-γ-Lactam-Nva-NHNBu(COOEt) (12 mg). Cbz-α-(3-N,N'-bis(t-butoxycarbonyl)-guanidinopropyl)-(R)-γ-Lactam-Nva-NHNBu(COOEt) (25 mg) was dissolved in ethanol (0.5 mL) and 10% Pd/C (3.5 mg, 10 mol %) added. The mixture was hydrogenated at 1 atm H₂ and at ambient temperature for 4 h. The mixture was filtered through Celite™ diatomaceous earth and concentrated. The residue was dissolved in methanol (0.5 mL) at ambient temperature and acetic acid (7 μL, 4 eq), followed by 3-cyclohexylpropionaldehyde (7 μL, 1.5 eq) and sodium cyanoborohydride (3 mg, 1.5 eq). After 90 min the mixture was diluted with aq. NaHCO₃ solution and extracted with EtOAc. The organics were dried over MgSO₄, filtered and concentrated. The residue was chromatographed twice on silica gel to give cHex(CH₂)₃-α-(3-N,N'-bis(t-butoxycarbonyl)-guanidinopropyl)-(R)-γ-Lactam-Nva-NHNBu(COOEt) as an oil. chex(CH₂)₃-α-(3-

N,N'-bis(t-butoxycarbonyl)-guanidinopropyl)-(R)-γ-Lactam-Nva-NHNBu(COOEt) (5 mg) was dissolved in 4N HCl/dioxane and stirred for 6 h. The mixture was concentrated and chromatographed on silica gel to give cHex $(CH_2)_3$-α-(3-guanidinopropyl)-(R)-γ-Lactam-Nva-NHNBu (COOEt) (121) as an oil. NMR (500 MHz, $CD_3OD$, 40° C.): δ 4.6 (1H, dd, Nva-α), 4.12 (2H, m, $CO_2CH_2$), 3.62 (2H, m, Lac-γ), 3.46 (2H, m, $CB_2NCO_2Et$), 3.21 (2H, t, $CH_2NHC=NH(NH_2)$), 3.12 (1H, m, $cHxCH_2CH_2CH_2NH-$), 2.78 (1H, m, $cHxCH_2CH_2CH_2NH-$), 2.41 (2H, t, Lac-β), 1.0 (3H, t, Nva-$CH_3$), 0.93 (3H, t, nBu-$CH_3$). Mass spectrum [ESI]: 566 ($MH^+$).

EXAMPLE 55

Oral Composition

As a specific embodiment of an oral composition of a compound of this invention, 5 mg of a compound of structural formula I is formulated with sufficient finely divided lactose to provide a total amount of 580 to 590 mg to fill a size 0 hard gelatin capsule.

Biological Assays

Binding and Inhibition Assays

For direct binding assays, optimal concentrations of affinity purified DR1Dw1 (1.25 nM) or DR4Dw4 (10 nM) are incubated with serial dilutions of biotinylated rat myelin basic protein (RMBP) 90–102 in PBS (phosphate buffered saline) containing 0.75% octyl glucoside, pH 6.5, in 96-well polypropylene plates for 16 to 20 h at 37° C. In studies optimizing the assay it was determined that only between 5 to 10% of the DR molecules are capable of binding added peptide. Therefore, the effective concentration of DR1Dw1 and DR4Dw4 was approximately 0.125 and 1.0 nM, respectively. The conditions of the assays are shown to be in ligand excess, because twofold reduction of these class II concentrations does not change the measured $ED_{50}$ values. The DR-peptide complexes (50 μL) are transferred to wells of a 96-well EIA plate precoated with LB3.1, the monoclonal antibody which recognizes the DR alleles of MHC Class II, and blocked with PBS with fetal calf serum (FCS). An additional 50 μL of 50 mM Tris, pH 7.0, containing 0.75% octyl glucoside is added to each well and the mixture incubated overnight at 4° C. Excess peptide is removed by washing with PBS containing 0.05% Tween 20 (Polyoxyethylene sorbitan monolaurate) and 0.01% $NAN_3$. Europium-labeled streptavidin (Wallac Inc.) is added and incubated overnight. After washing, complexes are measured by the addition of Enhance™ buffer, the tradename for 0.1 M acetate phthalate buffer, pH 3.2, containing 0.1% Triton X-100, tradename for polyoxyethylene ethers and other surface active compounds of Union Carbide Chemicals and Plastics Co., Inc. (particularly, a non-ionic surfactant for recovery of membrane components under non-denaturing conditions) 15 gM 2-naphthoyltrifluoroacetone, and 50 μM tri-N-octylphosphine oxide, which buffer releases the chelated europium from streptavidin and forms a highly fluorescent micellar solution. The resultant fluorescence is measured using a fluorescent plate reader (e.g., DELPHIA, Wallac, Inc.). The data are analyzed using a four-parameter logistical curve tilt program (e.g., SigmaPlot) that calculates the concentration of biotinylated peptide giving a half-maximal signal ($ED_{50}$).

The ability of LB3.1 to bind DR1Dw1 and DR4Dw4 is shown to be equivalent by measuring the capacity of Ab-coated plates to bind serial dilutions of biotinylated DR molecules. Europium streptavidin is used to measure the number of DR molecules bound as described for the peptide binding assay.

The effects of pH on HLA-DR binding of RMBP 90–102 are explored by performing assays over a range from 4.0 to 9.0. The equivalently low $ED_{50}$ values are observed between pH 5.0 and 6.5, consistent with previous reports. Both lower $IC_{50}$ values and higher percentage occupancy are observed when octyl glucoside was used compared with Tween 20, dodecyl-β-D-maltoside, NP-40, CHAPS, octanoyl-N-methyl-glucamide, and Triton X-100.

The inhibition assay format is identical to the procedure described above with the exception that the unlabeled antagonist is serially diluted and incubated with constant concentrations of biotinylated RMBP 90–102 (0.3 nM for DR1Dw1 or 0.9 nM for DR4Dw4) and the MHC class II proteins. The concentration of unlabeled compound that prevents 50% of the labeled peptide from binding is the $IC_{50}$ value. The concentration of the biotinylated RMBP 90–102 in each assay is experimentally determined to be at least one-sixth of its measured $ED_{50}$ to assure the inhibition was primarily measuring the binding characteristics of the competitor. This was confirmed by demonstrating that a two- or four fold reduction in the biotinylated agonist peptide did not alter the $IC_{50}$ values obtained with unlabeled competitor proving that the receptor concentration was not limiting.

In particular, a protocol for carrying out the inhibition assay is given below.

Preparation of Antibody Plate

Day 1)

Add 115 μL of 5 μg/mL LB3.1 in 50 mM Tris HCl pH 9.6/azide to each well of a Costar EIA plate. Incubate the plate overnight at 4° C.

Day 2)

Wash the plate 4 times with water/0.05% Tween-20/azide. Add 200 μL of PBS/5% FCS/azide for 1 hour at 4° C. to block the plate. The plate may be held at this point for later use or used immediately.

Flip out the block. It is not necessary to wash the plate. At 50 μL of load buffer (50 mM Tris HCl, pH 8.0 0.75% octylglucoside). Add to this volume 50 μL of the reaction mix from day 2, step 3 below.

Preparation of Reaction Mixture

Day 2)

(1) Add the following to a polypropylene round bottom 96-well plate such as a Costar #3794:

(A) Diluent (Ca Mg free PBS adjusted to pH 6.5 with 0.1 M $KH_2PO_4$/0.75% octylglucoside/azide).81 μL (B) Competitor at 16.6 times the final concentration in diluent or diluent alone. 9 μL (C) Biotinylated RMBP (BRMBP) 90–102; 1.5 nM for DR1 or 4.5 nM for DR4 (These are 5 × stocks of final concentrations of 0.3 nM/DR1 or 0.9 nM/DR4) 30 μL (D) 6.25 nM DR1Dw1 or 50 nM DR4Dw4 (these are Drosophila transmembrane DR) (This is a 5× stock of the final concentration of 1.25 or 10 nM.) 30 μL Add the DR last and mix well at this time 150 μL (2) Incubate at 37° C. for 20 min and 5 hours.

(3) Add 50 μL of this reaction mixture to one well of the blocked antibody plate from day 2 above.

(4) Incubate overnight at 4° C. to capture the DR-peptide complexes.

(5) Wash 4× with $H_2O$/0.05% Tween-20/azide (6) Add 125 μL of 100 ng/mL europium streptavidin (Wallac Inc.) in Ca Mg free PBS with 3.5 mg DTPA, 1.6 mL of 30% BSA/500 mL to each well.

(7) Incubate 2 to 4 hours at 4° C.
(S) Wash 4 times.
(9) Add 125 µL of Enhance™ buffer (described above) and incubate at room temperature.
(10) Read the plates.

Representative IC$_{50}$ values for inhibition of peptide binding to DR1 by the corn compounds of the present invention are shown in the following table:

| Example | IC$_{50}$/µM @ 20' | IC$_{50}$/µM @ 5 h |
|---|---|---|
| 11 | 0.76 | 5.2 |
| 21 | 3.1 | 10.5 |
| 27(61) | 3.4 | 10.0 |
| 14 | 0.34 | 2.9 |
| 12 | 0.65 | 5.6 |
| 32 | 0.15 | 1.4 |
| 33 | 0.13 | 0.86 |
| 35 | 0.25 | 2.0 |
| 50 | 2.5 | 23.5 |
| 51 | 0.16 | 0.63 |
| 52 | 0.16 | 0.62 |
| 53 | 0.68 | 3.1 |
| 54 | 0.21 | 0.93 |

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula I:

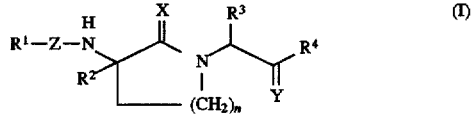

or a pharmaceutically acceptable salt thereof, wherein:

Z is selected from:
(a) CHR$^5$,
(b) —C(O)—,
(c) SO$_2$, and
(d) —C(O)—O—;

X is selected from:
(a) O, and
(b) S;

Y is selected from:
(a) O,
(b) H,H, and
(c) CHR$^6$;

R$^1$ is selected from
(a) C$_{1-10}$ alkyl, unsubstituted or substituted with one to three substituents selected from:

(1) aryl,
(2) cycloalkyl,
(3) halogen,
(4) NHR$^7$, and
(5) a heterocyclic ring, (b) C$_{2-10}$ alkenyl, unsubstituted or substituted with one to three substituents selected from:
(1) C$_{1-5}$alkyl,
(2) aryl,
(3) cycloalkyl,
(4) halogen,
(5) NHR$^7$, and
(6) a heterocyclic ring, (c) cycloalkyl, and
(d) a heterocylic ring;

R$^2$ is C$_{1-5}$ alkyl or C$_{2-5}$ alkenyl, unsubstituted or substituted with one to three substituents selected from:
(a) cycloalkyl,
(b) aryl,
(c) OH,
(d) NH$_2$,
(e) —NHCH=NH(NH$_2$),
(f) —NHCO-aryl, and
(g) halogen;

R$^3$ is C$_{1-5}$ alkyl, unsubstituted or substituted with one to three substituents selected from:
(a) cycloalkyl,
(b) aryl,
(c) OH,
(d) NH$_2$, and
(e) halogen;

R$^4$ selected from:
(a) H,
(b) NHNR$^6$R$^6$, and
(c) NHCHR$^6$R$^6$;

R$^5$ is selected from C$_{1-3}$ alkyl and H;

R$^6$ is selected from:
(a) C$_{1-8}$ alkyl, unsubstituted or substituted with one to three substituents selected from:
(1) —CONHR$^5$,
(2) —COOR$^5$,
(3) —COOH,
(4) OH,
(5) C$_{1-5}$alkoxy, and
(6) NH$_2$,
(b) H,
(c) —CONHR$^5$,
(d) —COOR$^5$, and
(e) —COOH;

R$^7$ is selected from:
(a) C$_{1-4}$ alkyl,
(b) C$_{1-4}$ alkoxycarbonyl,
(c) C$_{1-4}$ acyl, and
(d) C$_{1-4}$ sulfonyl;

n is an integer selected from 1 and 2;

cycloalkyl is selected from:
(a) C$_{3-8}$ saturated cycloalkyl, unsubstituted or substituted with one to three substituents selected from:
(1) C$_{1-4}$ alkyl,
(2) C$_{1-4}$ alkoxy,
(3) halogen, and
(4) hydroxy,
(b) C$_{3-8}$ saturated cycloalkyl substituted with aryl or C$_{3-8}$ cycloalkyl, and
(c) C$_{3-8}$ saturated cycloalkyl fused with aryl or C$_{3-8}$ cycloalkyl;

aryl is selected from:
(a) phenyl,
(b) naphthyl,
(c) indenyl,
(d) thiophenyl,
(e) benzothiophenyl,
(f) furanyl,
(g) benzofuranyl,
(h) pyrollyl,
(i) indolyl, and
(j) pyridyl;
wherein the aryl group is unsubstituted or substituted with one to three substituents selected from:
(1) $C_{1-4}$ alkyl,
(2) $C_{1-4}$ alkoxy,
(3) halogen, and
(4) hydroxy; and
a heterocyclic ring is selected from:
(a) $C_{3-8}$ cycloalkyl wherein one or two of the carbon atoms are replaced with a heteroatom selected from oxygen, nitrogen and sulfur, unsubstituted or substituted with one to three substituents selected from:
(1) $C_{1-4}$ alkyl,
(2) $C_{1-4}$ alkoxy,
(3) halogen, and
(4) hydroxy;
(b) $C_{3-8}$ saturated cycloalkyl wherein one or two of the carbon atoms are replaced with a heteroatom selected from oxygen, nitrogen and sulfur, substituted with aryl or $C_{3-8}$ cycloalkyl, and
(c) $C_{3-8}$ saturated cycloalkyl wherein one or two of the carbon atoms are replaced with a heteroatom selected from oxygen, nitrogen and sulfur, fused with aryl or $C_{3-8}$ cycloalkyl.

2. The compound of claim 1 wherein:
Z is $CHR^5$;
X is O;
Y is O;
$R^1$ is selected from
(a) $C_{1-10}$ alkyl, unsubstituted or substituted with one to three substituents selected from:
(1) aryl,
(2) cycloalkyl, and
(b) cycloalkyl;
$R^2$ is $C_{1-5}$ alkyl, unsubstituted or substituted with:
(a) $NH_2$,
(b) $NHCH=NH(NH_2)$, and
(c) aryl;
$R^3$ is $C_{1-5}$ alkyl;
$R^4$ selected from:
(a) $NHNR^6R^6$, and
(b) $NHCHR^6R^6$;
$R^5$ is selected from $C_{1-3}$ alkyl and H;
$R^6$ is selected from:
(a) $C_{1-8}$ alkyl,
(b) —$CONHR^5$,
(c) —$COOR^5$, and
n has a value of 1 or 2.

3. The compound of claim 1 selected from the group consisting of:
(1) [Et]$CH_3CH_2OCO$-[Phe]Phenylalaninyl-(R)-γ-Lactam-[Nva-Leu]Norvalinyl-Leucinyl-$NH_2$,
(2) [Et]$CH_3CH_2OCO$-[Cha]Cyclohexylalaninyl-(R)-γ-Lactam-[Nva-Leu]Norvalinyl-Leucinyl-$NH_2$,
(3) [cHx($CH_2$)3-Cyclohexylpropyl-(R)-γ-Lactam-[Nva-Leu]Norvalinyl-Leucinyl -$NH_2$,
(4) [Et]$CH_3CH_2OCO$-[Phe]Phenylalaninylψ($CH_2NH$)-(R)-γ-Lactam-Nva-Leu]Norvalinyl-Leucinyle-$NH_2$,
(5) [Ph]Phenyl($CH_2$)$_3$-(R)-γ-Lactam-[Nva-Leu]Norvalinyl-Leucinyl-$NH_2$,
(6) [Et]$CH_3CH_2OCO$-[Cha]Cyclohexylalaninylψ($CH_2NH$)-(R) -γ-Lactam-[Nva-Leu]Norvalinyl-Leucinyl-$NH_2$,
(7) [Ph]Phenyl(CH=$CHCH_2$)-(R)-γ-Lactam-[Nva-Leu]Norvalinyl-Leucinyl-$NH_2$,
(8) [Ph]Phenyl(C($CH_3$)=$CHCH_2NH$)-(R)-γ-Lactam-[Nva-Leu]Norvalinyl-Leucinyl-$NH_2$,
(9) [cHx]Cyclohexyl(CH=C($CH_3$)$CH_2$)-(R)-γ-Lactam-[Nva-Leu]Norvalinyl-Leucinyl-$NH_2$,
(10) [cHx]Cyclohexyl($CH_2$C($CH_3$)$CH_2$)-(R)-γ-Lactam-[Nva-Leu]Norvalinyl-Leucinyl-$NH_2$,
(11) [cHx]Cyclohexyl(($CH_3$)C=$CHCH_2$)-(R)-γ-Lactam-[Nva-Leu]Norvalinyl-Leucinyl-$NH_2$,
(12) [cHx]Cyclohexyl (($CH_3$)$CHCH_2CH_2NH$)-(R)-γ-Lactam- [Nva-Leu]Norvalinyl-Leucinyl-$NH_2$,
(13) [cHp]Cycloheptyl(CH=$CHCH_2$)-(R)-γ-Lactam-[Nva-Leu]Norvalinyl-Leucinyl-$NH_2$,
(14) [cHp]Cycloheptyl($CH_2$)3-(R)-γ-Lactam-[Nva-Leu]Norvalinyl-Leucinyl-$NH_2$,
(15) [cOct]Cyclooctyl(CH=$CHCH_2$)-(R) -γ-Lactam-[Nva-Leu]Norvalinyl-Leucinyl-$NH_2$,
(16) [cOct]Cyclooctyl($CH_2$)$_3$-(R)-γ-Lactam-[Nva-Leu]Norvalinyl-Leucinyl-$NH_2$,
(17) [cPn]Cyclopentyl($CH_2$)$_3$-(R)-γ-Lactam-[Nva-Leu]Norvalinyl-Leucinyl-$NH_2$,
(18) [cHx($CH_2$)$_3$]3-Cyclohexylpropyl-(R)-γ-Lactam-[Nva]Norvalinyl-(α-aza)-[Leu]Leucinyl-$NH_2$,
(19) [cHx]Cyclohexyl($CH_2$)$_3$HN- (R)-γ-Lactam- [Nva-Leu]Norvalinyl-Leucinyl-O[Bn]benzyl,
(20) [cHx($CH_2$)$_3$]3-Cyclohexylpropyl-(R)-γ-Lactam-[Nva-Leu]Norvalinyl-Leucinyl-OH,
(21) [Et]$CH_3CH_2OCO$- [Phe]Phenylal aninyl-(S)-γ-Lactam-[Nva-Leu]Norvalinyl-Leucinyl-$NH_2$,
(22) [Et]$CH_3CH_2OCO$-[Cha]Cyclohexylalaninyl-(S)-γ-Lactam-[Nva-Leu]Norvalinyl-Leucinyl-$NH_2$,
(23) [cHx($CH_2$)$_3$]3-Cyclohexylpropyl-(S)-γ-Lactam-[Nva-Leu]Norvalinyl-Leucinyl-$NH_2$,
(24) [Et]$CH_3CH_2OCO$-[Phe]Phenyl alaninyl-(R)-δ-Lactam-L-[Nva-Leu]Norvalinyl-Leucinyl-$NH_2$,
(25) [Et]$CH_3CH_2OCO$-[Phe]Phenylalaninyl-(R)-δ-Lactam-D-[Nva-Leu]Norvalinyl-Leucinyl-$NH_2$,
(26) [Et]$CH_3CH_2OCO$-[Cha]Cyclohexylalaninyl-(R)-δ-Lactam-L-[Nva-Leu]Norvalinyl-Leucinyl-$NH_2$,
(27) [Et]$CH_3CH_2OCO$-[Cha]Cyclohexylalaninyl-(R)-5-Lactam-D-[Nva-Leu]Norvalinyl-Leucinyl-$NH_2$,
(28) [cHx($CH_2$)$_3$]3-Cyclohexylpropyl-(R)-δ-Lactam-D,L-[Nva-Leu]Norvalinyl-Leucinyl-$NH_2$,
(29) [Et]$CH_3CH_2OCO$-[Phe]Phenyl alaninyl-(S)-δ-Lactam-L-[Nva-Leu]Norvalinyl-Leucinyl-$NH_2$,
(30) [Et]$CH_3CH_2OCO$-[Phe]Phenylalaninyl-(S)-δ-Lactam-D-[Nva-Leu]Norvalinyl-Leucinyl-$NH_2$,
(31) [Et]$CH_3CH_2OCO$ -[Cha]Cyclohexyl alaninyl-(S)-δ-Lactam-L-[Nva -Leu]Norvalinyl-Leucinyl-$NH_2$,
(32) [Et]$CH_3CH_2OCO$-[Cha]Cyclohexylalaninyl-(S)-5-Lactam-D-[Nva-Leu]Norvalinyl-Leucinyl-$NH_2$,
(33) [cHx($CH_2$)$_3$]3-Cyclohexylpropyl-(S)-δ-Lactam-L-[Nva-Leu]Norvalinyl-Leucinyl-$NH_2$,
(34) [cHx($CH_2$)$_3$]3-Cyclohexylpropyl-(S)-δ-Lactam-D-[Nva-Leu]Norvalinyl-Leucineyl-$NH_2$,

(35) [cHx (CH$_2$)$_3$]3-Cyclohexylpropyl-α-Propyl- (R)-γ-Lactam-[Nva-Leu]Norvalinyl-Leucinyl-NH$_2$,

(36) [cHp]Cycloheptyl CH=CHCH$_2$-α-Propyl- (R)-γ-Lactam-[Nva-Leu]Norvalinyl-Leucinyl-NH$_2$,

(37) [cHp]Cycloheptyl(CH$_2$)$_3$-α-Propyl-(R)-γ-Lactam-[Nva-Leu]Norvalinyl-Leucinyl-NH$_2$.

(38) [cHx(CH$_2$)$_3$]3-Cyclohexylpropyl-α-(3-Hydroxypropyl)-(R)-γ-Lactam-[Nva-Leu]Norvalinyl-Leucinyl-NH$_2$,

(39) [cHx(CH$_2$)$_3$]3 -Cyclohexylpropyl-α-Propyl-(S)-γ-Lactam-[Nva-Leu]Norvalinyl-Leucinyl-NH$_2$,

(40) [cHx(CH$_2$)$_3$]3 -Cyclohexylpropyl-α-propyl- (R)-γ-Lactam-[Nva]Norvalinyl-NHNBu(COO[Et]CH$_2$CH$_3$),

(41) [cHp]CycloheptylCH=CHCH$_2$-α-propyl-(R)-γ-Lactam-[Nva]Norvalinyl-NHNBu(COO[Et]CH$_2$CH$_3$),

(42) [cHp]Cycloheptyl(CH$_2$)$_3$-α-propyl-(R)-γ-Lactam-[Nva]Norvalinyl-NHNBu(COO[Et]CH$_2$CH$_3$),

(43) [Boc]t-Butoxycarbonyl-[Cha]Cyclohexylalaninylψ(CH$_2$HN)-α-Propyl-(R)-γ-Lactam-[Nva]Norvalinyl-NHNBu(COO[Et]CH$_2$CH$_3$),

(44) HCl.H$_2$N-[Cha]Cyclohexylalaninylψ(CH$_2$HN)-α-Propyl-(R)-γ-Lactam-[Nva]Norvalinyl-NHNBu(COO[Et]CH$_2$CH$_3$),

(45) MeSO$_2$-[Cha]Cyclohexylalaninyhlt(CH$_2$HN)-α-Propyl-(R)-γ-Lactam-[Nva]Norvalinyl-NHNBu(COO[Et]CH$_2$CH$_3$),

(46) Pr-[Cha]Cyclohexylalaninylψ(CH$_2$HN)-α-Propyl-(R)-γ-Lactam-[Nva]Norvalinyl-NHNBu(COO[Et]CH$_2$CH$_3$),

(47) Ac-[Cha]Cyclohexylalaninylψ(CH$_2$HN)-α-Propyl-(R)-γ-Lactam-[Nva]Norvalinyl-NHNBu(COO[Et]CH$_2$CH$_3$),

(48) [Boc]t-Butoxycarbonyl-D-[Cha]Cyclohexylalaninyψ(CH$_2$HN)-α-Propyl-(R)-γ-Lactam-[Nva]Norvalinyl-NHNBu(COO[Et]CH$_2$CH$_3$),

(49) HCl.H$_2$N-D-[Cha]Cyclohexylalaninylψ(CH$_2$HN)-α-Propyl-(R)-γ-Lactam-[Nva]Norvalinyl-NHNBu(COO[Et]CH$_2$CH$_3$),

(50) MeSO$_2$-D-[Cha]Cyclohexylalaninylψ(CH$_2$HN)-α-Propyl-(R)-γ-Lactam-[Nva]Norvalinyl-NHNBu (COO[Et]CH$_2$CH$_3$),

(51) Ac-D-[Cha]Cyclohexylalaninylψ(CH$_2$HN)-α-Propyl-(R)-γ-Lactam-[Nva]Norvalinyl-NHNBu(COO[Et]CH$_2$CH$_3$),

(52) [Ph]Phenyl (CH$_2$)$_2$SO$_2$-(R)-γ-Lactam-[Nva-Leu]Norvalinyl-Leucinyl-NH$_2$,

(53) [Cbz]Benzyloxycarbonyl-(R)-γ-Lactam-[Nva-Leu]Norvalinyl-Leucinyl-NH$_2$,

(54) [Boc]t-Butoxycarbonyl-(R)-γ-Lactam-[Nva]Norvalinyl-CH=CHCO$_2$[Et]CH$_2$CH$_3$,

(55) [cHx(CH$_2$)$_3$]3-Cyclohexylpropyl-(R)-γ-Lactam-[Nva]Norvalinylψ(CH$_2$NH)[Leu]Leucinyl-NH$_2$,

(56) [cHx(CH$_2$)$_3$]3-Cyclohexylpropyl-(R)-γ-Thiolactam-[Nva-Leu]Norvalinyl-Leucinyl-NH$_2$,

(57) (CH$_3$)$_2$CCH(CH$_2$)$_2$CH(CH$_3$)CH$_2$-(R)-γ-Lactam-[Nva-Leu]Norvalinyl-Leucinyl-NH$_2$,

(58) [cHx]CyclohexylCH(CH$_2$)CHCH$_2$-(R)-γ-Lactam-[Nva-Leu]Norvalinyl-Leucinyl-NH$_2$,

(59) [4H]-Naphthyl-CH$_2$-(R)-γ-Lactam-[Nva-Leu]Norvalinyl-Leucinyl-NH$_2$,

(60) [cHx(CH$_2$)$_3$]3-Cyclohexylpropyl-α-(3-Hydroxypropyl)-(R)-γ-Lactam-[Nva]Norvalinyl-NHNBu(COO[Et]CH$_2$CH$_3$),

(61) [cHx(CH$_2$)$_3$]3-Cyclohexylpropyl-α-(3-Azidopropyl)-(R)-γ-Lactam-[Nva]Norvalinyl-NHNBu(COO[Et]CH$_2$CH$_3$),

(62) [cHx(CH$_2$)$_3$]3-Cyclohexylpropyl-α-(3-Aminopropyl)-(R)-γ-Lactam-[Nva]Norvalinyl-NHNBu(COO[Et]CH$_2$CH$_3$),

(63) [cHx(CH$_2$)$_3$]3-Cyclohexylpropyl-α-(3-guanidinopropyl)-(R)-γ-Lactam-[Nva]Norvalinyl-NHNBu(COO[Et]CH$_2$CH$_3$),

(64) [cHx(CH$_2$)$_3$]3-Cyclohexylpropyl-(R)-γ-Lactam-[Nva]Norvalinyl-(α-aza)-[Leu]Leucinyl-O[Et]CH$_2$CH$_3$,

(65) [cHx(CH$_2$)$_3$]3-Cyclohexylpropyl-(R)-γ-Lactam-[Nva]Norvalinyl-NHNBu(COOMe),

(66) [cHx(CH$_2$)$_3$]3-Cyclohexylpropyl-(R)-γ-Lactam-[Nva]Norvalinyl-NHN(2-methylbutyl)(COO[Et]CH$_2$CH$_3$),

(67) [cHx(CH$_2$)$_3$]3-Cyclohexylpropyl-(R)-γ-Lactam-[Nva]Norvalinyl-NHN(3-methylbutyl)(COO[Et]CH$_2$CH$_3$),

(68) [cHx(CH$_2$)$_3$]3-Cyclohexylpropyl-(R)-γ-Lactam-[Nva]Norvalinyl-NHNiBu(COO[Et]CH$_2$CH$_3$),

(69) [cHx(CH$_2$)$_3$]3-Cyclohexylpropyl-(R)-γ-Lactam-[Nva]Norvalinyl-NHN(cyclohexylmethyl) (COO[Et]CH$_2$CH$_3$),

(70) [cHx(CH$_2$)$_3$]3-Cyclohexylpropyl-(R)-γ-Lactam-[Nva]Norvalinyl-NHNBu$_2$,

(71) [cHx (CH$_2$)$_3$]3- Cyclohexylpropyl-(R)-γ-Lactam-[Nva]Norvalinyl -NHNBu(SO$_2$Me),

(72) [4H]-naphthylmethyl-(R)-γ-Lactam-[Nva]Norvalinyl-NHNBu(COO[Et]CH$_2$CH$_3$),

(73) [10H]-naphthylmethyl-(R)-γ-Lactam-[Nva]Norvalinyl-NHNBu(COO[Et]CH$_2$CH$_3$),

(74) [8H]-indenylethyl-(R)-γ-Lactam-[Nva]NorvalinylNHNBu(COOEt),

(75) [10H]-naphthylmethyl-α-(3-guanidinopropyl) (R)-γ-Lactam-[Nva]Norvalinyl-NHNBu(COO[Et]CH$_2$CH$_3$),

(76) [10H]-naphthylmethyl-α-(3-Hydroxypropyl)-(R)-γ-Lactam-[Nva]Norvalinyl-NHNu(COO[Et]CH$_2$CH$_3$),

(77) [10H]-naphthylmethyl-α-(3-Azidopropyl)-(R)-γ-Lactam-[Nva]Norvalinyl-NHNBu(COO[Et]CH$_2$CH$_3$),

(78) [10H]-naphthylmethyl-α-(3-Aminopropyl)-(R)-γ-Lactam-[Nva]Norvalinyl-NHNBu(COO[Et]CH$_2$CH$_3$), and pharmaceutically acceptable salts thereof.

4. The compound of claim 1 selected from the group consisting of:

(1) [cHx(CH$_2$)$_3$]3-Cyclohexylpropyl-(R)-γ-Lactam-[Nva-Leu]Norvalinyl-Leucinyl-NH$_2$, (2) [Ph]Phenyl(CH$_2$)$_3$-(R)-γ-Lactam-[Nva-Leu]Norvalinyl-Leucinyl-NH$_2$, (3) [Ph]Phenyl(CH=CHCH$_2$)-(R)-γ-Lactam-[Nva-Leu]Norvalinyl-Leucinyl-NH$_2$, (4) [PhlPhenyl(C(CH$_3$)=CHCH$_2$NH)-(R)-γ-Lactam-[Nva-Leu]Norvalinyl-Leucinyl-NH$_2$, (5) [cHx]Cyclohexyl(CH=C(CH$_3$)CH$_2$)-(R)-γ-Lactam-[Nva-Leu]Norvalinyl-Leucinyl-NH$_2$, (6) [cHx]Cyclohexyl(CH$_2$C(CH$_3$)CH$_2$)-(R)-y-Lactam-[Nva-Leu]Norvalinyl-Leucinyl-NH$_2$, (7) [cHx]Cyclohexyl((CH$_3$)C=CHCH$_2$)-(R)-γ-Lactam-[Nva-Leu]Norvalinyl-Leucinyl-NH$_2$, (S) [cHx]Cyclohexyl((CH$_3$)CHCH$_2$CH$_2$NH)-(R)-γ-Lactam-[Nva-Leu]Norvalinyl-Leucinyl-NH$_2$.

(9) [cHp]Cycloheptyl(CH=CHCH₂)-(R)-γ-Lactam-[Nva-Leu]Norvalinyl-Leucinyl-NH₂.

(10) [cHp]Cycloheptyl(CH₂)₃-(R)-γ-Lactam-[Nva-Leu]Norvalinyl-Leucinyl-NH₂.

(11) [cOct]Cyclooctyl(CH=CHCH₂)-(R)-γ-Lactam-[Nva-Leu]Norvalinyl-Leucinyl-NH₂.

(12) [cOct]Cyclooctyl(CH₂)3-(R)-γ-Lactam-[Nva-Leu]Norvalinyl-Leucinyl-NH₂.

(13) [cPn]Cyclopentyl(CH₂)₃-(R)-γ-Lactam-[Nva-Leu]Norvalinyl-Leucinyl-NH₂.

(14) [cHx(CH₂)₃]3-Cyclohexylpropyl-(R)-γ-Lactam-[Nva]Norvalinyl]-α-aza-[Leu]Leucinyl-NH₂.

(15) [cHx(CH₂)₃]3-Cyclohexylpropyl-α-Propyl-(R)-γ-Lactam-[Nva-Leu]Norvalinyl-Leucinyl-NH₂.

(16) [cHp]CycloheptylCH=CHCH₂-α-Propyl-(R)-γ-Lactam-[Nva-Leu]Norvalinyl-Leucinyl-NH₂.

(17) [cHp]Cycloheptyl(CH₂)₃- α-Propyl-(R)-γ-Lactam-[Nva-Leu]Norvalinyl-Leucinyl-NH₂.

(18) [cHx(CH₂)₃]3-Cyclohexylpropyl-α-(3-Hydroxypropyl)-(R)-γ-Lactam-[Nva-Leu]Norvalinyl-Leucinyl-NH₂.

(19) [cHx(CH₂)₃]3-Cyclohexylpropyl-α-propyl-(R)-γ-Lactam-[Nva]Norvalinyl-NHNBu(COO[Et]CH₂CH₃).

(20) [cHp]CyeloheptylCH=CHCH₂-α-propyl-(R)-γ-Lactam-[Nva]Norvalinyl-NHNBu(COO[Et]CH₂CH₃).

(21) [cHp]Cycloheptyl(CH₂)₃-α-propyl-(R)-γ-Lactam-[Nva]Norvalinyl-NHNu(COO[Et]CH₂CH₃).

(22) [cHx]Cyclohexyl CH(CH₂)CHCH₂-(R)-γ-Lactam-[Nva-Leu]Norvalinyl-Leucinyl-NH₂.

(23) [4H]-Naphthyl-CH₂-(R)-γ-Lactam-[Nva-Leu]Norvalinyl-Leucinyl-NH₂.

(24) [cHx(CH₂)₃]3-Cyclohexylpropyl-α-(3-Hydroxypropyl)-(R)-γ-Lactam-[Nva]Norvalinyl-NHNu(COO[Et]CH₂CH₃).

(25) [cHx(CH₂)₃]3-Cyclohexylpropyl-α-(3-Azidopropyl)-(R)-γ-Lactam-[Nva]Norvalinyl-NHNBu(COO[Et]CH₂CH₃).

(26) [cHx(CH₂)₃]3-Cyclohexylpropyl-α-(3-Aminopropyl)-(R)-γ-Lactam-[Nva]Norvalinyl-NHNBu(COO[Et]CH₂CH₃).

(27) [cHx(CH₂)₃]3-Cyclohexylpropyl-α-(3-guanidinopropyl)-(R)-γ-Lactam-[Nva]Norvalinyl-NHNBu(COO[Et]CH₂CH₃).

(28) [cHx(CH₂)₃]3-Cyclohexylpropyl-(R)-γ-Lactam-[Nva]Norvalinyl-(α-aza)-[Leu]Leucinyl-O[Et]CH₂CH₃.

(29) [cHx(CH₂)₃]3-Cyclohexylpropyl-(R)-γ-Lactam-[Nva]Norvalinyl-NHNBu(COOMe).

(30) [cHx(CH₂)₃]3-Cyclohexylpropyl-(R)-γ-Lactam-[Nva]Norvalinyl-NHN(2-methylbutyl)(COO[Et]CH₂CH₃).

(31) [cHx(CH₂)₃]3-Cyclohexylpropyl-(R)-γ-Lactam-[Nva]Norvalinyl-NHN (3-methylbutyl)(COO[Et]CH₂CH₃).

(32) [cHx(CH₂)₃]3-Cyclohexylpropyl-(R)-γ-Lactam-[Nva]Norvalinyl-NHNiBu(COO[Et]CH₂CH₃).

(33) [cHx(CH₂)₃]3-Cyclohexylpropyl-(R)-γ-Lactam-[Nva]Norvalinyl-NHN(cyclohexylmethyl)(COO[Et]CH₂CH₃).

(34) [cHx(CH₂)₃]3-Cyclohexylpropyl-(R)-γ-Lactam-[Nva]Norvalinyl-NHNHNBu₂.

(35) [cHx(CH₂)₃]3-Cyclohexylpropyl-(R)-γ-Lactam-[Nva]Norvalinyl-NHNBu(SO₂Me).

(36) [4H]-naphthylmethyl-(R)-γ-Lactam-[Nva]Norvalinyl-NHNBu(COO[Et]CH₂CH₃).

(37) [10H]-naphthylmethyl-(R)-γ-Lactam-[Nva]Norvalinyl-NHNu(COO[Et]CH₂CH₃).

(38) [8H]-indenylethyl-(R)-γ-Lactam-[Nva]Norvalinyl-NHNBu(COO[Et]CH₂CH₃).

(39) [10H]-naphthylmethyl-α-(3-guanidinopropyl) (R)-γ-Lactam-[Nva]Norvalinyl-NHNBu(COO[Et]CH₂CH₃).

(40) [10H]-naphthylmethyl-α-(3-Hydroxypropyl)-(R)-γ-Lactam-[Nva]Norvalinyl-NHNBu(COO[Et]CH₂CH₃).

(41) [10H]-naphthylmethyl-α-(3-Azidopropyl)-(R)-γ-Lactam-[Nva]Norvalinyl-NHNBu(COO[Et]CH₂CH₃).

(42) [10H]-naphthylmethyl-α-(3-Aminopropyl)-(R)-γ-Lactam-[Nva]Norvalinyl-NHNBu(COO[Et]CH₂CH₃), and pharmaceutically acceptable salts thereof.

5. A method of inhibiting peptide binding to MHC class II molecules comprising the administration of a compound according to claim 1.

6. A method for treating autoimmune diseases comprising the step of administering to a mammal in need of such treatment a therapeutically effective amount of a compound of claim 1.

7. The method of claim 6 wherein the autoimmune disease is selected from:

(1) rheumatoid arthritis, (2) Type 1 diabetes, (3) multiple sclerosis, (4) lupus erythematosis, (5) Graves disease, and (6) pemphigus.

8. A composition comprising a pharmaceutically acceptable carrier and a therapeutically effective amount of a compound of claim 1.

9. A composition comprising a pharmaceutically acceptable carrier and a therapeutically effective amount of a compound of claim 4.

* * * * *